United States Patent [19]
DeFonzo et al.

[11] Patent Number: 5,497,933
[45] Date of Patent: Mar. 12, 1996

[54] APPARATUS AND METHOD FOR APPLYING SURGICAL STAPLES TO ATTACH AN OBJECT TO BODY TISSUE

[75] Inventors: Stephan A. DeFonzo, Bridgeport, Conn.; Wayne P. Young, Brewster, N.Y.; Samson L. Pennatto, Danbury; Andrew Komlosi, Fairfield, both of Conn.

[73] Assignee: United States Surgical Corporation, Norwalk, Conn.

[21] Appl. No.: 133,978

[22] Filed: Oct. 8, 1993

Related U.S. Application Data

[63] Continuation-in-part of Ser. No. 950,425, Sep. 23, 1992, Pat. No. 5,356,064, which is a continuation-in-part of Ser. No. 861,065, Mar. 31, 1992, Pat. No. 5,364,002, which is a continuation-in-part of Ser. No. 782,290, Oct. 18, 1991, Pat. No. 5,289,963.

[51] Int. Cl.$^6$ ..................................................... A61B 17/00
[52] U.S. Cl. ................... 227/175.1; 606/219; 227/176.1
[58] Field of Search .................................... 606/219, 220; 227/175–182, 901, 19

[56] References Cited

U.S. PATENT DOCUMENTS

| | | |
|---|---|---|
| Re. 28,932 | 8/1976 | Noiles et al. . |
| Re. 33,362 | 10/1990 | Mongeon et al. . |
| 389,660 | 9/1888 | Mandel et al. . |
| 2,448,741 | 9/1948 | Scott et al. . |
| 3,054,406 | 9/1962 | Usher . |
| 3,124,136 | 3/1964 | Usher . |

(List continued on next page.)

FOREIGN PATENT DOCUMENTS

| | | | |
|---|---|---|---|
| 0041022 | 12/1981 | European Pat. Off. . | |
| 0085930 | 8/1983 | European Pat. Off. | 227/176 |
| 116220 | 8/1984 | European Pat. Off. . | |
| 2330182 | 1/1975 | Germany . | |
| 2703529 | 8/1978 | Germany . | |
| 330713 | 7/1984 | Germany . | |
| WO93/14706 | 8/1993 | WIPO | 227/175 |

OTHER PUBLICATIONS

M–D–D–I Report, Sep. 1991 Ethicon Endoscopic Staple for Hernia Repair.
Information Booklet for Auto Suture® Skin & Fascia Suture® Surgical Stapling Instruments.
Information Booklet for Auto Suture® Multifire Premium ™ Disposable Skin Stapler and Disposable Loading Unit.
Publication Entitled Shape Memory Alloys From Scientific American Nov. 1979.
U.S. Patent Appln. Serial No. 08/035,512, filed Mar. 22, 1993, which is a file wrapper continuation of U.S. Patent Appln. Serial No. 07/631,373, filed Dec. 20, 1990.

(List continued on next page.)

*Primary Examiner*—Stephen C. Pellegrino
*Assistant Examiner*—Jeffrey A. Schmidt

[57] ABSTRACT

An apparatus is disclosed for endoscopic application of surgical staples to body tissue in laparoscopic hernia surgery, preferably with surgical mesh. The apparatus includes a staple storage cartridge supported on a pivotal support system at the distal end of the endoscopic section. An elongated pusher system extends from the frame to the endoscopic section and individually advances the staples distally. A pair of legs project distally from the pusher plate to engage the staple during closure to prevent unwanted roll or deformation of the staple. A trigger system actuates the pusher. An anvil structure having rounded anvil legs to match the configuration of the staples provides for individually closing each staple to encompass at least a portion of the surgical mesh and to penetrate the body tissue to attach the portion of the mesh to the body tissue. The staple storage cartridge may be pivoted with respect to the longitudinal axis of the endoscopic section from 0° to about 20°, 45°, and 65° and the cartridge may be rotated about its own axis independent of the endoscopic section. The distalmost tip of the instrument includes two distally extending members which engage the body tissue to stabilize the orientation of the instrument during application of staples.

19 Claims, 47 Drawing Sheets

U.S. PATENT DOCUMENTS

| | | |
|---|---|---|
| 3,314,431 | 4/1967 | Smith, Jr. . |
| 3,494,533 | 2/1970 | Green et al. . |
| 3,593,903 | 7/1971 | Astafiev et al. . |
| 3,643,851 | 2/1972 | Green et al. . |
| 3,763,860 | 10/1973 | Clarke . |
| 3,777,538 | 12/1973 | Weatherly et al. . |
| 3,837,555 | 9/1974 | Green ................................. 227/19 |
| 3,871,379 | 3/1975 | Clarke . |
| 3,955,581 | 5/1976 | Spasiano et al. . |
| 4,014,492 | 3/1977 | Rothfuss . |
| 4,027,510 | 6/1977 | Hiltebrandt . |
| 4,043,504 | 8/1977 | Hueil et al. . |
| 4,127,227 | 11/1978 | Green . |
| 4,196,836 | 4/1980 | Becht . |
| 4,204,623 | 5/1980 | Green . |
| 4,207,873 | 6/1980 | Kruy . |
| 4,256,251 | 3/1981 | Moshofsky . |
| 4,261,244 | 4/1981 | Becht et al. . |
| 4,316,468 | 2/1982 | Klieman et al. . |
| 4,317,535 | 3/1982 | Huftel et al. . |
| 4,321,002 | 3/1982 | Froehlich . |
| 4,347,847 | 9/1982 | Usher . |
| 4,349,028 | 9/1982 | Green . |
| 4,375,866 | 3/1983 | Giersch et al. . |
| 4,399,810 | 8/1983 | Samuels et al. . |
| 4,403,693 | 9/1983 | Froehlich . |
| 4,406,392 | 9/1983 | Campbell et al. . |
| 4,407,286 | 10/1983 | Noiles et al. . |
| 4,452,245 | 6/1984 | Usher . |
| 4,470,532 | 9/1984 | Froehlich . |
| 4,485,816 | 12/1984 | Krumme . |
| 4,485,953 | 12/1984 | Rothfuss ................................. 227/19 |
| 4,489,875 | 12/1984 | Crawford et al. . |
| 4,496,090 | 1/1985 | Crevier et al. . |
| 4,505,273 | 3/1985 | Braun et al. . |
| 4,506,819 | 3/1985 | Rand . |
| 4,509,518 | 4/1985 | McGarry et al. . |
| 4,519,532 | 5/1985 | Foslien . |
| 4,520,817 | 6/1985 | Green . |
| 4,523,695 | 6/1985 | Braun et al. . |
| 4,523,707 | 6/1985 | Blake, III et al. . |
| 4,526,174 | 7/1985 | Froehlich . |
| 4,527,724 | 7/1985 | Chow et al. . |
| 4,527,726 | 7/1985 | Assell et al. ................................. 227/19 |
| 4,532,927 | 8/1985 | Miksza, Jr. . |
| 4,550,715 | 11/1985 | Santangelo et al. . |
| 4,562,839 | 1/1986 | Blake, III et al. . |
| 4,566,620 | 1/1986 | Green et al. . |
| 4,573,622 | 3/1986 | Green et al. . |
| 4,583,670 | 4/1986 | Alvarado . |
| 4,591,086 | 5/1986 | Campbell et al. . |
| 4,592,498 | 6/1986 | Braun et al. ................................. 227/19 |
| 4,596,350 | 6/1986 | Smith et al. ................................. 227/19 |
| 4,607,638 | 8/1986 | Crainich . |
| 4,610,251 | 9/1986 | Kumar . |
| 4,610,383 | 9/1986 | Rothfuss et al. . |
| 4,616,650 | 10/1986 | Green et al. . |
| 4,618,086 | 10/1986 | Li et al. . |
| 4,619,391 | 10/1986 | Sharkany et al. . |
| 4,624,254 | 11/1986 | McGarry et al. . |
| 4,634,035 | 1/1987 | Li et al. . |
| 4,655,221 | 4/1987 | Devereux . |
| 4,662,373 | 5/1987 | Montgomery et al. . |
| 4,662,555 | 5/1987 | Thornton . |
| 4,664,305 | 5/1987 | Blake, III et al. . |
| 4,665,906 | 5/1987 | Jervis . |
| 4,671,279 | 6/1987 | Hill ................................. 227/175 |
| 4,688,555 | 8/1987 | Wardle . |
| 4,691,853 | 9/1987 | Storace . |
| 4,706,655 | 11/1987 | Krauter . |
| 4,719,917 | 1/1988 | Barrows et al. . |
| 4,728,020 | 3/1988 | Green et al. . |
| 4,747,531 | 5/1988 | Brinkerhoff et al. . |
| 4,763,669 | 8/1988 | Jaeger . |
| 4,784,137 | 11/1988 | Kulik et al. . |
| 4,787,387 | 11/1988 | Burbank, III et al. . |
| 4,789,090 | 12/1988 | Blake, III . |
| 4,802,478 | 2/1989 | Powell . |
| 4,807,628 | 2/1989 | Peters et al. . |
| 4,811,886 | 3/1989 | Murray . |
| 4,821,939 | 4/1989 | Green . |
| 4,821,942 | 4/1989 | Richards et al. . |
| 4,838,884 | 6/1989 | Dumican et al. . |
| 4,841,888 | 6/1989 | Mills et al. . |
| 4,872,456 | 10/1989 | Hasson . |
| 4,874,122 | 10/1989 | Froelich et al. ................................. 227/19 |
| 4,880,015 | 11/1989 | Nierman . |
| 4,887,756 | 12/1989 | Puchy ................................. 227/19 |
| 4,899,745 | 2/1990 | Laboureau et al. . |
| 4,919,112 | 4/1990 | Siegmund . |
| 4,919,152 | 4/1990 | Ger . |
| 4,919,320 | 4/1990 | Storace . |
| 4,934,364 | 6/1990 | Green . |
| 4,944,443 | 7/1990 | Oddsen et al. . |
| 4,951,861 | 8/1990 | Schulze et al. . |
| 4,978,049 | 12/1990 | Green . |
| 4,997,436 | 3/1991 | Oberlander . |
| 5,002,551 | 3/1991 | Linsky et al. . |
| 5,015,249 | 5/1991 | Nakao et al. . |
| 5,040,715 | 8/1991 | Green et al. . |
| 5,042,707 | 8/1991 | Taheri . |
| 5,047,038 | 9/1991 | Peters et al. . |
| 5,049,152 | 9/1991 | Simon et al. . |
| 5,049,153 | 9/1991 | Nakao et al. . |
| 5,071,430 | 12/1991 | de Salis et al. . |
| 5,084,057 | 1/1992 | Green et al. . |
| 5,100,420 | 3/1992 | Green et al. . |
| 5,125,553 | 6/1992 | Oddsen et al. . |
| 5,147,373 | 9/1992 | Ferzli . |
| 5,156,609 | 10/1992 | Nakao ................................. 227/179 |
| 5,161,725 | 11/1992 | Murray et al. ................................. 227/182 |
| 5,161,725 | 11/1992 | Murray et al. . |
| 5,163,945 | 11/1992 | Ortiz et al. . |
| 5,174,487 | 12/1992 | Rothfuss et al. . |
| 5,220,928 | 6/1993 | Oddsen et al. ................................. 227/175 |
| 5,222,975 | 6/1993 | Crainich . |
| 5,240,163 | 8/1993 | Stein et al. . |
| 5,246,156 | 9/1993 | Rothfuss et al. . |
| 5,246,450 | 9/1993 | Thornton et al. . |
| 5,251,801 | 10/1993 | Ruckdeschel et al. . |
| 5,381,943 | 1/1995 | Allen et al. ................................. 227/177 |

OTHER PUBLICATIONS

U.S. Patent Appln. Serial No. 08/073,632, filed Jun. 8, 1993, which is a file wrapper continuation of U.S. patent Appln. Serial No. 07/686,795, filed Apr. 17, 1991.

Publication Entitled "A Quick Stapler Tie–Over Fixation For Skin Grafts", by Haim Y. Kaplan, M.D., Ann. Plast. Surg., 22:173, 1989, pp. 173–174.

Publication Entitled "A Rapid and Effective Method of Skin Graft Stabilization in Burned Children", by J. B. Boyd et al., The Hospital For Sick Children, Toronto, Canada, 1982, pp. 400–401.

Publication Entitled "A Simple Bolster Technique For Skin Grafting", by Henry T. Hoffman, M.D. and Michael LaRouere, M.D., Department of Otolaryngology, University of Michigan, Laryngoscope 99, May 1989, pp. 558–559.

Article, Swain, C. P., Mills, T. N. "An Endoscopic Sewing Machine", *Gastrointestinal Endoscopy*, 1986, vol. 32, No. 1, pp. 36–38.

Article, Swain, C. P., Brown, G. J. and Mills, T. N. "An Endoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338–339.

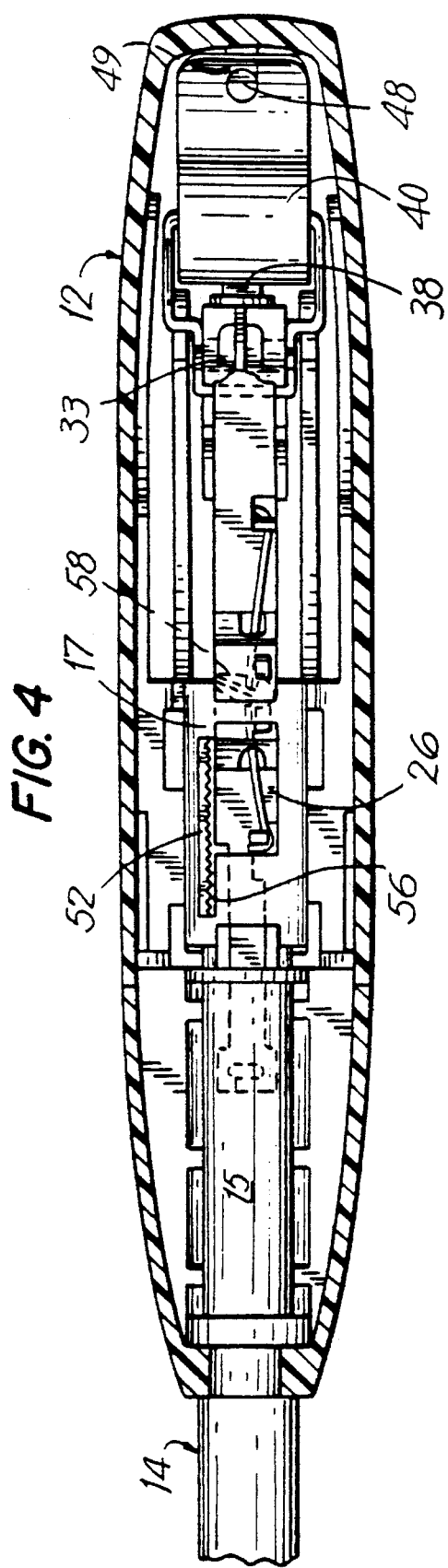
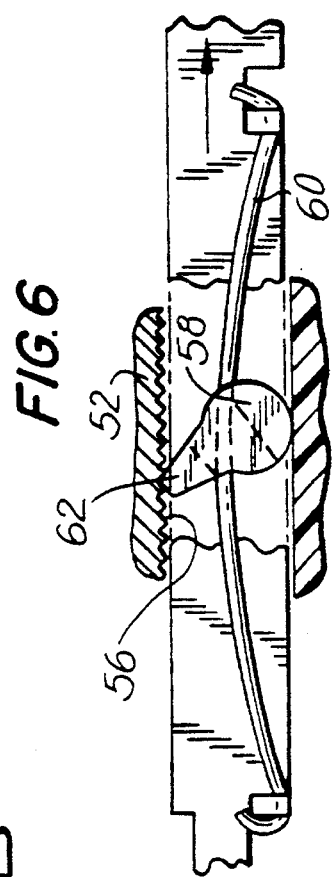
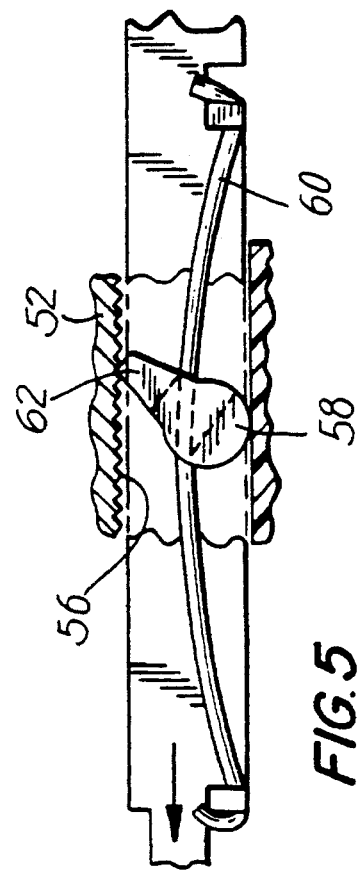
FIG. 4
FIG. 6
FIG. 5

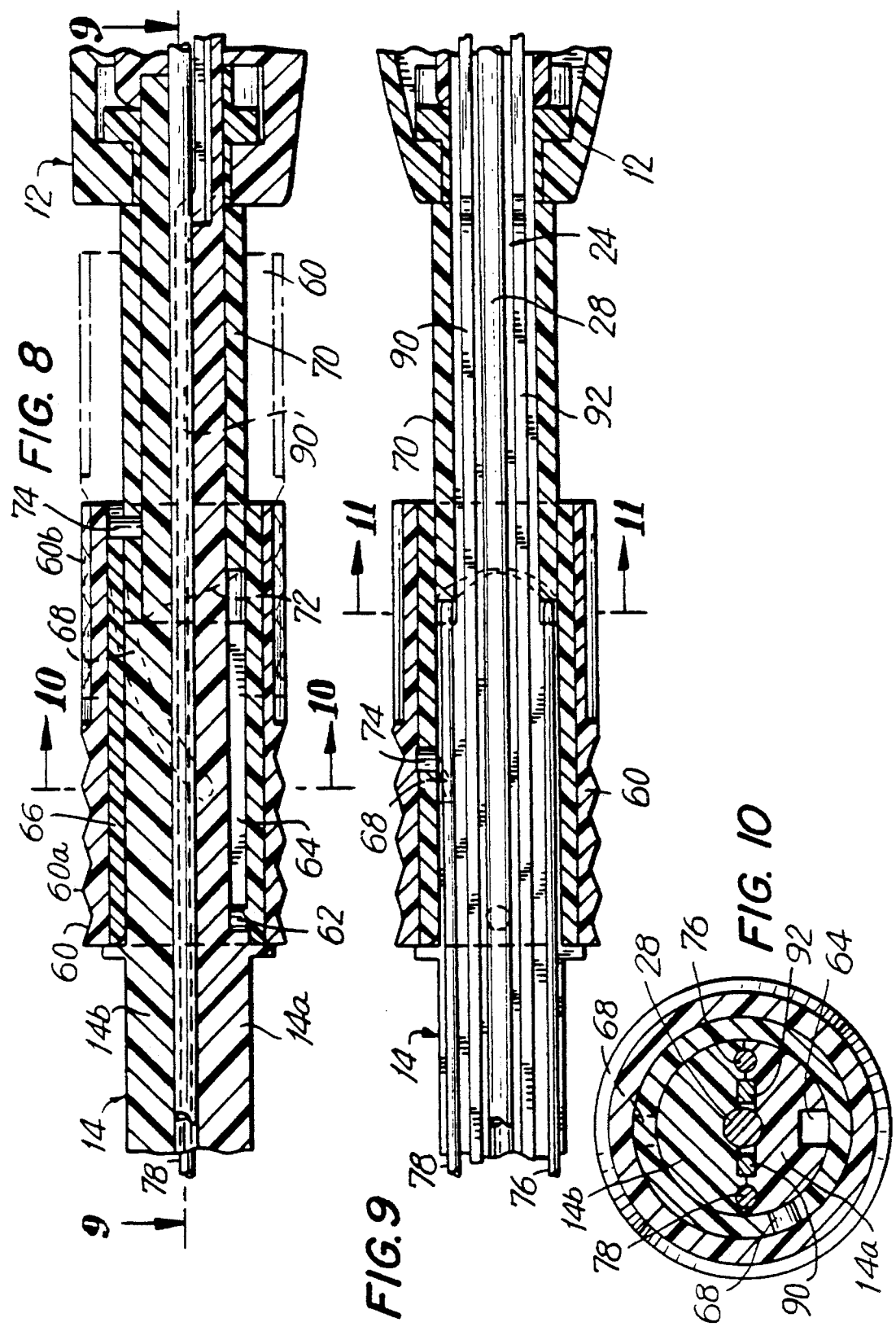

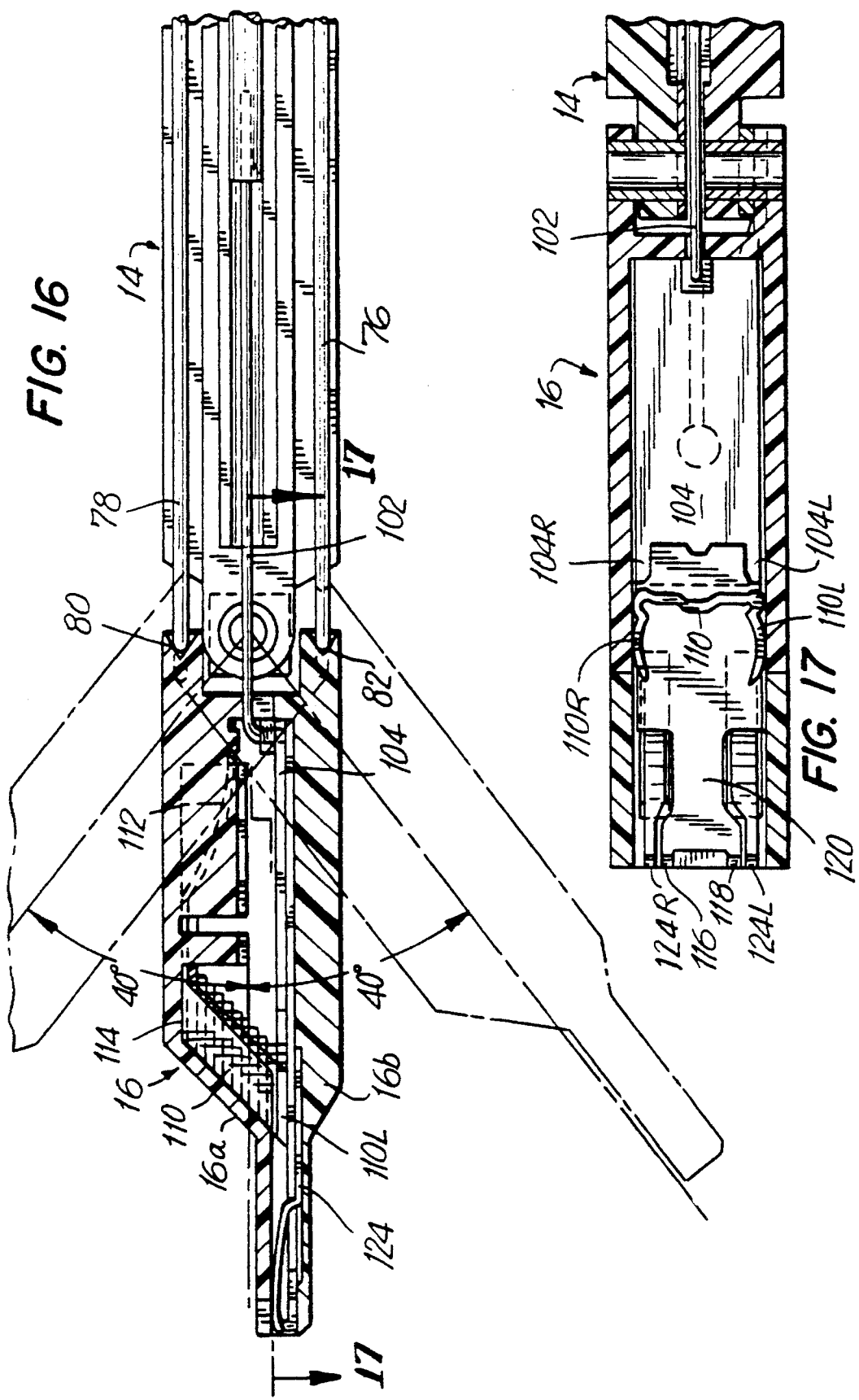

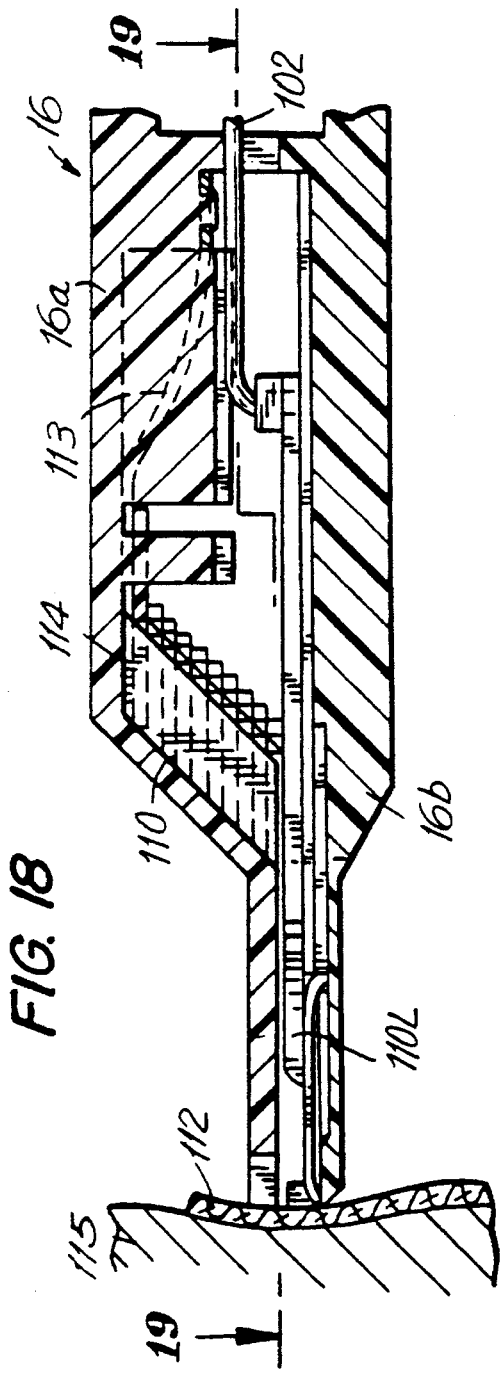
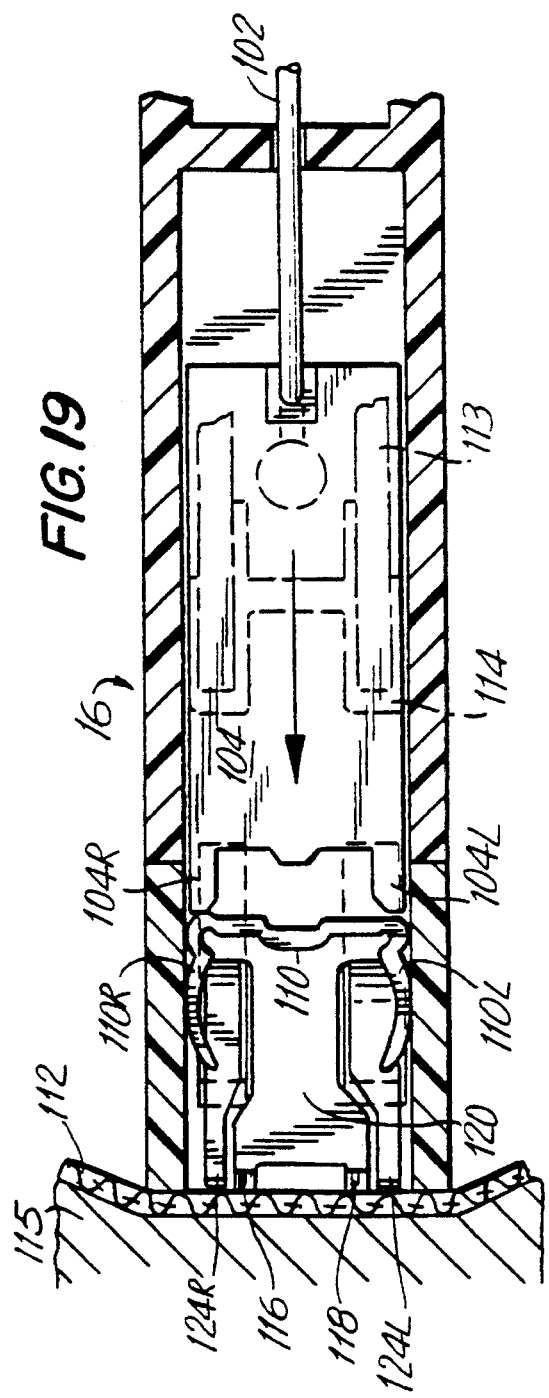

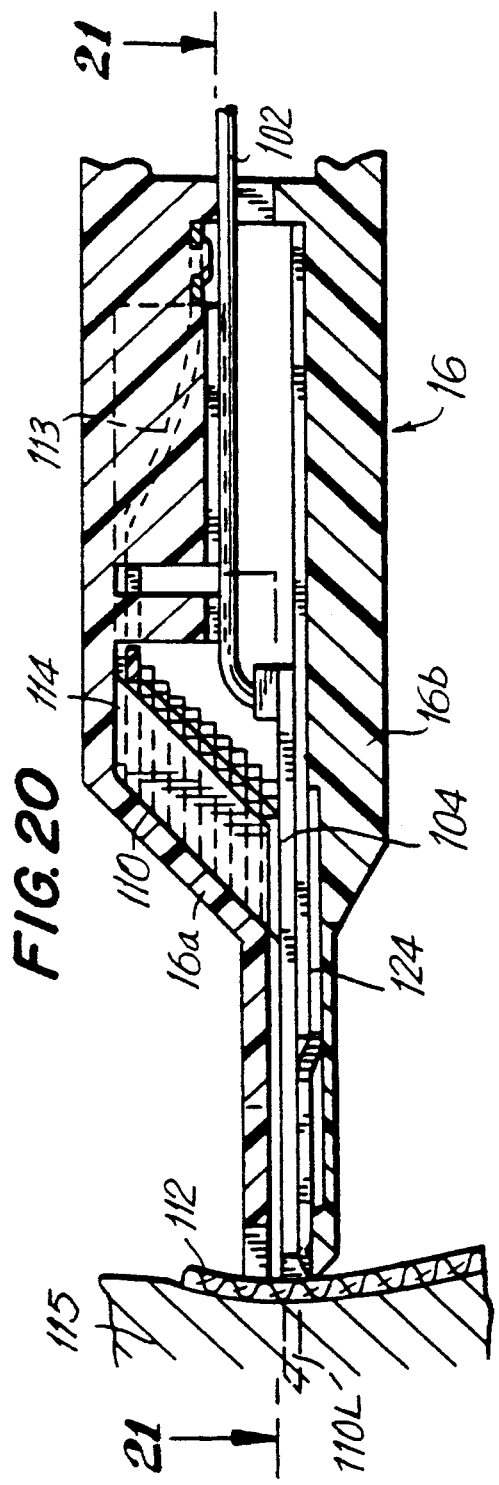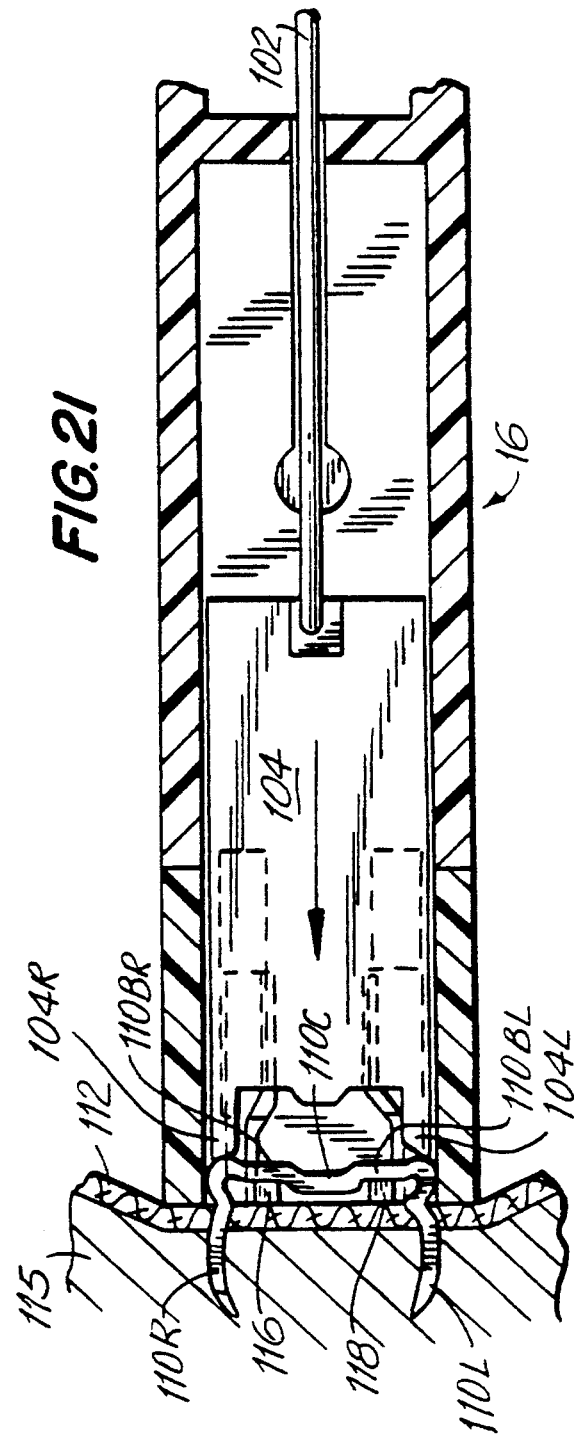

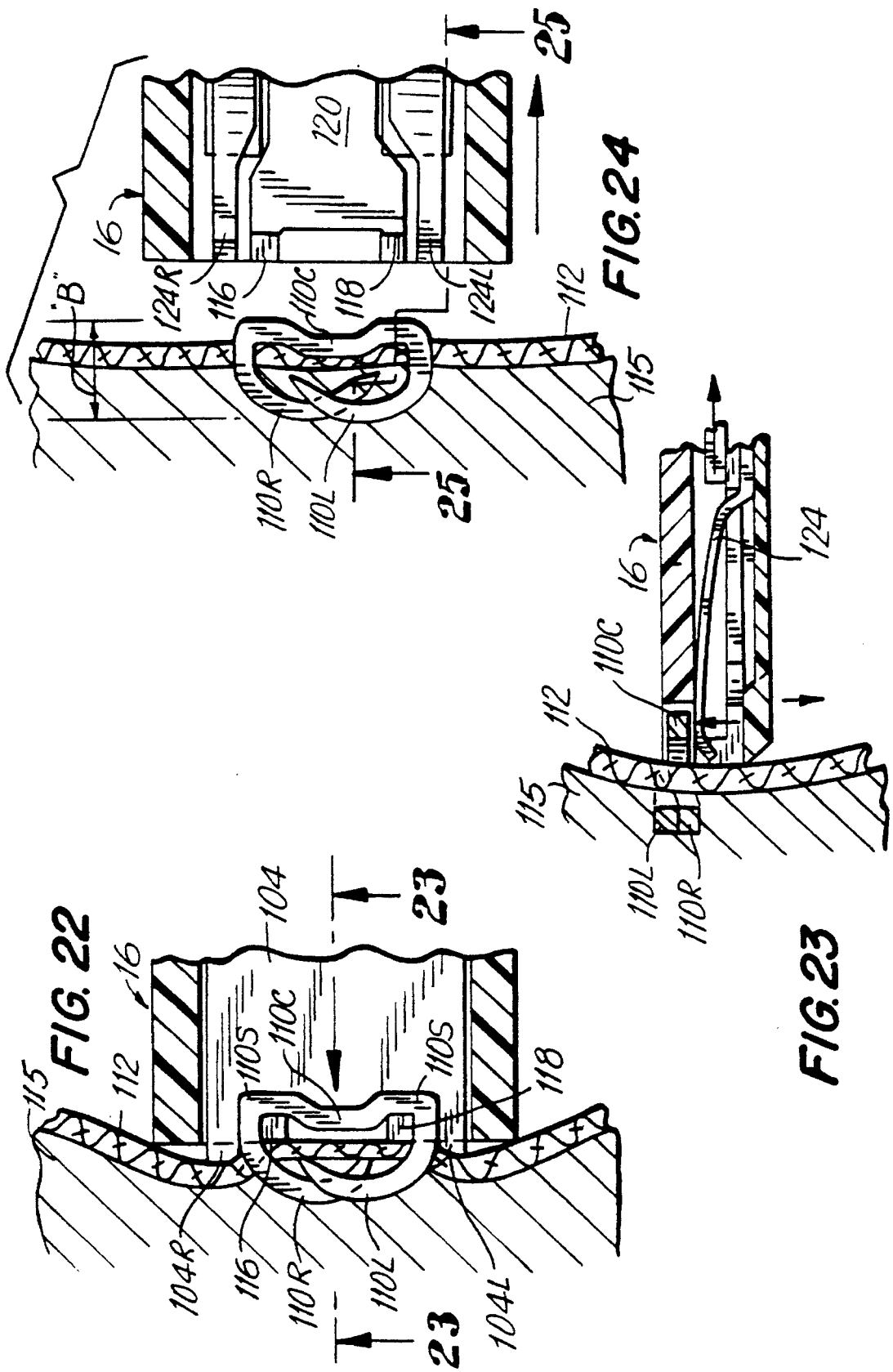

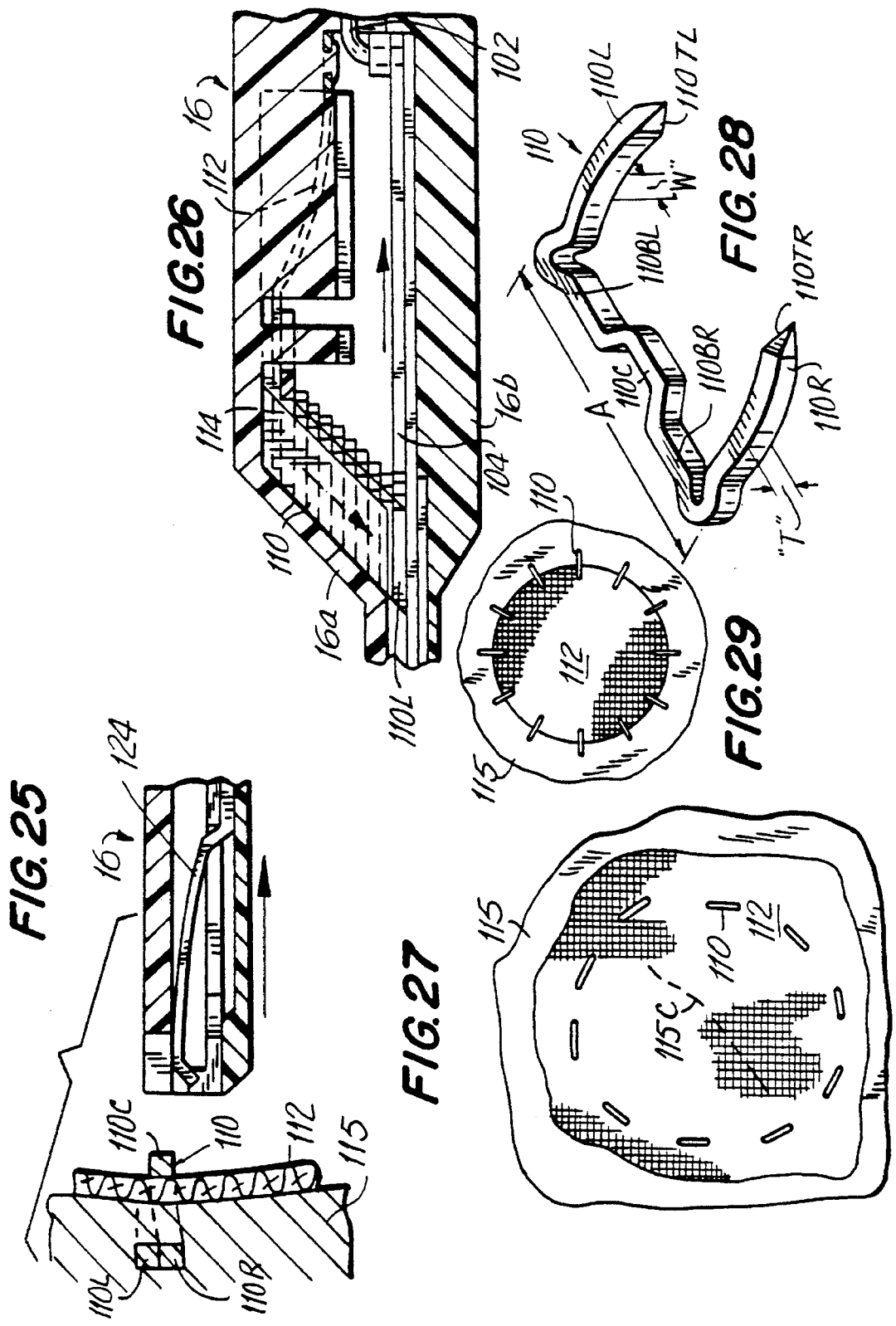

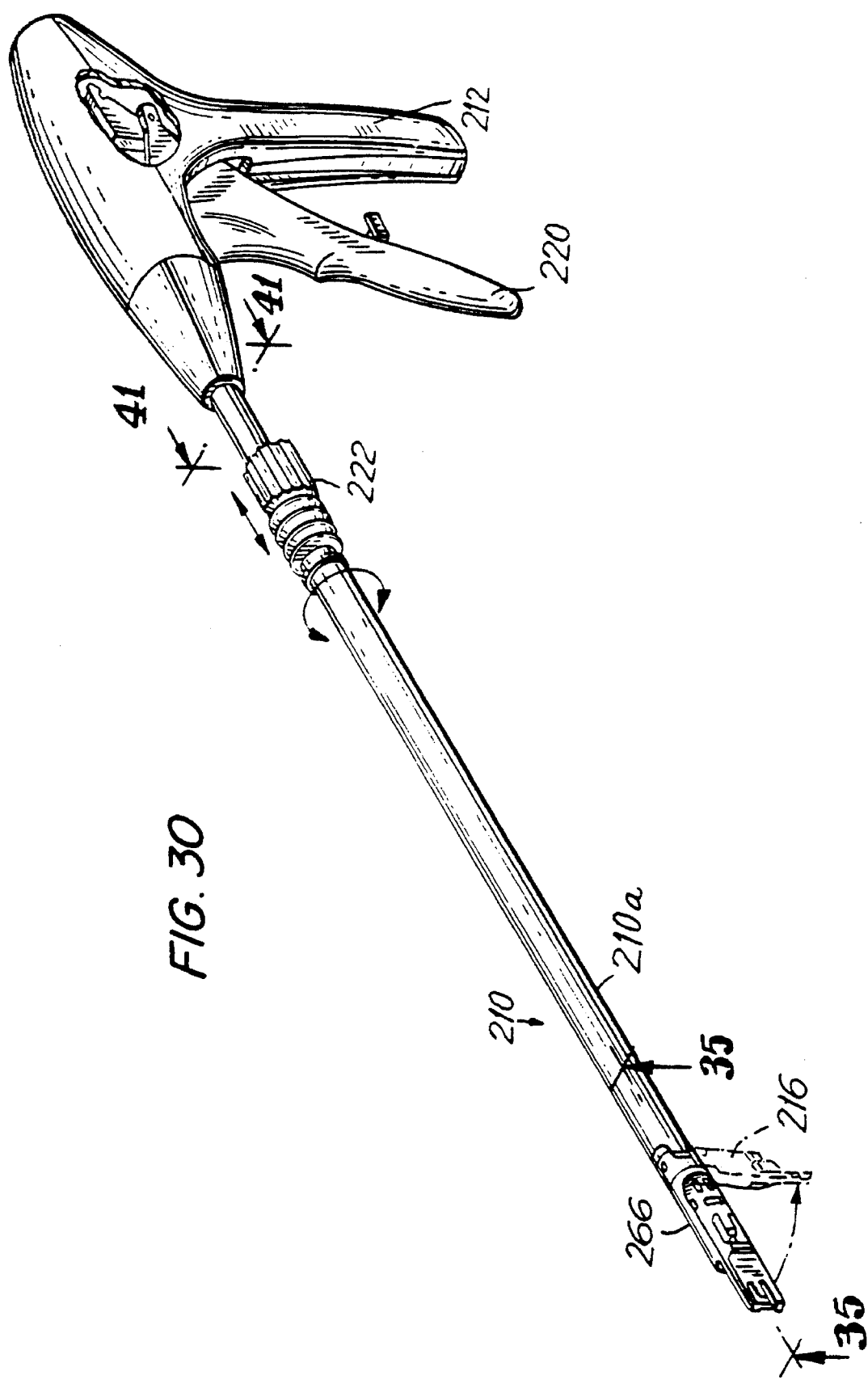

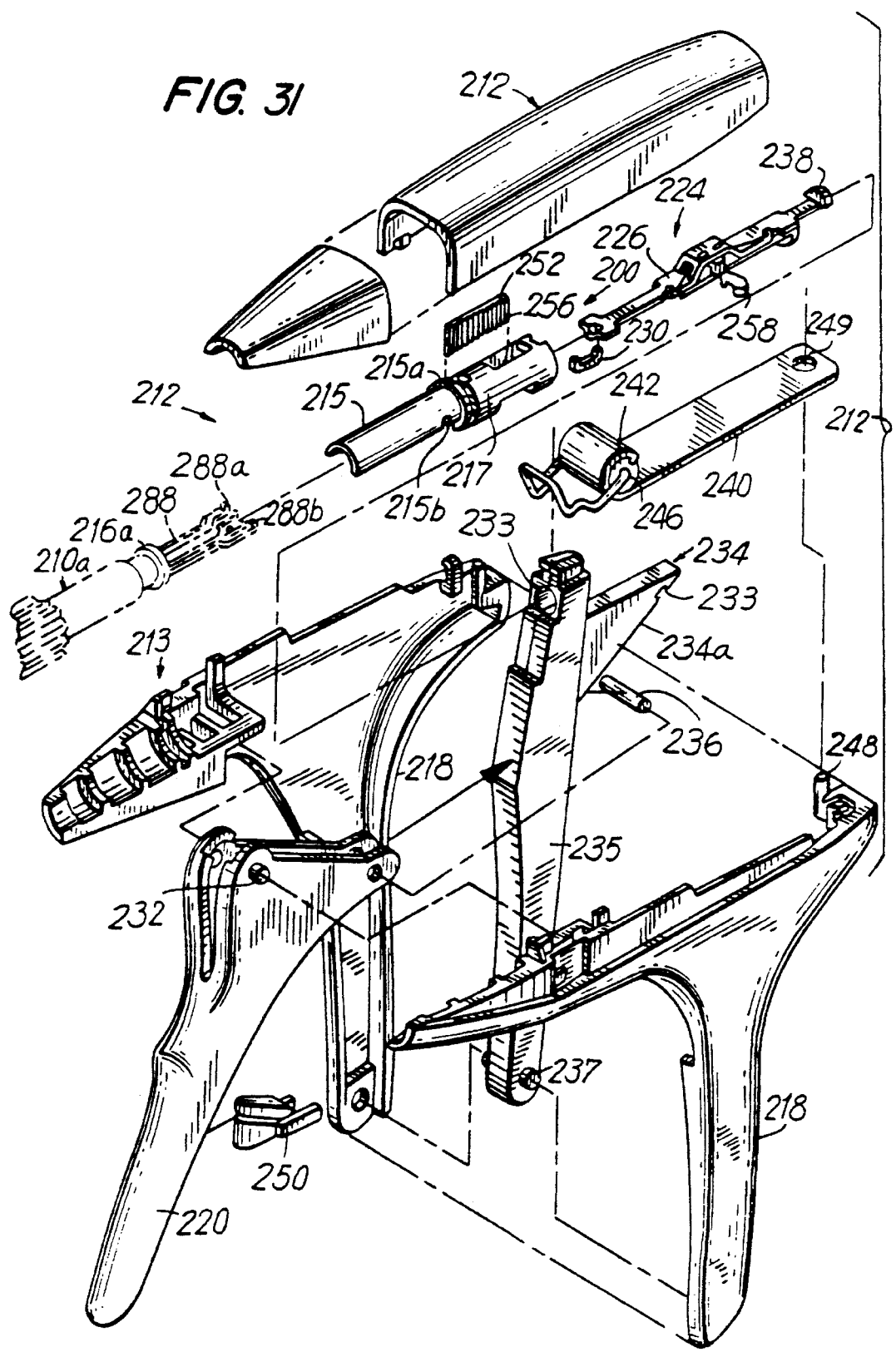

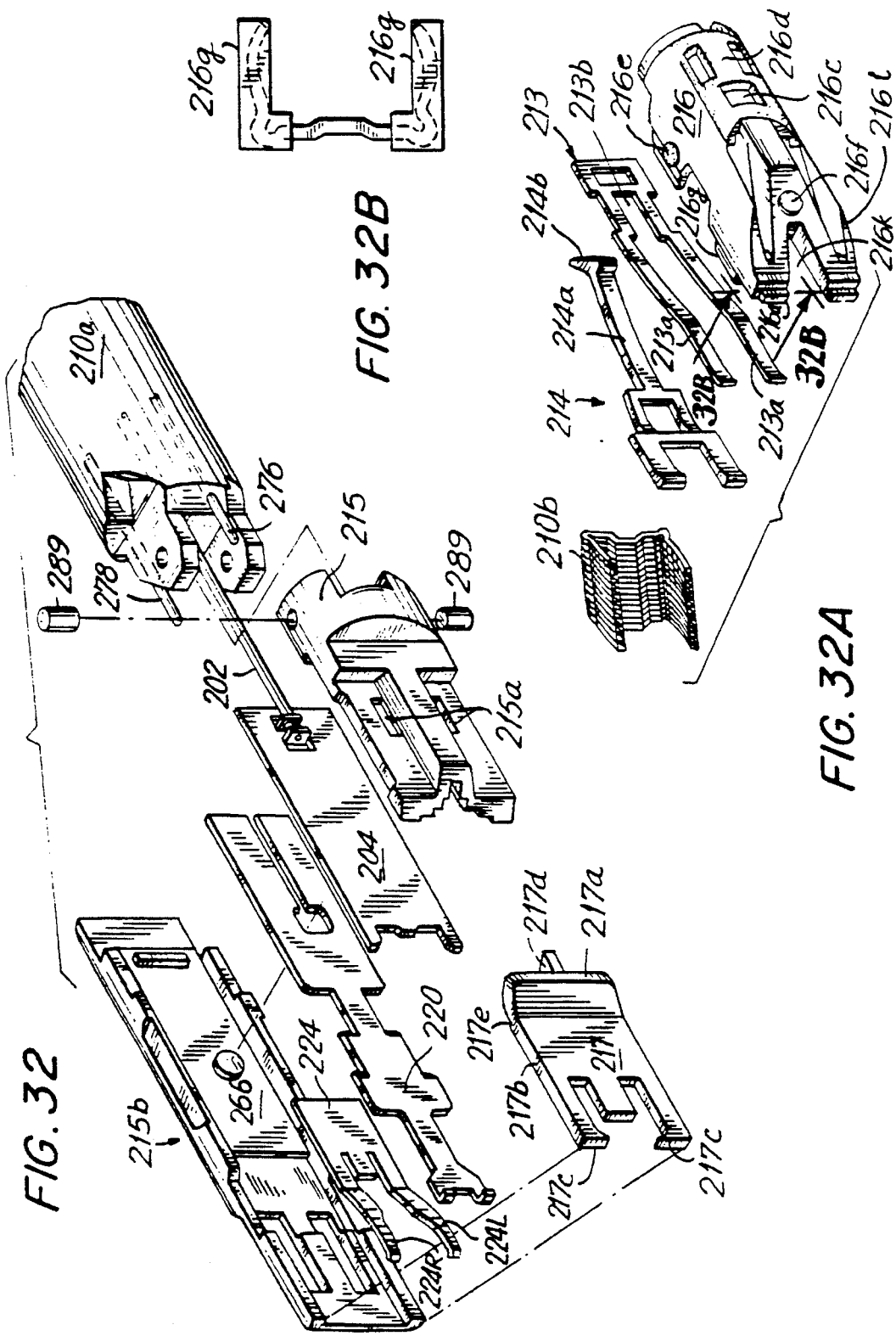

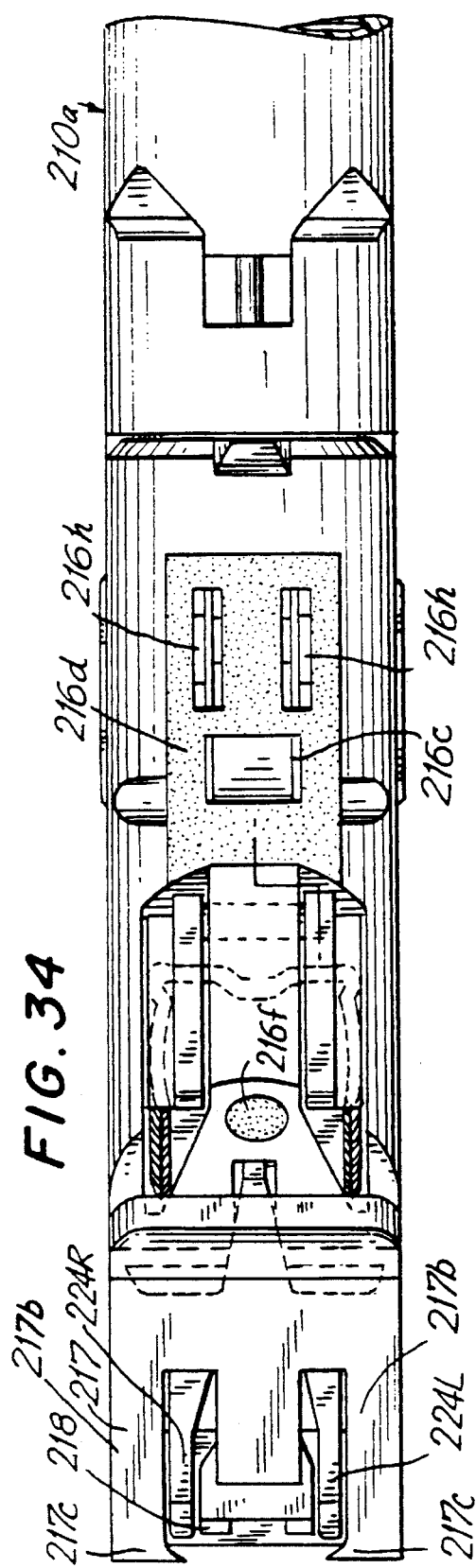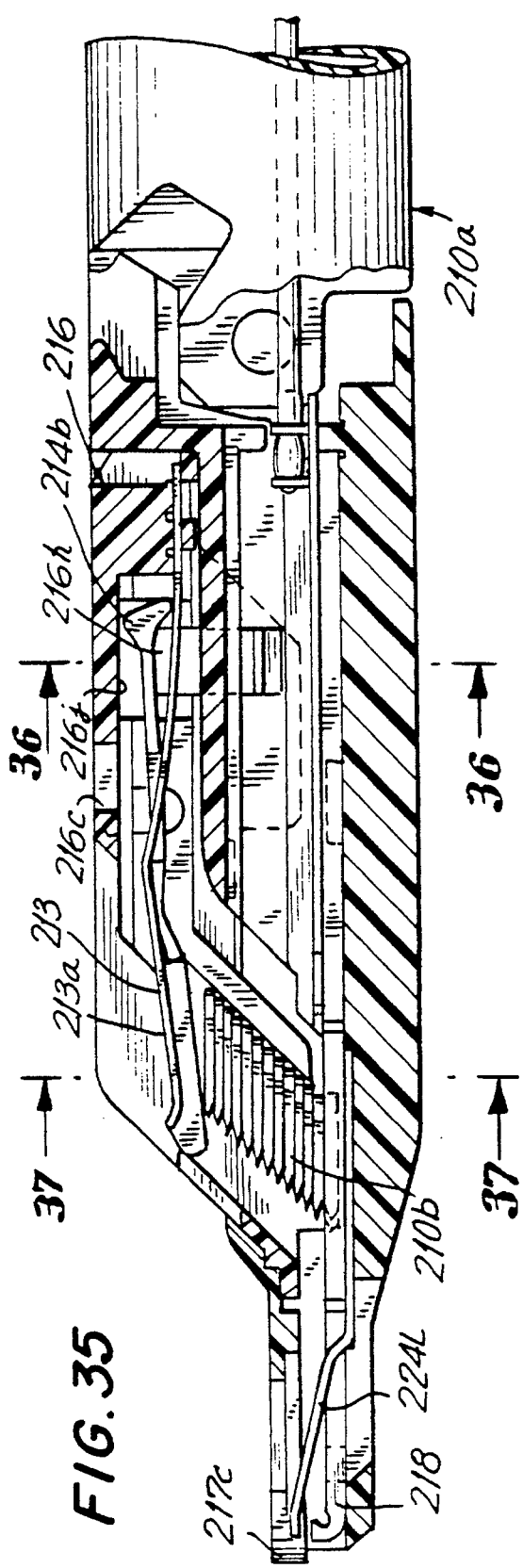

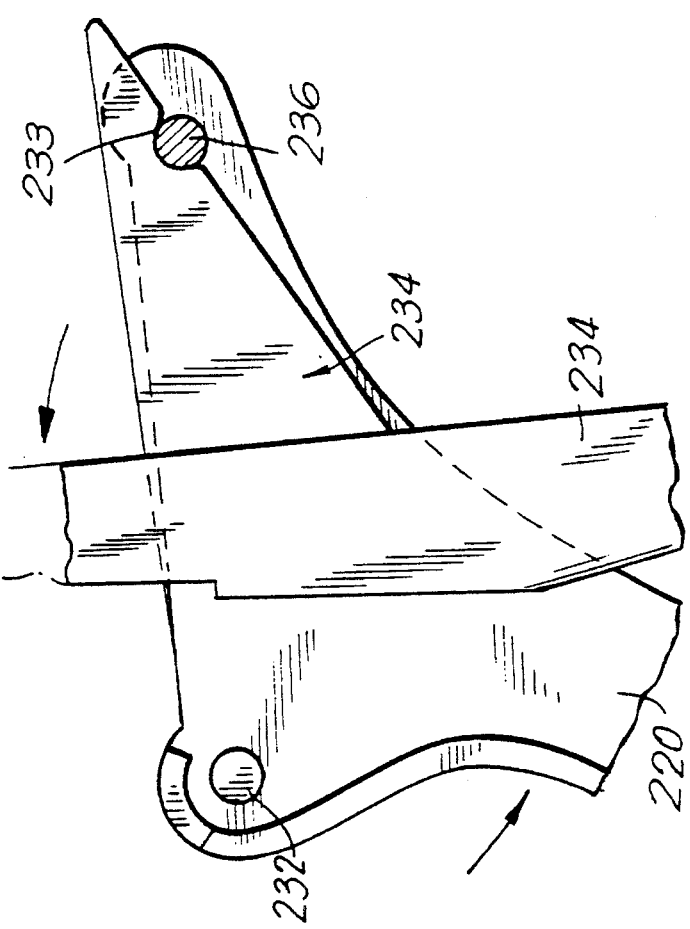
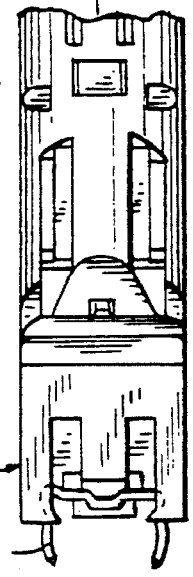
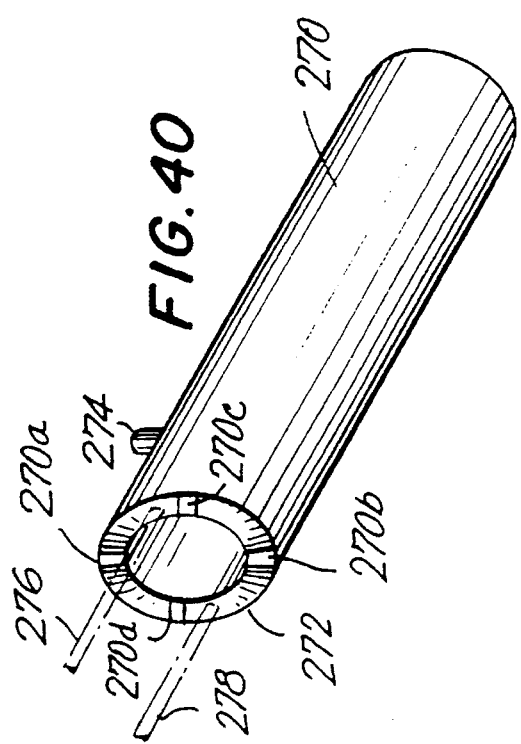

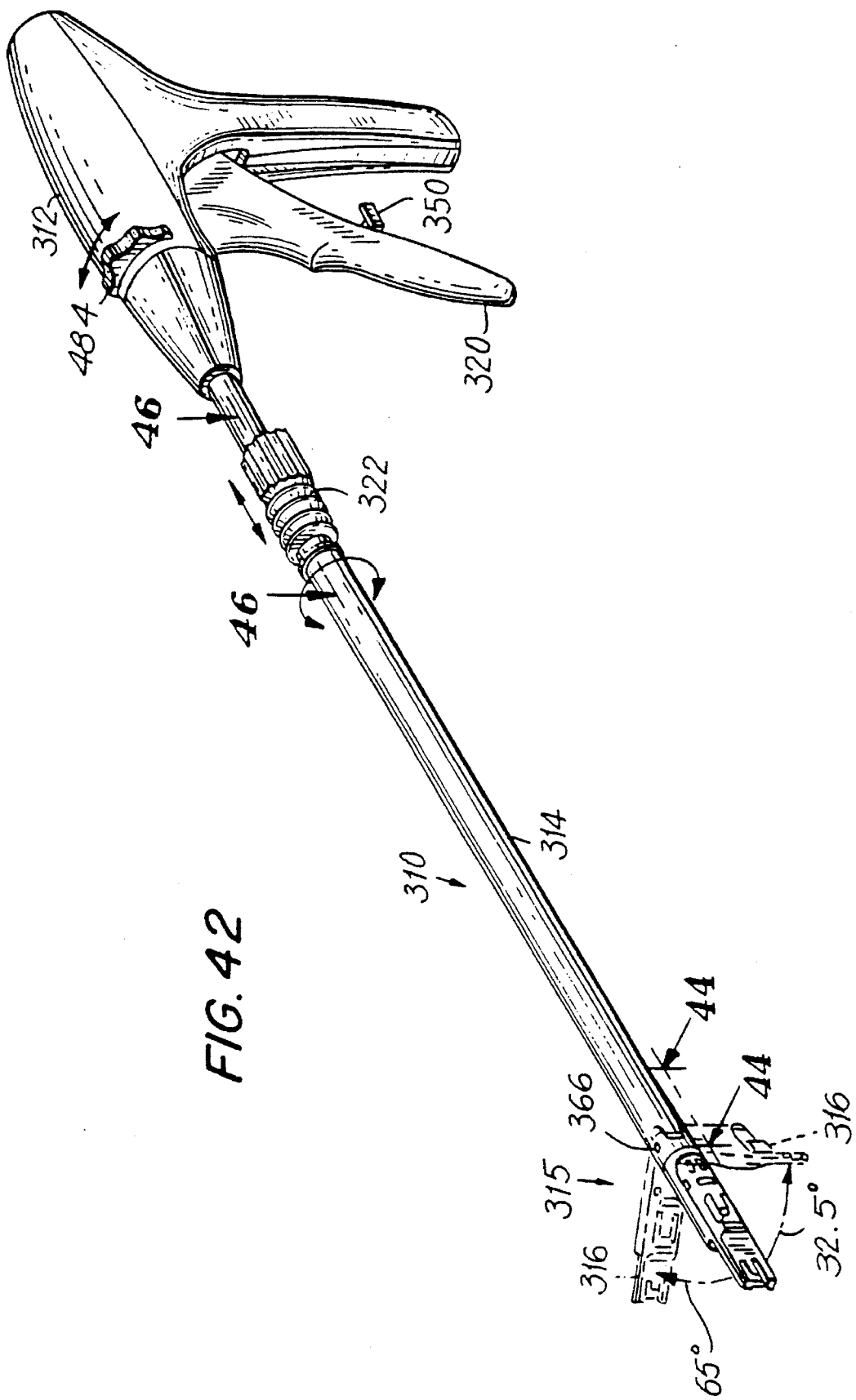

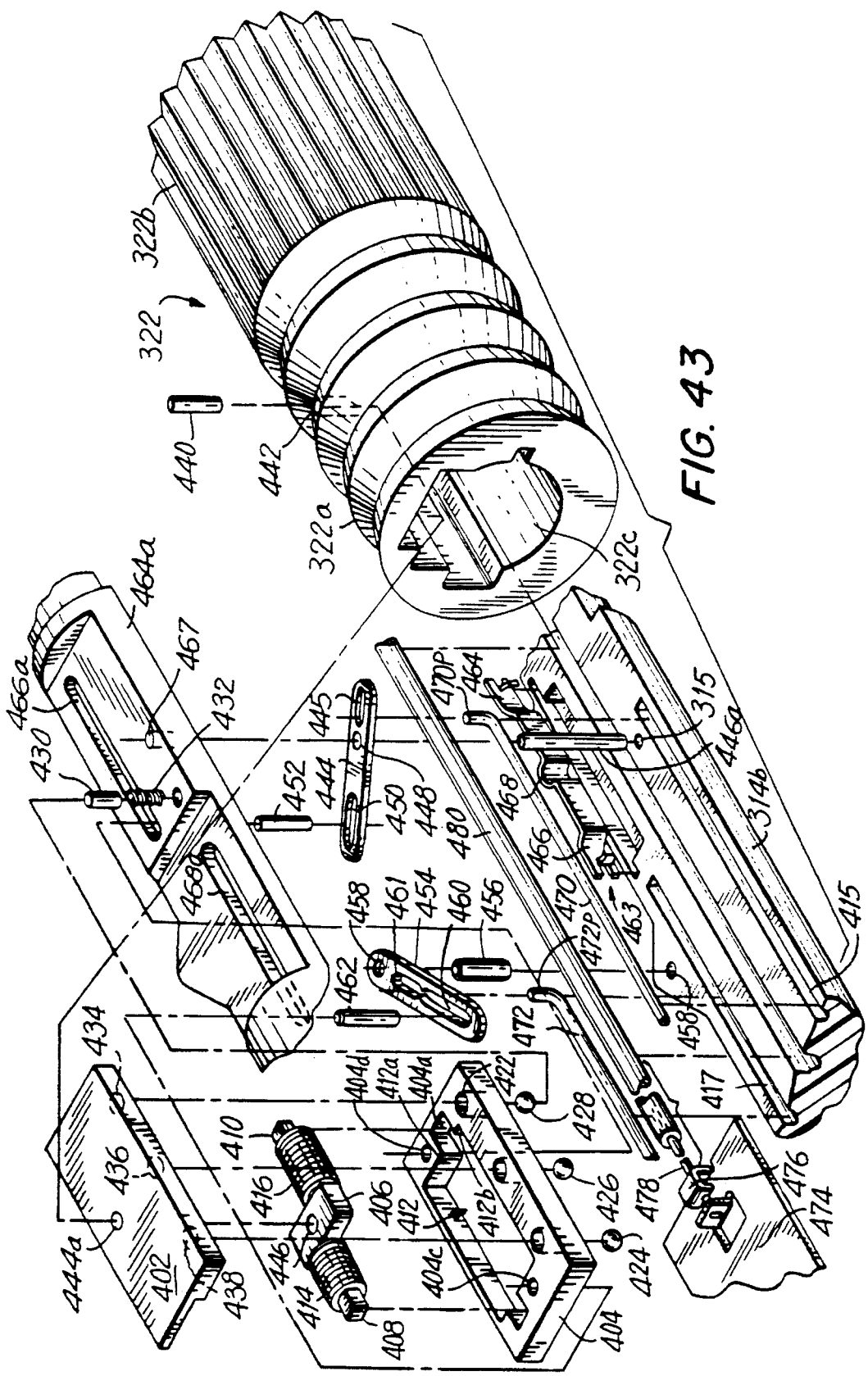

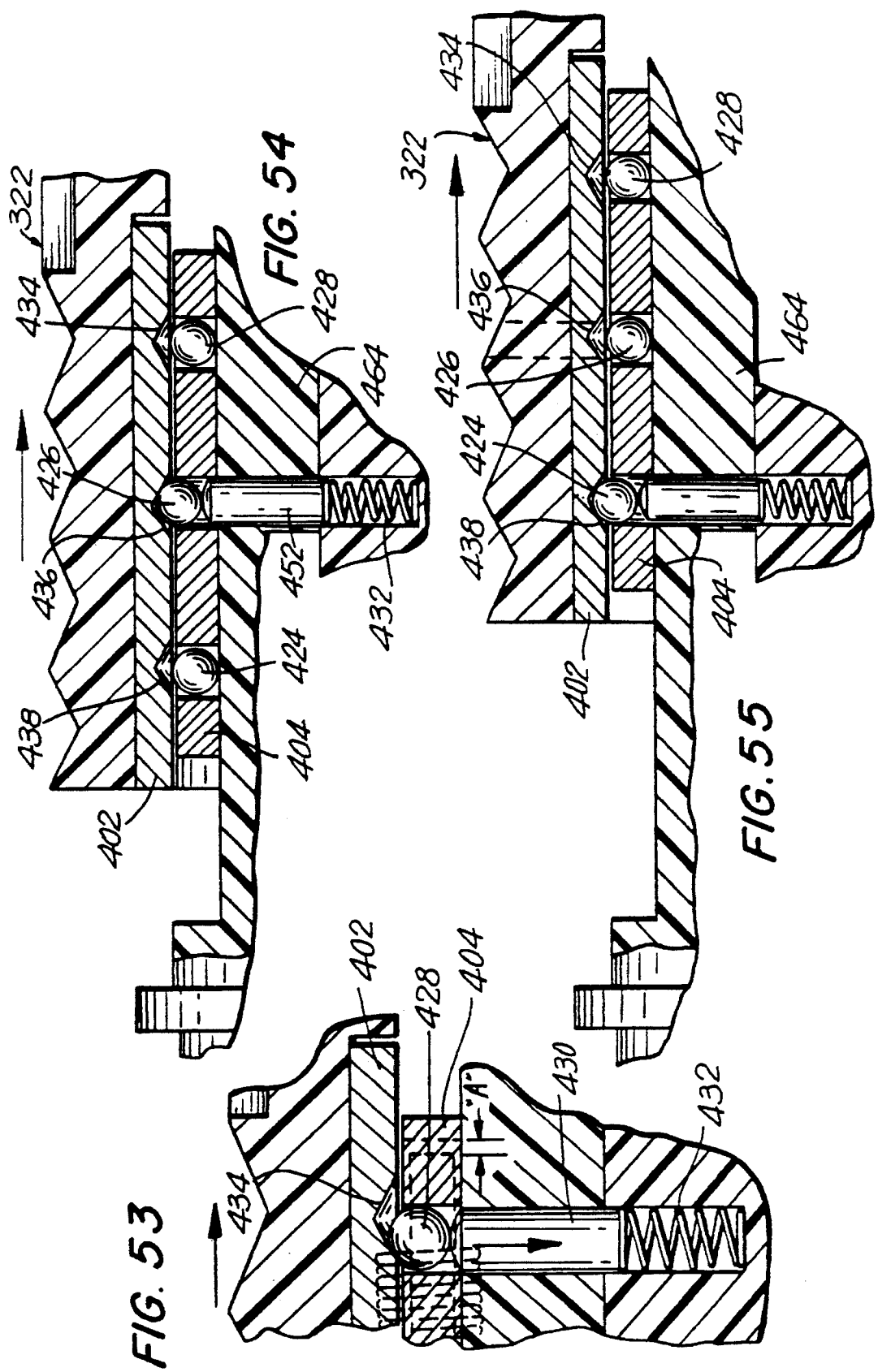

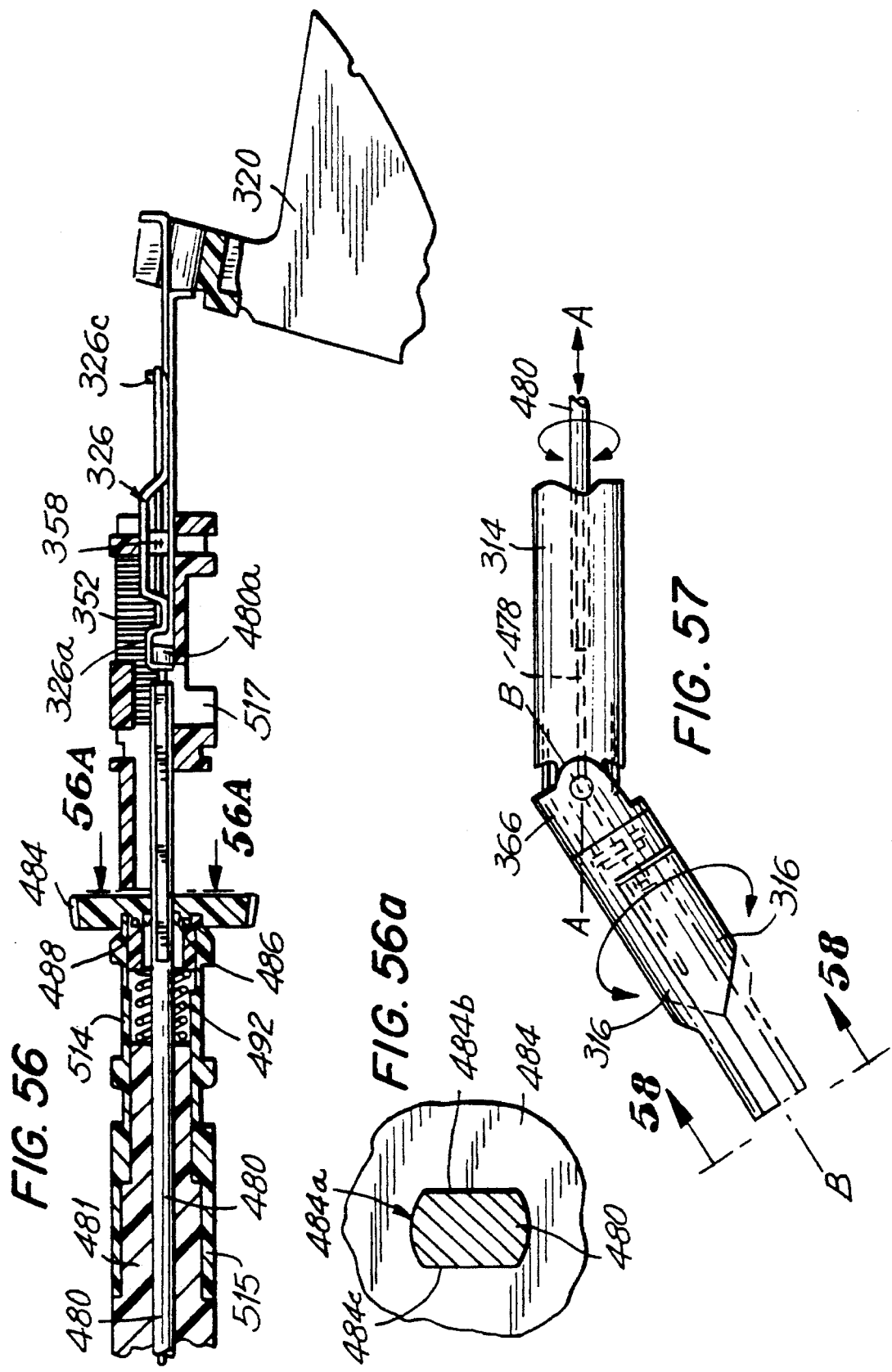

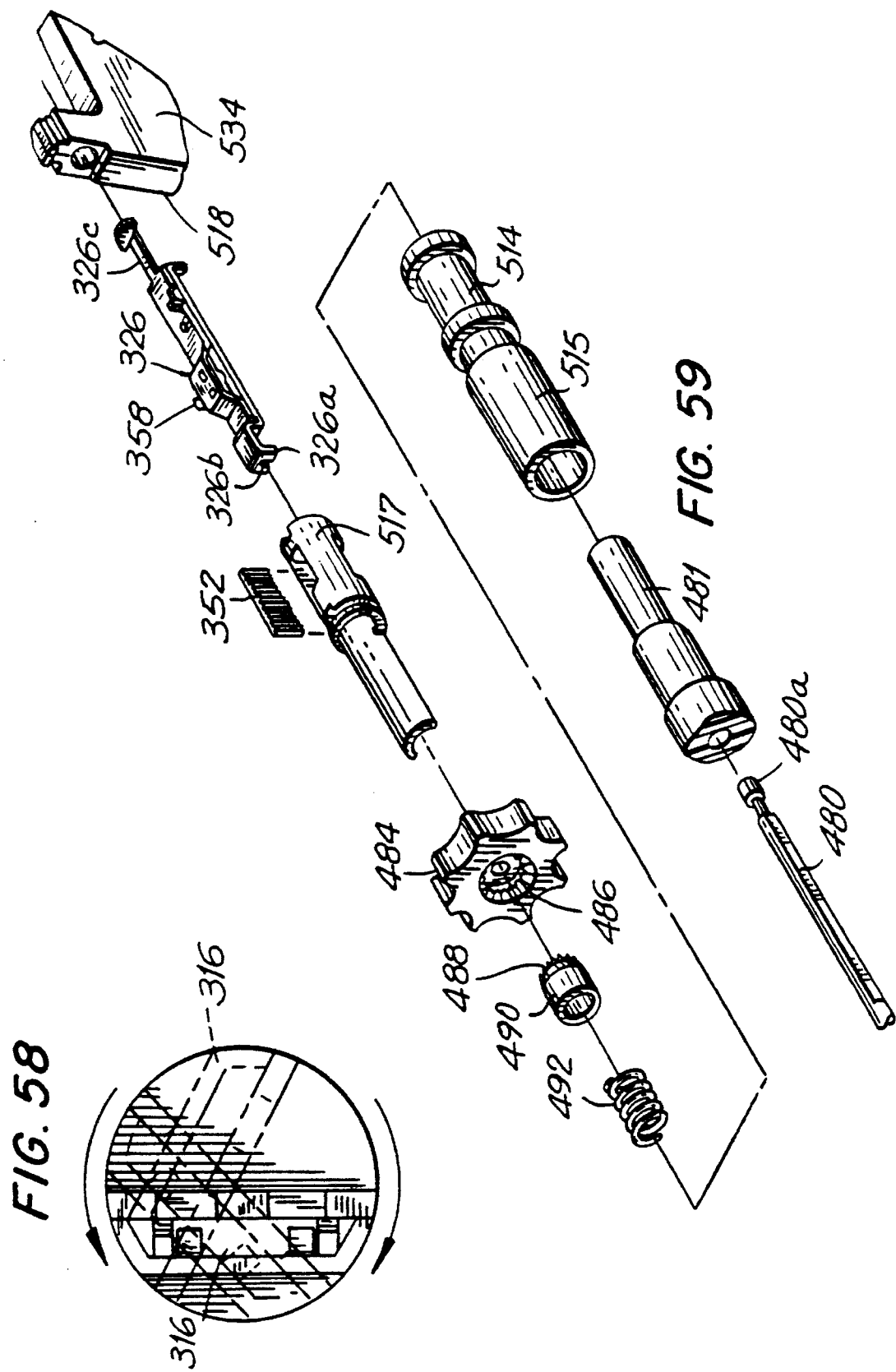

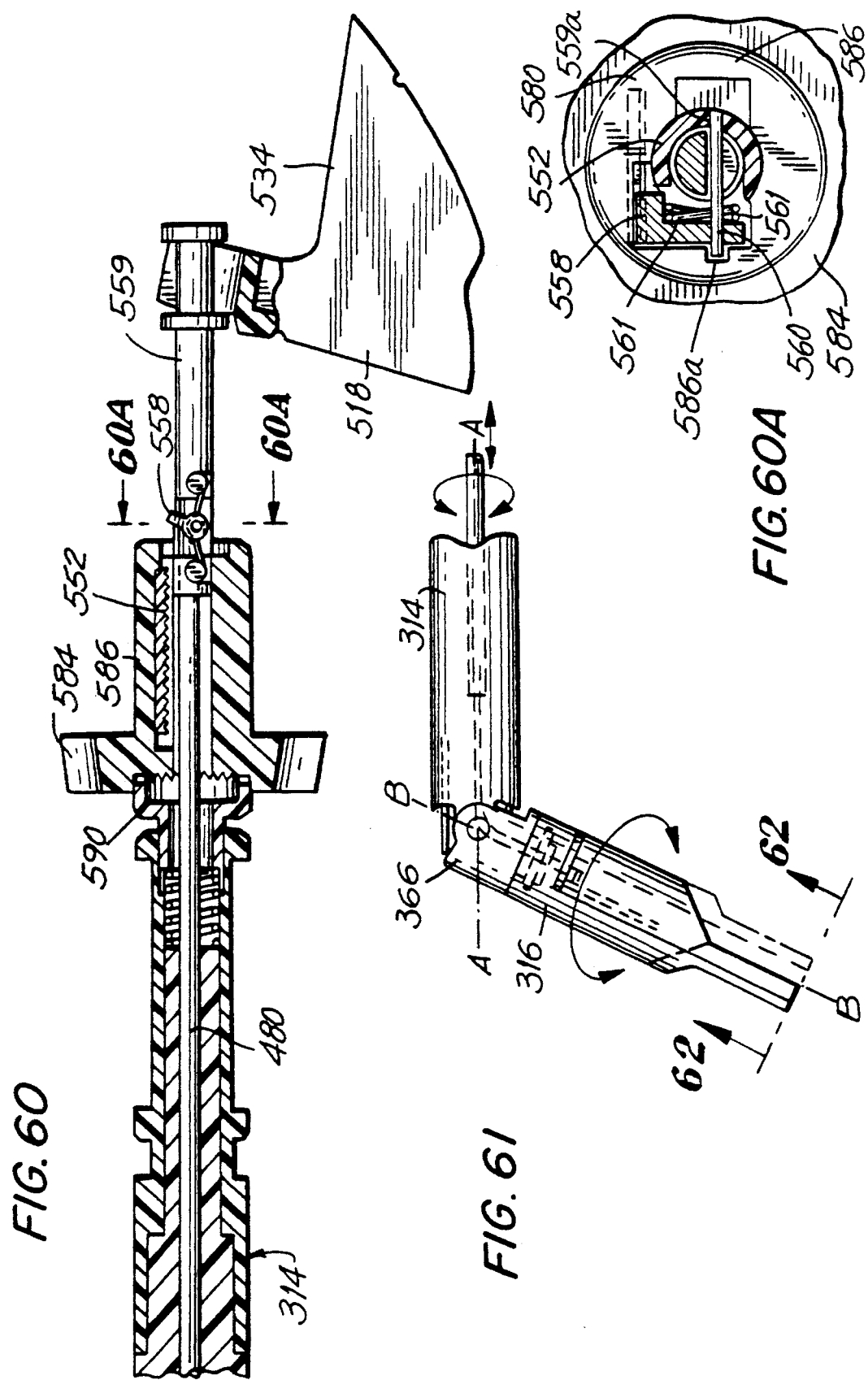

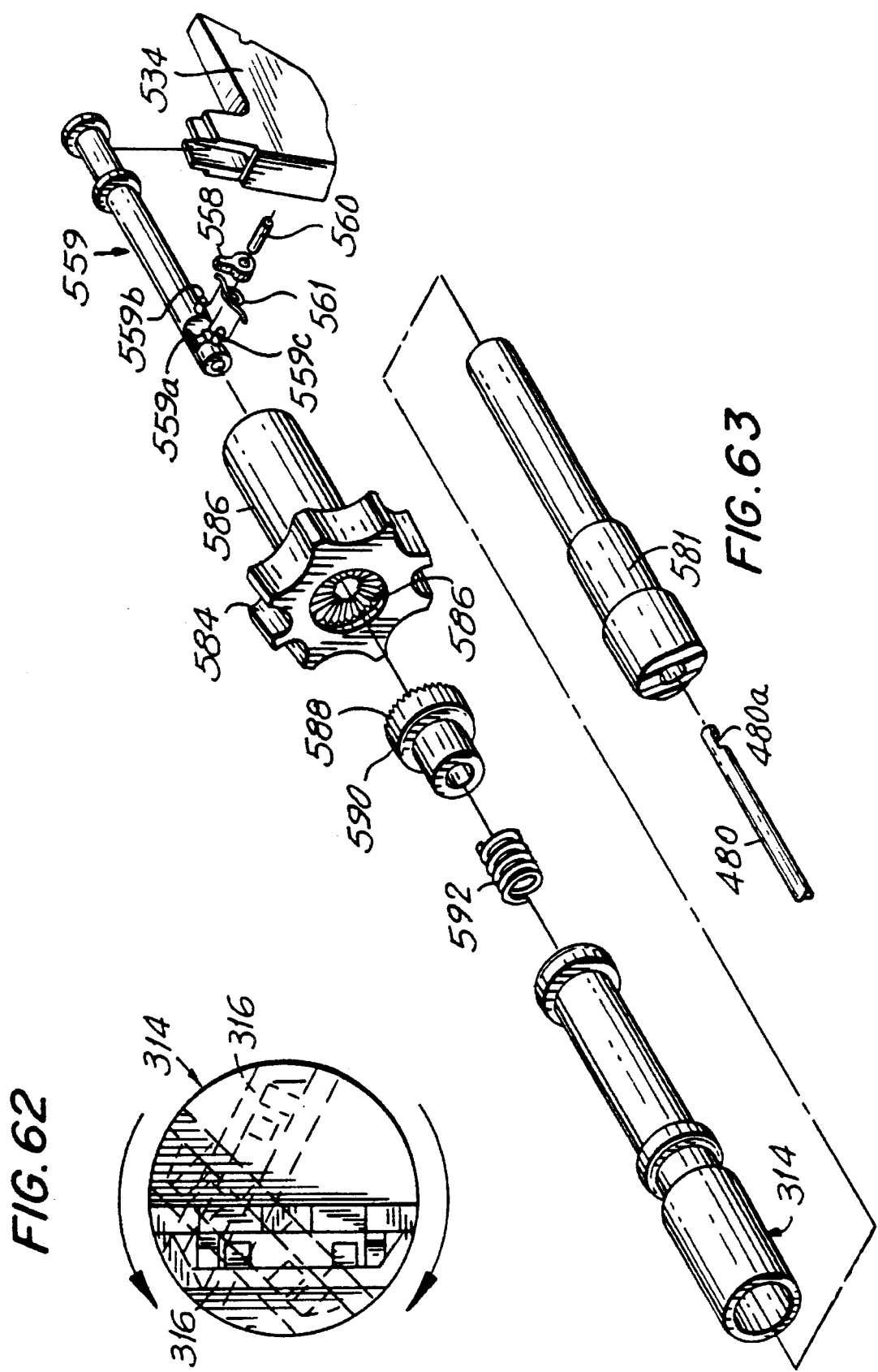

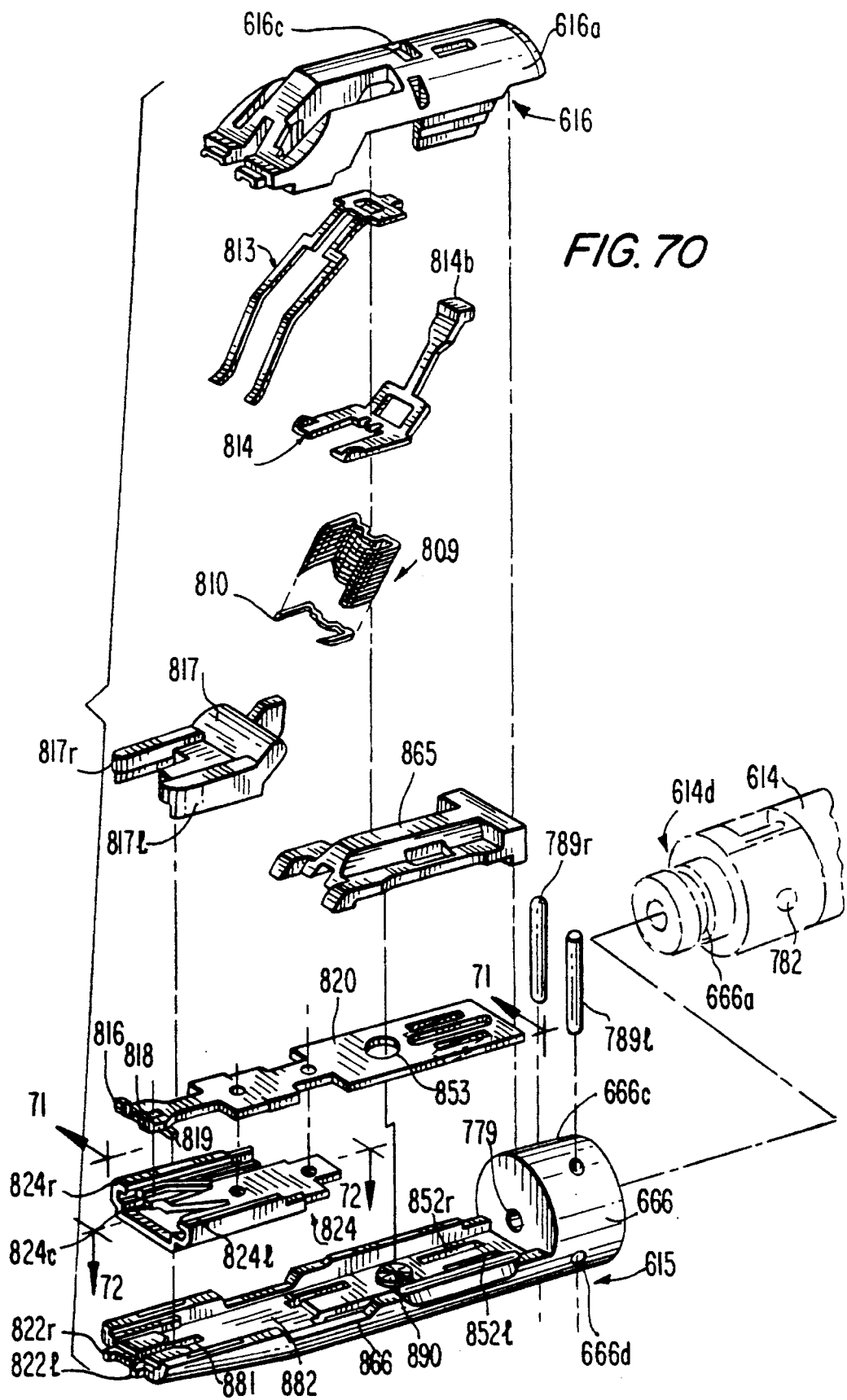

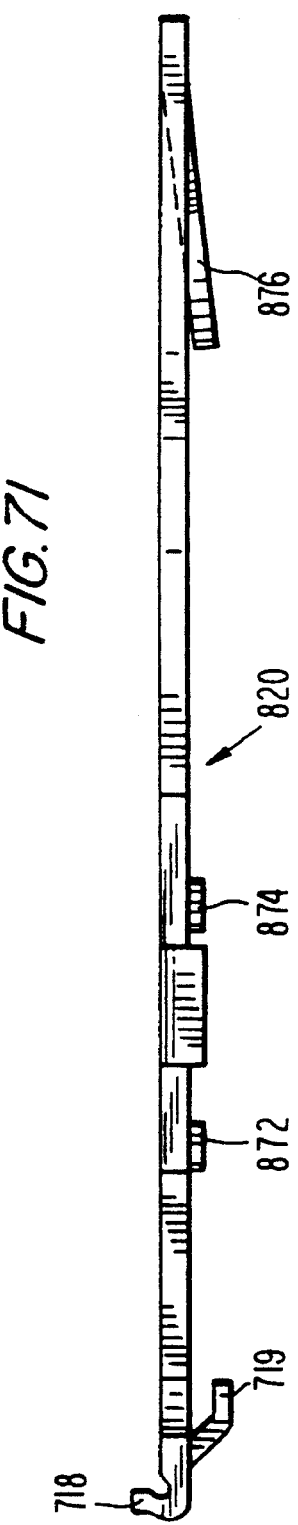
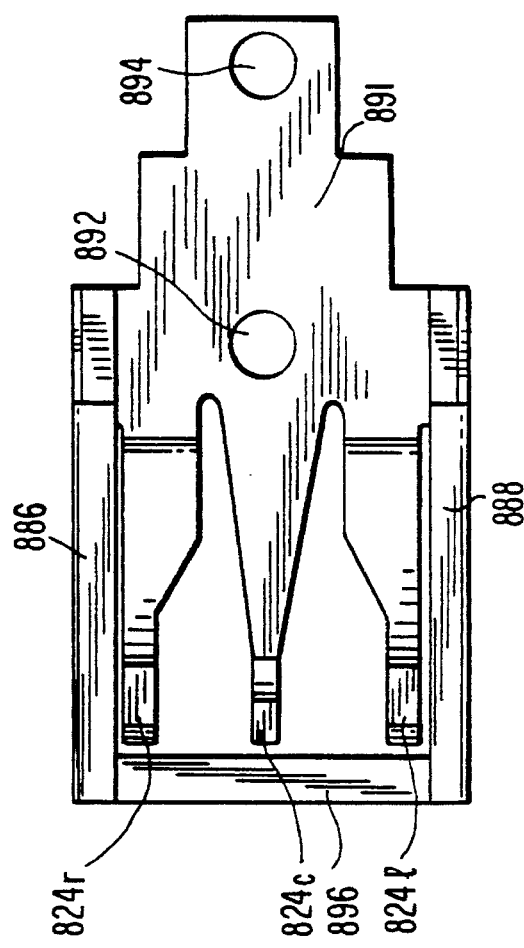

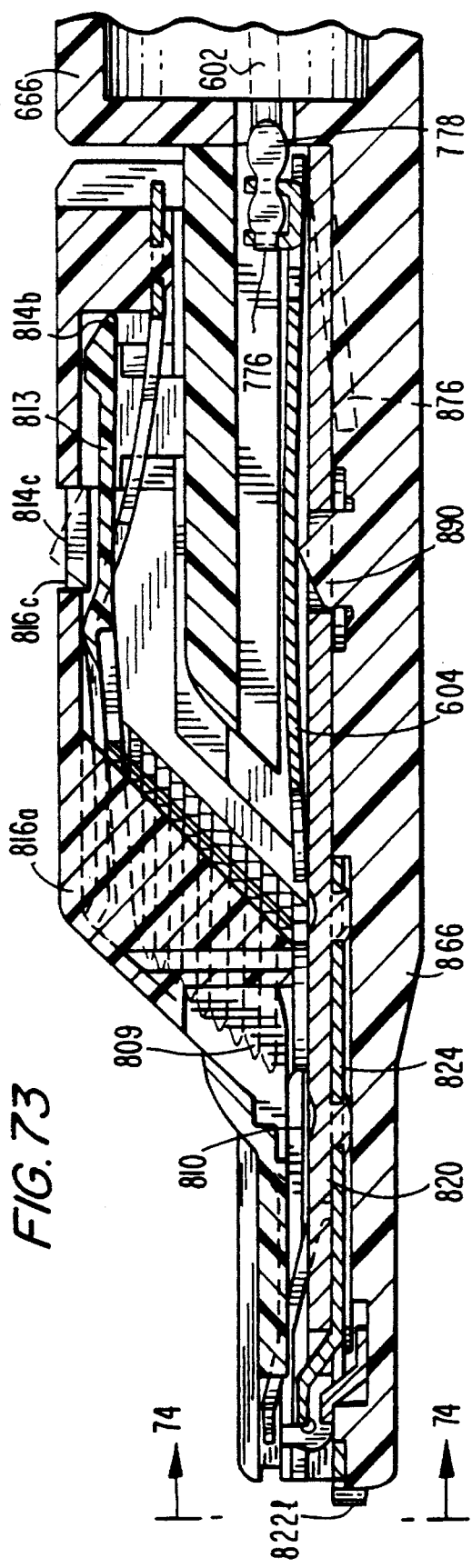
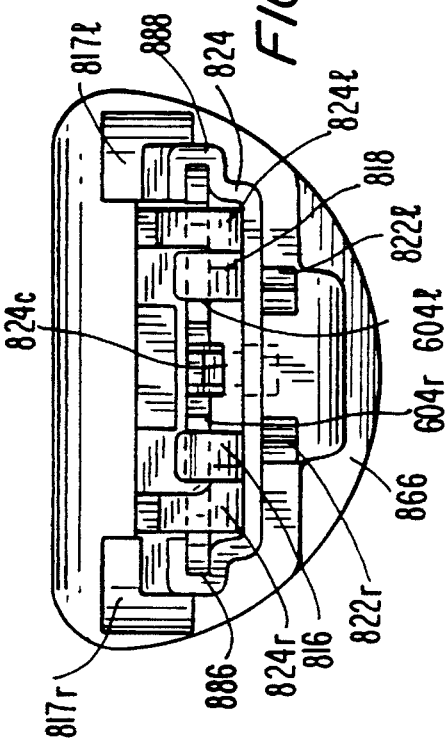
FIG. 73
FIG. 74

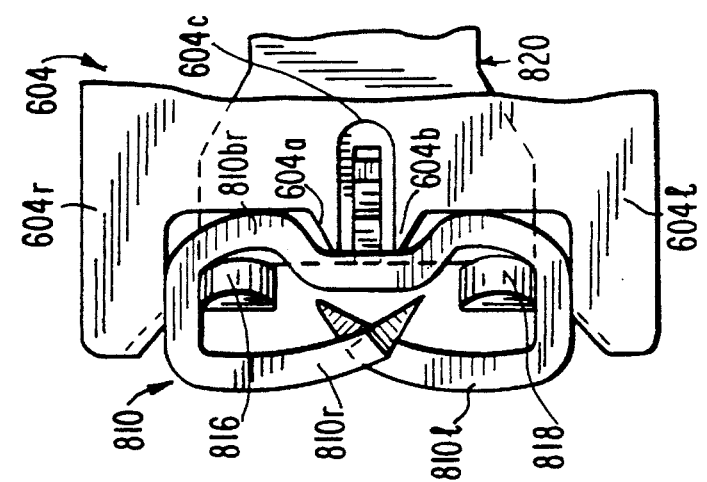
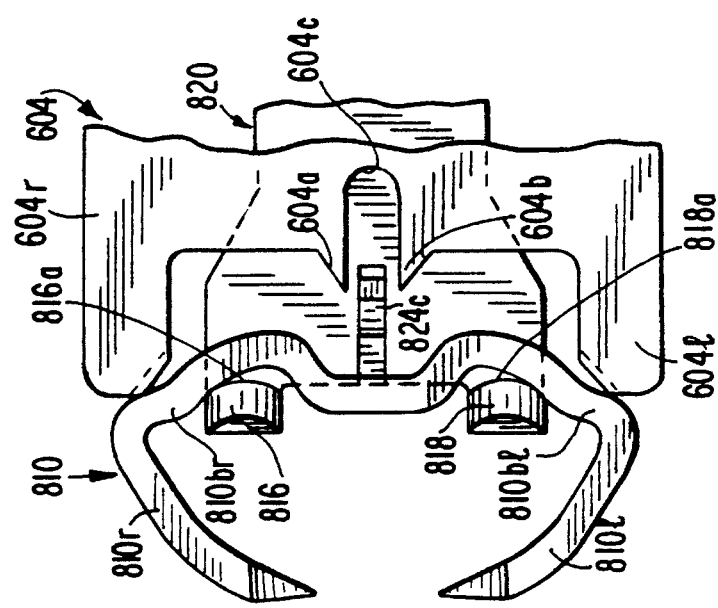
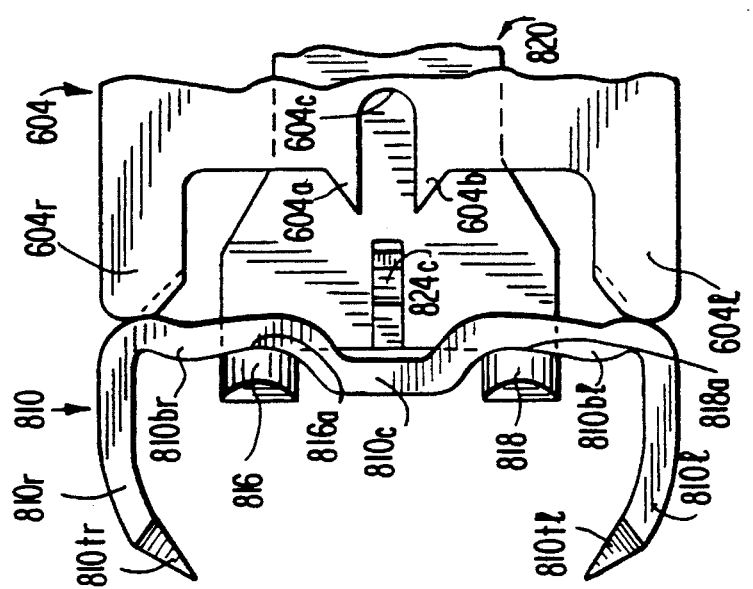

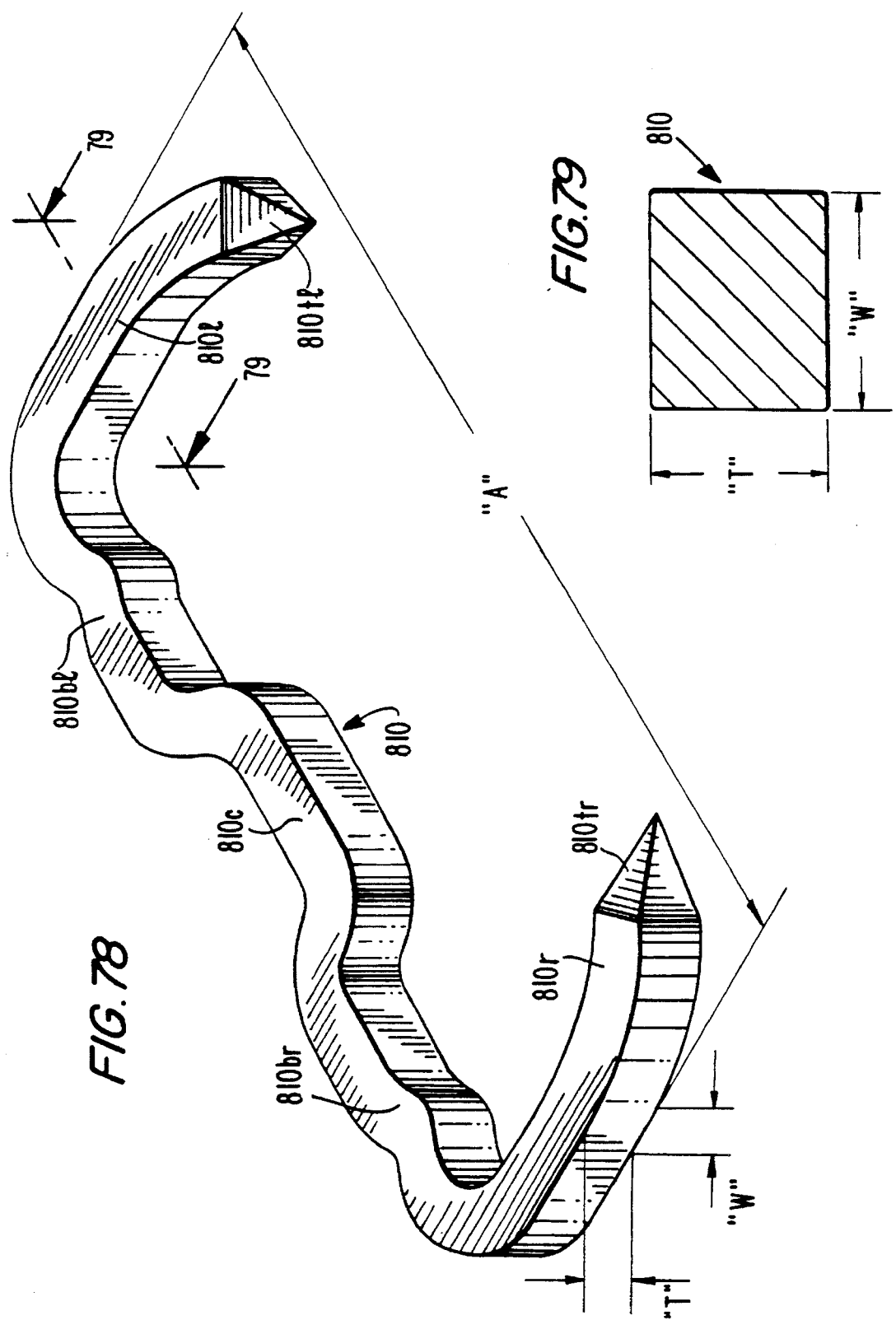

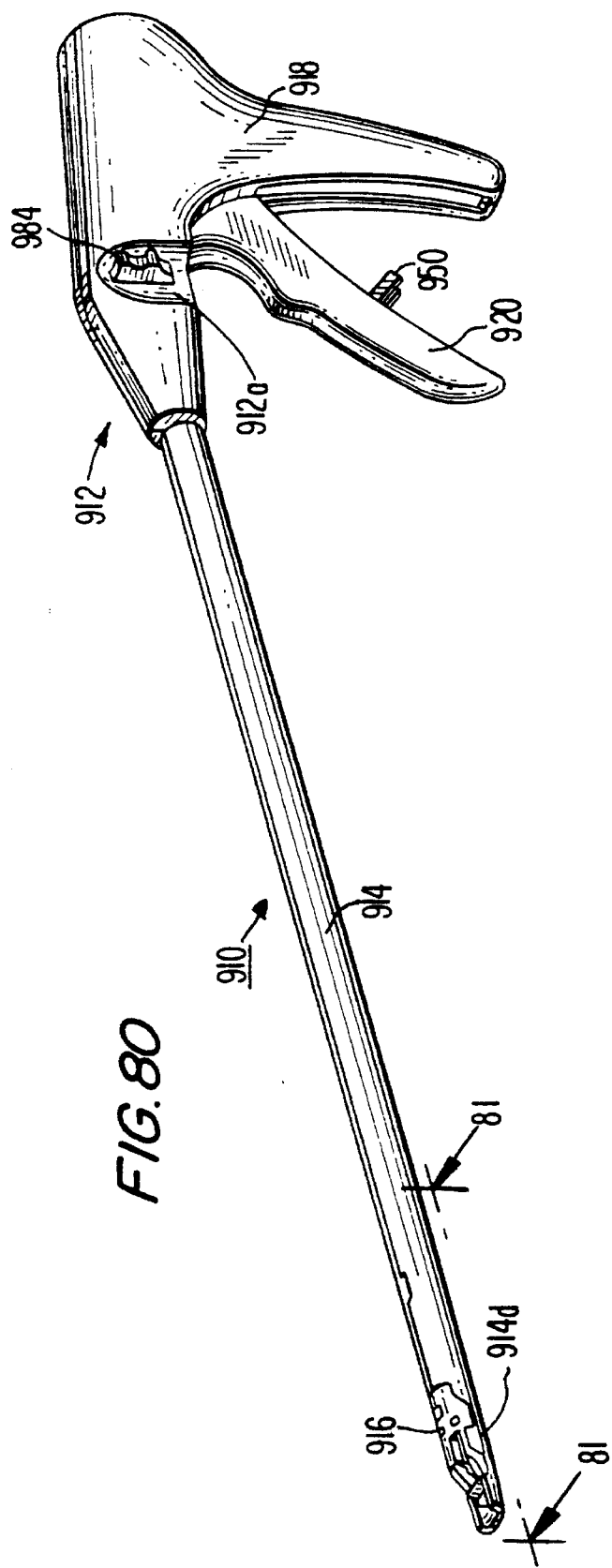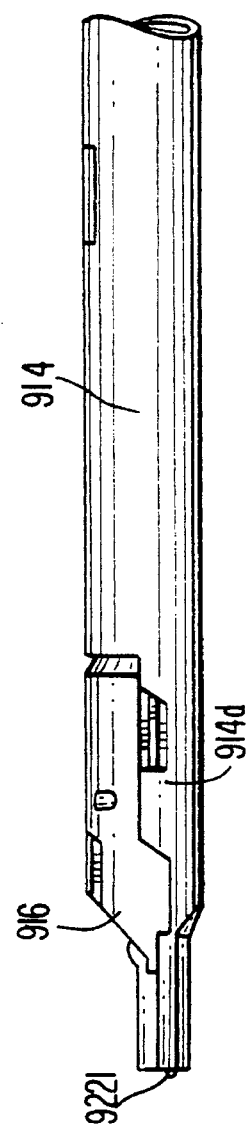

5,497,933

APPARATUS AND METHOD FOR APPLYING SURGICAL STAPLES TO ATTACH AN OBJECT TO BODY TISSUE

CROSS REFERENCE TO RELATED APPLICATION

This application is a continuation-in-part of application Ser. No. 07/950,425, filed Sep. 3, 1992, now U.S. Pat. No. 5,356,064 which is a continuation-in-part of application Ser. No. 07/861,065, filed Mar. 31, 1992, now U.S. Pat. No. 5,364,002 which is a continuation-in-part of application Ser. No. 07/782,290, filed on Oct. 18, 1991, now U.S. Pat. No. 5,289,963.

BACKGROUND OF THE INVENTION

1. Field of the Invention

The present invention relates to an apparatus and method for applying surgical staples to attach objects to body tissue. More particularly, this invention relates to a staple applier particularly adapted for attaching surgical mesh to body tissue to reinforce a surgical repair of the body tissue, as in hernia repair.

2. Background of the Invention

Hernias may be divided into three general classes: direct hernia, indirect hernia and femoral hernia. In a direct or indirect inguinal hernia, often a part of the intestine protrudes through a defect in the supporting abdominal wall to form a hernial sac requiring surgery which generally includes a surgical incision in the groin ranging up to six inches in length. Several layers of the abdominal wall are generally separated to reach the herniated portions. During the procedure, the hernia is closed outside the abdominal wall in a manner which resembles the tying of a sack at the neck. Often a surgical mesh is attached by sutures directly over the hernia repaired opening to provide a reinforcement to the opening.

Traditionally, such hernia repairs involved major invasive surgical procedures which often caused excessive trauma to the patient and necessitated unusually long post-operative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe 0 trauma to the patient. A detailed discussion of traditional hernia repair may be found in "Hernia Repair Without Disability, Second Edition", by Irving L. Lichtenstein.

Such invasive surgical procedures have also been utilized in other areas of the body, including surgery on the gall bladder, appendix, lungs and the like. For the reasons previously stated, the use of laparoscopic and endoscopic surgical procedures have been relatively popular and such popularity has provided additional incentive to develop the procedures further.

In laparoscopic procedures, surgery is performed in the interior of the abdomen through a small incision; in endoscopic procedures, surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments be used in such procedures be long and narrow while being functionally controllable from one end of the instrument, i.e. the proximal end.

In hernia surgery, as compared to gall bladder surgery, certain procedures and instruments are the same, yet certain of the instrument requirements differ. For example, in hernia surgery a suitable mesh material is generally sutured over the opening in the tissue. The mesh material is often also attached by sutures and left within the opening to act as a reinforcing agent for tissue regrowth in the area of the surgery. One example of a mesh material currently utilized in hernia surgery includes a polypropylene material marketed by the Ethicon division of Johnson & Johnson, New Brunswick, N.J., under the trademark MARLEX. Another example of a mesh material is a tri-fluoroethylene material marketed by W. L. Gore & Associates, Newark, Del., under the trademark GORE-TEX.

As noted, during conventional invasive surgical procedures, such mesh materials are often sutured within the surgical opening or over the sutured opening by conventional suturing techniques. However, with the advent of laparoscopic surgery the need for suitable mesh attachment techniques through the relatively narrow endoscopic tubes or cannulas is clearly defined. Up to the present, such devices or staples suitable for mesh attachment have not yet been developed.

U.S. Pat. Nos. 4,944,443 and 5,125,553 to Oddsen et al. discloses an instrument and method for applying and forming staples into body tissue to suture a hernial opening. The staple is applied to two pieces of body tissue on opposite sides of the opening which are gripped, approximated and held together by a tissue positioning assembly. U.S. Pat. No. 4,919,152 to Ger relates to a surgical instrument for placing a single clip which is proposed for use in direct hernia repair for closing sacs having narrow neck openings.

The present invention relates to an improved apparatus as well as a method for attaching body tissue and/or objects such as surgical mesh thereto with staples particularly configured and adapted to accomplish these objectives.

SUMMARY OF THE INVENTION

An apparatus for endoscopic application of a surgical staple adapted to attach objects to body tissue, which comprises frame means, generally elongated endoscopic means connected to the frame means and extending distally therefrom, means for storing at least one surgical staple at the distal end portion, the staple configured and adapted to attach an object to body tissue, means for individually advancing the at least one staple distally for positioning adjacent the body tissue, and anvil means for closing the staple in a manner to encompass at least a portion of the object and to penetrate the body tissue to attach the portion of the object to the body tissue. Preferably, the apparatus for endoscopic application of surgical staples is adapted to attach surgical mesh to body tissue and comprises means for storing a plurality of surgical staples in generally stacked relation to permit configuring and dimensioning the endoscopic means for insertion into an endoscopic cannula tube. The staples are configured and adapted to attach the surgical mesh to body tissue, particularly for hernia related surgery. Further, the staple advancing system extends from the frame means to the endoscopic means and is activated by a trigger mechanism pivotally attached to the frame means and forming a part thereof.

The surgical staples are stored in stacked relation at the distal end of the endoscopic means. Also, the endoscopic means defines a longitudinal axis and the surgical staples are stacked to form an angle with the longitudinal axis, thereby improving visibility.

The surgical staple storing means is pivotally attached at the distal end portion of the endoscopic means wherein 5 the surgical staple storing means is selectively pivotable by the user. Pivotal control means is located at the proximal end of the endoscopic section to pivot the surgical staple storing means from a proximal location. The location of the pivotal control means is provided for convenience and accessibility to the operator. The pivotal control means of the staple storing means comprises a member movable with respect to the endoscopic means in proximal and distal directions and adapted to position the surgical staple storing means at substantially zero degrees with respect to the longitudinal axis when the pivotal control means is in a first position and the surgical staple storing means forms an angle of up to about 45 degrees when the pivotal control means is in a second position.

The first position may be the proximalmost position of the pivotal control means and the second position may be the distalmost position corresponding to the staple storing means being pivoted up to about 45 degrees with respect to at least one side of the longitudinal axis. Further, the pivotal control means of the staple storing means may include a generally cylindrical movable member slidably positioned about a proximal portion of the endoscopic means.

The pivotal control means may also comprise a rotatable sleeve positioned within the movable member and adapted to rotate in a first direction when the movable member is moved toward the proximalmost position and to rotate in the opposite direction when the movable member is moved toward the distalmost position.

The surface at the distalmost end portion of the rotatable sleeve may form an angle with respect to the longitudinal axis of the endoscopic means and the distalmost end surface of the rotatable sleeve may be positioned and arranged to engage elongated control means positioned within the endoscopic means for engagement with at least a portion of the staple storing means at a distal location of the endoscopic means whereby rotatable movement of the rotatable sleeve correspondingly produces longitudinal movement of the elongated control means. Preferably, the elongated control means comprises at least two elongated rods positioned within the endoscopic means and in engagement with the distalmost end portion of the rotatable sleeve at the proximal ends thereof and arranged to engage at least a portion of the staple storing means at respectively opposed locations such that rotation of the rotatable sleeve in a first direction produces distal movement of at least one of the rods and corresponding proximal movement of the other rod and rotation of the rotatable sleeve in the opposite direction respectively produces correspondingly respectively opposite movement of the rods.

The staple storing means includes an indentation adapted to receive each rod in engagement therewith and each rod is correspondingly configured at the distal end to engage the respective indentation to produce smooth rotation of the staple storing means when the rods are respectively moved distally and proximally. Further, the means for individually advancing the staples distally is user controllable at a proximal location. The means for individually advancing the staples distally comprises a plate member positioned adjacent and proximal of the lowermost staple and adapted to be movable distally whereby the plate member engages the lowermost staple and advances the staple in the distal direction. Also, the means to individually advance the staples comprises staple pusher means. The staple pusher means comprises the plate member and the plate member is dimensioned, configured and arranged to engage and advance each staple distally.

The staple pusher means includes an elongated member of super elastic material such as TINEL brand metal and is adapted to advance the staples and transmit closing force thereto. This member is further adapted to resiliently deform to facilitate pivoting movement to the staple storing means. Another example of such metal is NITINOL brand metal. The staple pusher means further comprises an elongated staple firing rod.

In the preferred apparatus the staple pusher means is biased to a pre-fired position by a constant force negator spring which prevents the operator tendency to rotate the hand, which occurs when a spring force increases.

Also a trigger mechanism is pivotally mounted for pivotal movement against the force of the negator spring when pivoted proximally to a position corresponding to advancing the pusher means distally to advance the staple next in line for closure.

The staple storing means includes anvil means positioned distally of the stack of staples and configured, dimensioned and adapted to be engaged by each staple when the staple is advanced distally by the plate member.

The staples are each formed of a first length of wire having at least two leg portions at each end extending generally perpendicular to the first length of wire. The anvil means comprises at least two upstanding leg members positioned to be engaged by the first length of wire of each staple when the staple is advanced distally by the plate member. The leg members of the anvil means are dimensioned, positioned and arranged such that engagement by the first length of wire of each staple causes the leg members of the staple to fold inwardly toward the first wire due to the configuration of the staple and the corresponding configuration of the distalmost staple engaging edge of the plate member. The plate member is connected to elongated means comprised of super elastic member and the firing rod.

The means to move the elongated means and the plate member in distal and proximal directions is positioned within the frame means. Resilient means is positioned below each staple such that upon completion of closure thereof, and withdrawal of the staple advancing plate member the resilient means resiliently lifts the staple above the level of the anvil means. Also, the elongated means extends from the frame means through the endoscopic means whereby a distal portion thereof and the plate member are positioned within the staple storing means. The means to advance the elongated means and the plate member includes ratchet and associated pawl means adapted to prevent proximal movement thereof except when the staple advancing means is advanced to the distalmost position whereby the pawl means is released so as to permit return of the elongated member and the staple advancing plate member to the proximalmost position to advance the next staple of the stack of staples.

Preferably, the ratchet and pawl means comprises a ratchet member fixedly connected to the frame means and has a ribbed surface, and pawl means connected to the elongated plate advancing means and positioned adjacent the ratchet member and adapted to engage the ribbed surface. The ribbed surface is correspondingly configured and dimensioned to 5 prevent proximal movement of the pawl means when the elongated plate advancing means is advanced at least partially in the distal direction. The ribbed surface of the ratchet member is comprised of a plurality of substantially and successive V-shaped peaks and valleys and the pawl means is configured at one end portion to engage the peaks and valleys in a manner which permits distal slidable movement thereof but prevents proximal movement thereof. Also, means is provided to release the pawl means when the pawl means is in the distalmost position corresponding to the distalmost position of the plate member and closure of the staple has been completed. A finger operative lever is adapted to produce distal movement of the elongated member and the plate member when the lever is pivotally moved.

A preferred frame means has a pistol-like shape and includes a first member having a distal end connected to the endoscopic means and a manually gripping member at the proximal end is adapted to be gripped manually by the user. The endoscopic means is rotatable about the longitudinal axis and the pivotal control sleeve of the staple storing means is connected for rotation with the endoscopic means such that rotation thereof produces corresponding rotation of the endoscopic means. As described hereinabove, distal and proximal movement thereof produces pivotal movement of the staple storing means. The staple storing means is adapted to be pivoted up to about 45 degrees with respect to each side of the longitudinal axis whereby full pivotal articulation thereof is provided of about 90 degrees.

A surgical staple is adapted to attach objects such as mesh materials to body tissue which comprises, a length of 5 wire having a central portion, a wire leg member extending generally perpendicular to the central wire portion at each end portion and adapted to penetrate the object and body tissue when positioned in adjacent engaged relation therewith and advanced thereinto. A bridge portion connects the central wire portion to each leg member and has a first generally arcuate portion generally concave and facing in a direction generally toward the center of the central wire portion. The inwardly facing concave portions are connected to each leg member by an arcuate portion having a generally concave configuration in the opposite direction so as to respectively engageably support each bridge portion against a pair of anvil members whereby applying force to the bridge portions causes the leg members to bend inwardly toward the central wire portion at respective locations inward of the first mentioned arcuate portions in a manner to form an acute angle relative thereto. The maximum distance between the central wire portion and each folded leg member is sufficient to grip the object and to penetrate the body tissue sufficient to attach the object to the body tissue. Each leg member has a pointed tip to penetrate the object and the body tissue.

Each leg member of the staple has a tapered portion at the free end. The tapered portion on one leg member is located opposite the tapered portion on the other leg member whereby folding the leg members inwardly toward each other causes each tapered portion to respectively cam the other leg member whereby the leg members are folded toward each other in adjacent relation without interference with each other. The central wire portion is positioned inwardly of each bridge portion to facilitate gripping the object between the central wire portion and the leg members. Further, each leg member has a generally arcuate shape and has a concave portion thereof generally facing the other leg member. The surgical staple is preferably made of titanium. Also, the central wire portion includes a portion thereof which is positioned inwardly of the bridge portions in the body tissue gripping direction to thereby form a bight portion for gripping the object and body tissue in combination with the leg members.

A method is disclosed for endoscopically applying surgical staples to attach objects such as surgical mesh to body tissue comprising the steps of storing at least one surgical staple in endoscopic means having storing means positioned at the distal end portion and adapted for advancing and closing the staple, positioning the object adjacent the body tissue for attachment to the body tissue, and advancing the surgical staple distally so as to penetrate the object and the body tissue and to close the staple in a manner to attach the portion of the object to the body tissue. Preferably, a plurality of surgical staples are stored in stacked relation in the endoscopic means.

The invention relates to the combination of a cannula adapted for insertion into a body cavity, the cannula including valve means for sealing the cannula. An endoscopic surgical staple applier has a frame, and an endoscopic portion defining a longitudinal axis, and extending distally from the frame, the endoscopic portion configured and adapted for insertion into the cannula through the valve means in sealing engagement therewith. The endoscopic portion further includes a plurality of surgical staples in stacked relation, and means for individually pushing the staples through the distal end thereof is provided whereby staple closing means causes the staples to be closed while attaching an object such as surgical mesh to the body tissue. Seal means is positioned and adapted to obstruct passage of gaseous media from the body cavity.

A kit is also disclosed for endoscopic application of a surgical staple adapted to attach surgical mesh to body tissue in hernia repair, which comprises, surgical mesh, cannula means, and apparatus for endoscopic application of a surgical staple adapted to attach the surgical mesh to body tissue. The apparatus and staples of the kit are constructed according to the invention. The components may be supplied as part of a kit or they may be packaged in a blister-type or other package.

In an alternative embodiment, an apparatus is disclosed for endoscopic application of a surgical staple adapted to attach an object to body tissue, which comprises frame means, generally elongated endoscopic means connected to the frame means and extending distally therefrom, cartridge means for storing at least one surgical staple at the distal end portion, the staple being configured and adapted to attach an object to body tissue. Means is provided for individually advancing the at least one staple distally for positioning adjacent the body tissue, and anvil means is provided for closing the staple in a manner to encompass at least a portion of the object and to penetrate the body tissue to attach the portion of the object to the body tissue.

In the preferred embodiment, the apparatus includes on the elongated endoscopic means, means for engageably receiving and supporting the cartridge in a manner to advance the staples individually for endoscopic application.

A cartridge is also disclosed for containing a plurality of surgical staples for fastening body tissue which comprises housing means adapted to support the plurality of surgical staples, and means dimensioned, positioned and adapted to engage each staple as the staple is advanced from the housing means in a manner to prevent the staple from deforming out of the plane of the staple when the staple is deformed to attach the staple to body tissue.

The invention also relates to a system for attaching surgical mesh to body tissue adjacent a tissue repair within a body cavity which comprises, a frame, and an elongated endoscopic section connected at the proximal end thereof to the frame and extending distally therefrom, the endoscopic section configured and adapted for insertion into an endoscopic cannula within the body cavity. The endoscopic section includes a disposable cartridge adapted to store a plurality of surgical staples in stacked relation, the cartridge being removably engageably supported by a pivotal support member, each staple being formed of a first length of wire having at least one leg portion at each end extending generally perpendicular to the first length of wire, the leg portions being continuous with the first length of wire and configured to facilitate insertion into surgical mesh and adjacent body tissue therebeneath when the staple is advanced toward the mesh. The staple is further configured to facilitate folding the legs inwardly toward the first length of wire when at least a portion of the first length of wire is advanced against anvil means, whereby the leg portions and the first length of wire grip the mesh and the body tissue therebetween to attach at least the gripped portion of the mesh to the body tissue.

In this system, means is provided for individually advancing the staples distally for positioning adjacent the mesh and the body tissue. Means is also included for providing perceptible tactile indicator when each staple is advanced to a predetermined position. Means is provided for closing each staple while the staple is advanced toward the mesh and the body tissue so as to penetrate the mesh and the body tissue while causing the leg members to fold inwardly toward the first wire of the staple to grip the mesh and the body tissue between the first wire and the leg members.

A method is disclosed for endoscopically applying surgical staples to attach objects such as surgical mesh to body tissue comprising the steps of storing at least one surgical staple cartridge positioned at the distal end portion and adapted for advancing and closing the staple, positioning the object adjacent the body tissue for attachment to the body tissue, and advancing the surgical staple distally so as to penetrate the object and the body tissue and to close the staple at least sufficient to attach the portion of the object to the body tissue.

A kit is disclosed for endoscopic application of a surgical staple adapted to attach surgical mesh to body tissue in hernia repair, which comprises surgical mesh, cannula means, and apparatus for endoscopic application of a surgical staple adapted to attach the surgical mesh to body tissue. The apparatus includes frame means, and generally elongated endoscopic means connected to the frame means and extending distally therefrom and dimensioned and configured for insertion into the cannula means. The endoscopic means includes a removable and replaceable cartridge for storing a plurality of surgical staples at the distal end portion, the staple configured and adapted to attach objects to body tissue, means for individually advancing the at least one staple distally for positioning adjacent the surgical mesh and the body tissue, and anvil means for closing the staple at least sufficient to encompass at least a portion of the surgical mesh and to penetrate the surgical mesh and the body tissue in a manner to attach the portion of the surgical mesh to the body tissue.

In another alternative embodiment an apparatus is disclosed for endoscopic application of a surgical fastener, which comprises a frame, an elongated member connected to the frame and extending distally therefrom, and means cooperating with the elongated member for storing at least one surgical fastener. Pusher means is provided for advancing the at least one fastener distally for positioning adjacent the body tissue. Means is provided for closing the fastener, and means is provided to rotate the staple storing means about an axis extending generally longitudinally thereof.

Preferably, the endoscopic apparatus comprises an elongated member having a distal end portion and a proximal end portion and defining a longitudinal axis, a working head at the distal end portion of the elongated member, means to 0 control the operation of the working head from a proximal end portion, and means to rotate the working head about an axis extending therethrough independent of the elongated member. Preferably, the apparatus further comprises means to rotate the elongated member about the longitudinal axis from a proximal position. Also the means to rotate the elongated member from a proximal position about the longitudinal axis preferably comprises means to pivotally rotate the working head to at least two selected angles relative to the longitudinal axis of the elongated member. The first angle is about 32.5° and the second angle is about 65°.

The working head preferably comprises cartridge support means pivotally attached to the elongated member, and cartridge means supported by the cartridge support means and adapted to contain surgical fasteners wherein the fasteners are surgical staples. The means to rotate the elongated member comprises control means positioned at a proximal end portion of the elongated member. The means for effecting rotation of the working head about its own axis comprises a staple advancing plate member nestled within the working head in a manner such that rotation of the plate member effects rotation of the working head, elongated means extending from the frame means to the staple advancing plate member and connected thereto, and control means connected to frame means and operable for effecting rotation of the working head about an axis extending therethrough. Generally, this embodiment facilitates application of staples at predetermined locations and at predetermined angles, with improved extreme precision, with ease of operation to the user.

In further alternative embodiments an apparatus is disclosed for endoscopic application of surgical staples which comprises a generally elongated endoscopic portion having a generally longitudinal axis and terminating in a distal end portion movable between at least a first position extending in substantially the same direction as the longitudinal axis and at least a second position at an angle to the longitudinal axis. The apparatus also includes means for moving the distal end portion between the first position extending in substantially the same direction as the longitudinal axis and the second position at an angle relative to the longitudinal axis, where the moving means is actuated from a position spaced from the distal end portion. A staple pusher is employed for advancing at least one staple located in the distal end portion from the distal end portion, and the staple pusher is actuable when the distal end portion is in the first and the second position.

In addition, the staple pusher includes at least two projections distally extending for applying pressure to a backspan of the at least one surgical staple as the staple is closed by an anvil member to prevent the backspan from bending. A gap is provided between the at least two projections for providing relief to the staple pusher to slide smoothly over the anvil member.

An anvil member is provided having at least two upstanding legs for closing the at least one surgical staple while applying same to body tissue. Each of the upstanding legs has a rounded surface portion on a proximal side for forming the at least one surgical staple therearound to close the at least one surgical staple. The anvil member has a projection and the distal end portion includes an aperture for correspondingly locating the projection of the anvil member to position the anvil member at the distal end portion. The distal end portion also includes a projection for positioning a portion of the anvil member substantially adjacent the distal end portion. The anvil member also has an aperture for correspondingly locating the projection of the distal end portion to position the anvil member substantially adjacent the distal end portion.

At least two distally extending tabs are provided for engaging body tissue for stabilizing the distal end portion relative to the body tissue during application of the staples. A spring channel member having a channel which permits surgical staples to pass therethrough is positioned in the distal end portion of the apparatus. The spring channel member includes resilient means for moving a closed surgical staple upwardly with respect to the distal end portion to release the staple therefrom. A projection of the spring channel member prevents surgical staples from moving in a proximal direction during application to body tissue.

BRIEF DESCRIPTION OF THE DRAWINGS

Preferred embodiments of the invention are described hereinbelow with reference to the drawings wherein:

FIG. 1A is a perspective view of the distal end portion of the apparatus of FIG. 1 illustrating an alternative embodiment for pivoting the staple storage magazine;

FIG. 4 is a cross-sectional view taken along lines 4—4 of FIG. 3 illustrating the mechanism at the proximal end of the instrument for providing controlled distal movement to advance and to close staples at the distal end;

FIG. 5 is an enlarged cross-sectional view of the pawl and ratchet system in the handle which prevents proximal movement of the staple advancing system after distal movement has begun;

FIG. 6 is a view similar to FIG. 5 illustrating the pawl and ratchet system of FIG. 5 after a staple has been fired and during the proximal movement of the firing mechanism;

FIG. 8 is an enlarged cross-sectional view taken along lines 8—8 of FIG. 1 illustrating the rotating mechanism for the endoscopic portion and the system for pivoting the staple storage magazine from the proximal end;

FIG. 9 is a cross-sectional view taken along lines 9—9 of FIG. 8;

FIG. 10 is a cross-sectional view taken along lines 10—10 of FIG. 8 illustrating the system for providing pivotal motion of the staple storage magazine located at the distal end;

FIG. 16 is a cross-sectional view taken along lines 16—16 of FIG. 1 illustrating the distal end of the instrument including the pivotal staple magazine at three positions;

FIG. 17 is a cross-sectional view taken along lines 17—17 of FIG. 16 illustrating the staple next in line and the pusher plate provided for advancing the staple toward a staple closing anvil;

FIG. 18 is a cross-sectional view of the distal end of the instrument shown in engagement with a surgical mesh positioned against body tissue prior to firing the staple;

FIG. 19 is a cross-sectional view taken along lines 19—19 of FIG. 18;

FIG. 20 is a cross-sectional view similar to FIG. 18 during the firing of the staple and after penetration into the mesh and body tissue, but prior to closure;

FIG. 21 is a view similar to FIG. 19, taken along lines 21—21 of FIG. 20;

FIG. 22 is a cross-sectional view of the distal end of the instrument of the invention after closure of the staple in position to attach the surgical mesh to the body tissue;

FIG. 23 is a cross-sectional view taken along lines 23—23 of FIG. 22 illustrating the staple ejection system for releasing the closed staple from the anvils after firing;

FIG. 24 is a cross-sectional view similar to FIG. 22 illustrating the staple after closure about the surgical mesh and body tissue and the distal end of the instrument withdrawn from the surgical mesh;

FIG. 25 is a cross-sectional view taken along lines 25—25 of FIG. 24;

FIG. 26 is a cross-sectional view of the distal end portion of the staple storing magazine of the instrument after firing a staple;

FIG. 27 is a frontal view of a repair in body tissue illustrating one example of an arrangement of staples of the invention for attachment of reinforcing surgical mesh to the tissue;

FIG. 28 is a perspective view of a staple constructed according to the invention for attaching surgical reinforcing mesh to body tissue over a surgical repair;

FIG. 29 is another example of arranging the staples for attachment of the reinforcing surgical mesh to the body tissue in the area of a hernia repair;

FIG. 30 is a perspective view from above similar to FIG. 1, of an alternative embodiment of the present invention which includes a replaceable staple storing cartridge at the distal portion of the endoscopic section;

FIG. 31 is an exploded perspective view with parts separated, of the handle of the instrument of FIG. 30 illustrating a feature which provides perceptible tactile sensing of the pre-positioning of each staple prior to closing the staple with respect to the body tissue;

FIG. 32 is an exploded perspective view with parts separated, of the system at the distal end portion of the endoscopic section for pivotally supporting a replaceable staple storage cartridge;

FIG. 32A is an exploded perspective view of the staple storage cartridge with parts separated;

FIG. 32B is a view taken along lines 32B—32B of FIG. 32A, illustrating the "L" shaped staple holders at the bottom of the cartridge housing;

FIG. 34 is a plan view from above of the staple storage cartridge and related pivotal support member illustrating the feature of the invention which prevents each staple from rolling backwardly as they are deformed;

FIG. 35 is a cross-sectional view of the staple storage cartridge and related pivotal support member taken along lines 35—35 of FIG. 30;

FIG. 39 is a partial internal view of the handle portion and the staple storage cartridge illustrating the perceptible tactile staple pre-positioning feature of the invention;

FIG. 40 is a perspective view of the internal sleeve and pin which forms part of the pivoting system for the staple storage cartridge, similar to the sleeve disclosed in FIG. 13 in connection with the previous embodiment of the invention;

FIG. 41 is a cross-sectional view taken along lines 41—41 of FIG. 30, illustrating schematically gaseous seal means for the endoscopic section;

FIG. 42 is a perspective view of an alternative embodiment of the invention wherein articulation of the staple storage magazine section is possible between 0°, 32.5° and 65°, respectively;

FIG. 43 is an exploded perspective view with parts separated, of the slidable collar and related mechanism for articulating the staple storage magazine section;

FIG. 53 is a cross-sectional view of a portion of the detent ball system of the slidable collar mechanism for retaining the staple storage magazine section in selected positions, illustrating the proximal-most ball and pin when the slidable collar is moved proximally a small amount from the 0° magazine section position;

FIG. 54 is a cross-sectional view similar to FIG. 53 illustrating the ball and detent positions when the staple storage magazine section is in the 32.5° position;

FIG. 55 is a cross-sectional view similar to FIG. 54 illustrating the ball and detent position when the staple storage magazine section is in the 65° position;

FIG. 56 is a cross-sectional view of the proximal portion of the endoscopic section and the distal portion of the handle section, with the handle outer structure removed for convenience of illustration, illustrating one system for rotating the staple storage cartridge about its own axis from the handle section;

FIG. 56A is a cross-sectional view taken along lines 56A—56A of FIG. 56;

FIG. 57 is a side view of the staple storage magazine section pivoted to the 32.5° position and illustrating schematically by arrows, the rotational capability of the staple storage magazine about its own central axis;

FIG. 58 is a frontal view taken along lines 58—58 of FIG. 57 illustrating in phantom lines, several of the angular orientations of the staple storage magazine section which are possible about its own axis when the section is pivotably rotated to the 32.5° angular position shown in FIG. 57;

FIG. 59 is a perspective view, with parts separated, of the proximal control system shown in FIG. 56, for rotating the staple storage magazine about the central axis thereof from the handle section mounted in conjunction with the ratchet and pawl system of the previous embodiments;

FIG. 60 is a cross-sectional view of the assembled components shown in FIG. 59 illustrating an alternative system for rotating the staple storage magazine section about its own longitudinal axis, incorporating an alternative ratchet and pawl system arrangement;

13

Figures 64, 65:
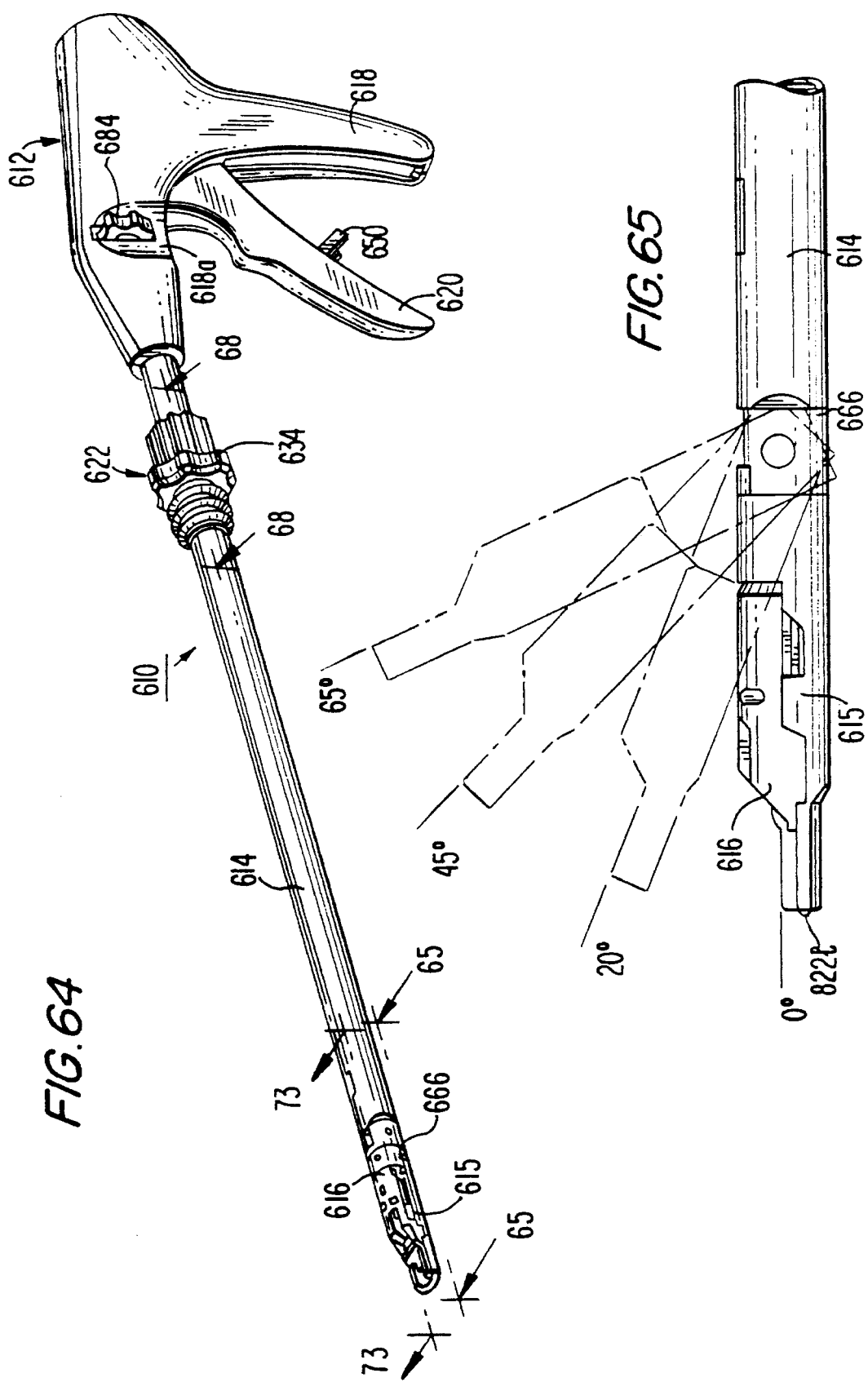
Figure 66:
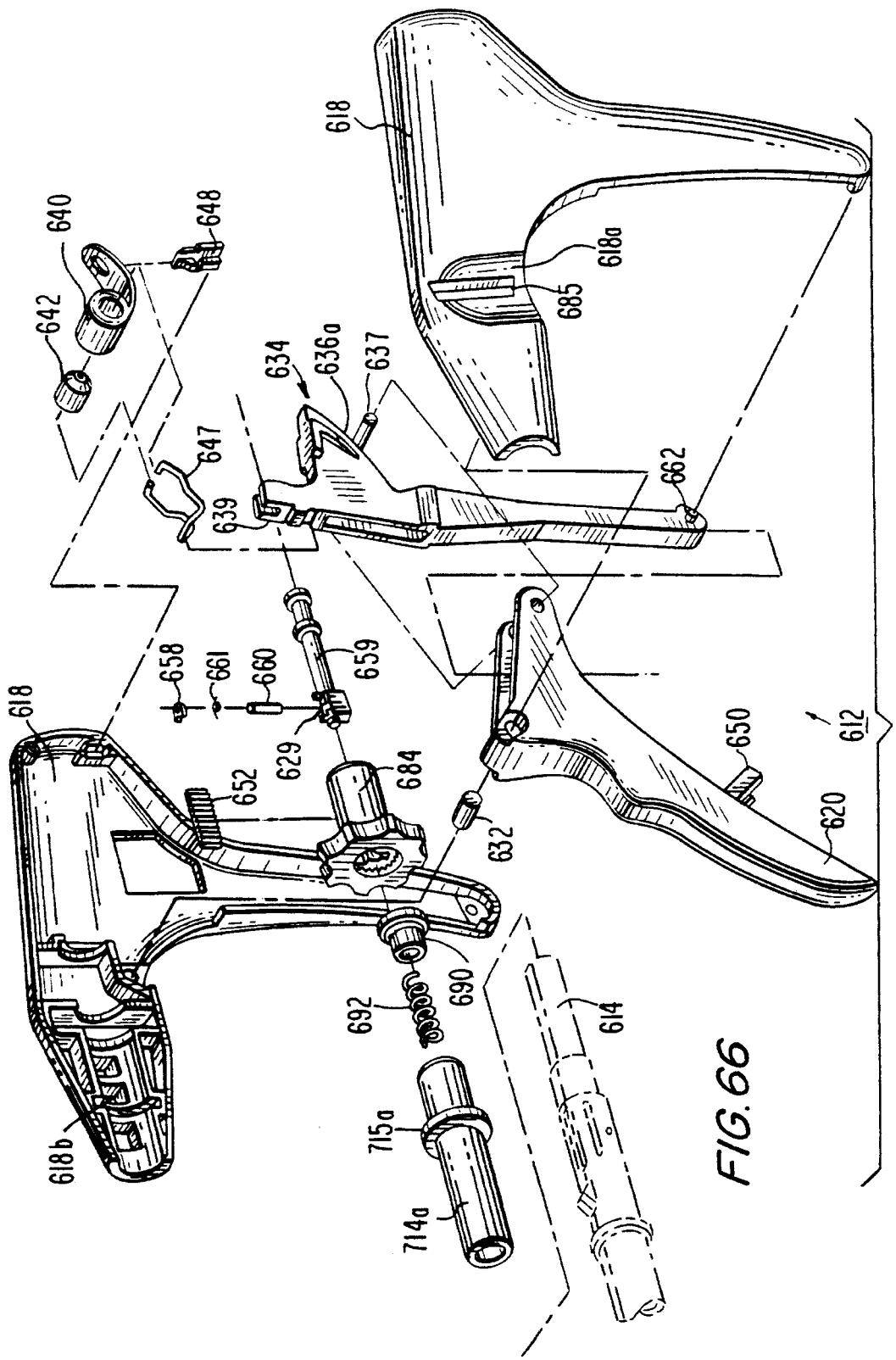
Figure 67:
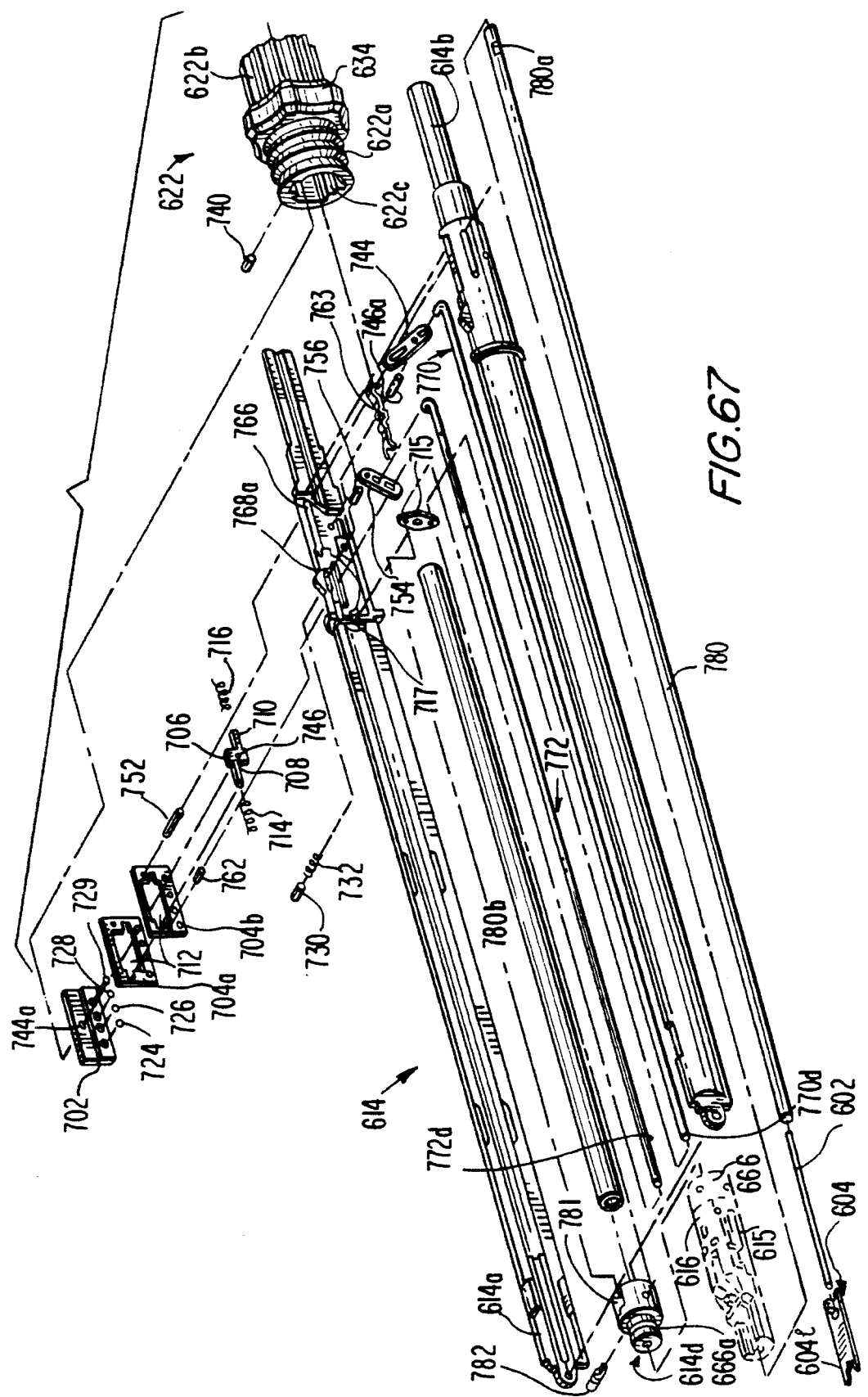
Figure 68:
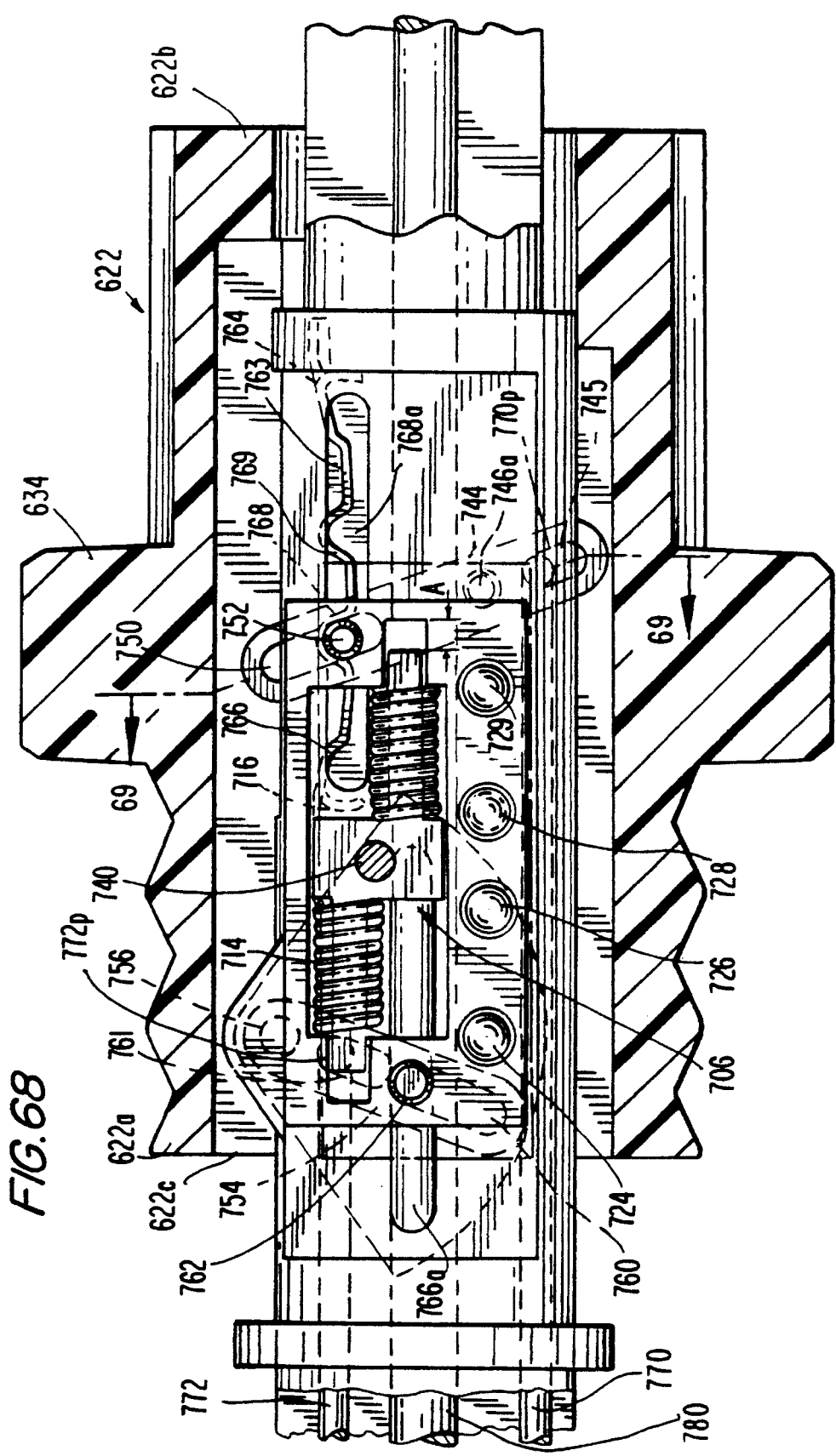
Figure 69:
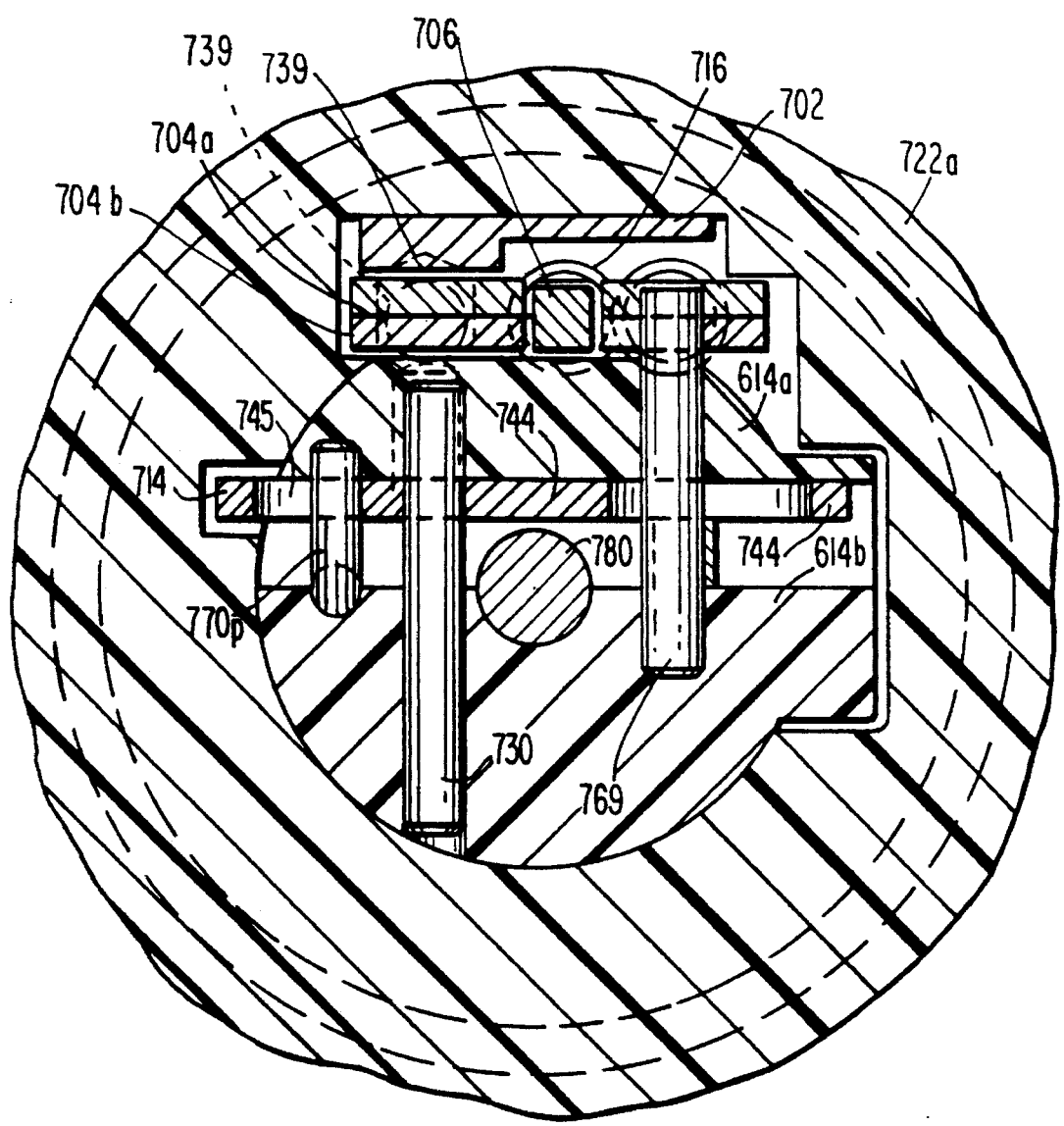

FIG. 60A is a cross-sectional view taken along lines 60A—60A of FIG. 60 illustrating the attachment for rotating the staple advancing member;

FIG. 61 is a side view similar to FIG. 57, illustrating the staple storage magazine section in the 65° position with respect to the longitudinal axis of the endoscopic section;

FIG. 62 is a view similar to FIG. 58 taken along lines 62—62 of FIG. 61, illustrating several of the angular orientations of the staple storage magazine section which are possible about its own axis when the section is pivoted to the 65° angular position shown in FIG. 61;

FIG. 63 is a perspective view similar to FIG. 59 illustrating the alternative embodiment of the proximal control system shown in FIGS. 60 and 60A;

FIG. 64 is a perspective view from above of an apparatus constructed according to an alternative embodiment of the present invention for applying surgical staples to body tissue;

FIG. 65 is a side elevational view of the distal portion of the apparatus of FIG. 64 illustrating a four position articulation system for pivoting a staple cartridge support member;

FIG. 66 is a perspective view, with parts separated for illustration purposes, of the handle and associated components of the instrument of FIG. 64;

FIG. 67 is a perspective view, with parts separated for illustration purposes, of the staple delivery cartridge sections of the instrument of FIG. 64 illustrating the staple advancing system and cartridge articulating control mechanism with components thereof;

FIG. 68 is a cross-sectional view taken along lines 68—68 of FIG. 64 illustrating the articulating control mechanism in a first position for providing pivotal motion to the staple cartridge support member at the distal end portion;

FIG. 69 is a cross-sectional view taken along lines 69—69 of FIG. 68 illustrating further details of the mechanism for providing pivotal motion to the staple cartridge support at the distal end portion;

FIG. 70 is a perspective view, with parts separated for illustration purposes, of the distal end portion of the instrument of FIG. 64 including the pivotal staple cartridge support system;

FIG. 71 is a side elevational view of the anvil member shown in FIG. 70;

FIG. 72 is a top plan view of the spring channel member shown in FIG. 70;

FIG. 73 is a cross-sectional view taken along lines 73—73 of FIG. 64 illustrating the distal end portion of the instrument including the pivotal staple cartridge support system;

FIG. 74 is a view taken along lines 74—74 of FIG. 73 illustrating the distal end of the instrument of FIG. 64;

FIGS. 75–77 are views from above of the distal end portions of the instrument of FIG. 64 in various stages of engaging and forming of a surgical staple to a formed position;

FIG. 78 is a perspective view of an alternative embodiment of the staple of the invention;

FIG. 79 is a cross-sectional view of the staple of FIG. 78, taken along lines 79—79;

FIG. 80 is a perspective view from above of a non-articulating alternative embodiment of the apparatus of the present invention for applying surgical staples to attach objects to body tissue; and FIG. 81 is a side elevational view of the distal end of the apparatus of FIG. 80 taken along lines 81—81.

14

DETAILED DESCRIPTION OF THE PREFERRED EMBODIMENTS GENERAL

In general, the objective of the apparatus is to store a plurality of staples in the magazine section as will be described in greater detail, and to individually advance each staple distally for closure about anvils while attaching a surgical mesh to the body tissue.

Following a general description of the present instrument, the description will be divided into separate sections to describe the structure and the desired movements produced thereby. Those sections include the handle section, the staple storage magazine pivoting system, the endoscopic section and staple firing system, the staple storage magazine, the staple closing system and the inventive staple. Also a kit for attaching objects such as surgical mesh is described. Alternative embodiments of the invention will thereafter be described.

THE INSTRUMENT

Figure 1:
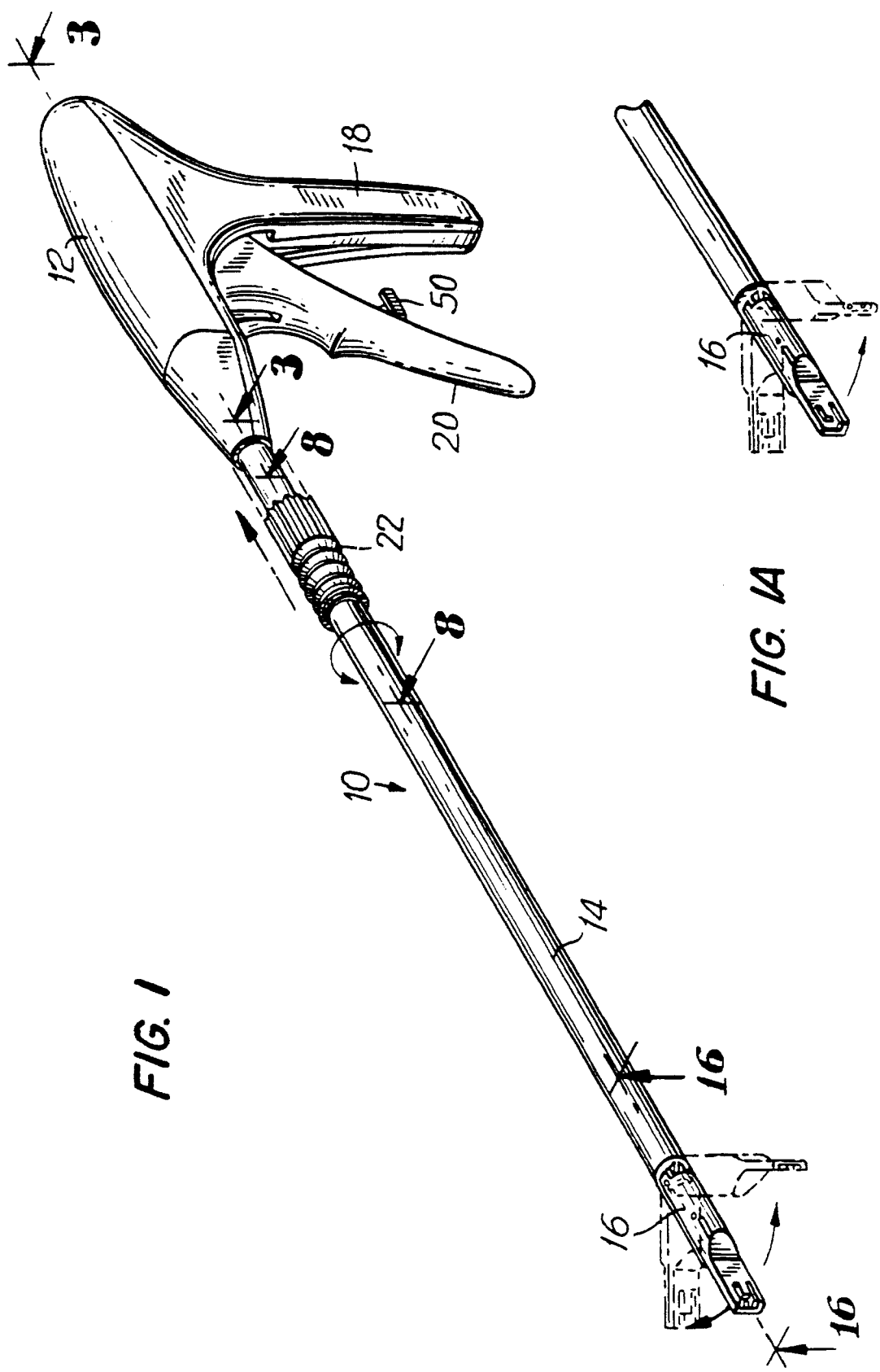
FIG. 1 is a perspective view from above, of an apparatus constructed according to the present invention for applying surgical staples to attach objects to body tissue.

Referring initially to FIG. 1 there is illustrated in perspective view the apparatus 10 particularly adapted for endoscopic application of surgical staples to attach surgical mesh to body tissue during hernia repair. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) may also be utilized. However, equivalent alternative materials will readily come to the mind of those skilled in the art.

The apparatus 10 includes handle portion 12, and endoscopic section 14 having at the distal end portion a staple storage magazine 16 which pivots with respect to at least one side of the longitudinal axis extending centrally through the endoscopic section as shown in FIG. 1. Generally, in this embodiment the staple storage magazine 16 will selectively pivot up to about 45 degrees with respect to the aforesaid longitudinal axis. In the illustration of FIG. 1 the staple storage magazine 16 is shown in general alignment with the longitudinal axis of the endoscopic section and in phantom to illustrate a range of movement. The total range of pivotal motion of the staple storage magazine 16 as shown is approximately 90 degrees, i.e. 45 degrees to each side of neutral.

Referring generally to FIG. 1, the handle 12 of instrument 10 includes manual grip 18 and pivotal trigger 20 5 which is pivoted toward and away from manual grip 18. Trigger 20 is pivoted toward manual grip 18 during the staple advancing and firing sequence which will be described in further detail. Trigger 20 pivots away from manual grip 18 to return the instrument to the pre-fired condition in position for firing the staple next in line.

A double knurled finger operative collar 22 is rotatable and adapted to rotate the entire endoscopic section 14 a full 360 degrees as will be described hereinbelow, while proximal movement of the finger collar 22 produces pivotal motion of the staple storage magazine to one of the positions shown in phantom in FIG. 1. To achieve the other position shown in phantom in that FIG., the collar 22 may be simply rotated 180 degrees thereby rotating the entire endoscopic section and causing the position of the magazine 16 to be reversed as shown to the other position shown in phantom.

Thus, it can be seen that the combination of full rotation of the endoscopic section and the pivotal movement of the staple storing magazine facilitates a wide range of articulation of the distal end of the staple magazine 16, thus facilitating application of staples over a wide range of locations (±180 degrees) and in any of a plurality of orientations. In the embodiment of the invention shown in the FIGS., when the collar 22 is moved to its proximalmost position the staple magazine is in one of the positions shown in phantom in FIG. 1, i.e. at an angle with respect to the longitudinal axis of the instrument. When the collar 22 is advanced to the distalmost position the staple magazine assumes the position shown in FIG. 1, i.e. in alignment with the longitudinal axis of the instrument.

Thus, in a preferred embodiment as shown in FIG. 1, it can be seen that the full 90 degrees of movement of the magazine may be achieved simply by longitudinal movement of collar 22 in combination with full rotation of the endoscopic section. The longitudinal movement of collar 22 causes pivotal movement of the staple storing magazine to 45 degrees in one direction and rotation of the endoscopic section provides completion of the articulation of the magazine. Both of these movements in combination, facilitate a wide range of maneuverability of the distal end of the staple magazine 16, thus facilitating application of staples over a wide range of locations (±180 degrees) and in any of a plurality of orientations.

Alternatively, the positions of the staple storing magazine 16 may be achieved as shown in FIG. 1A, i.e. by movement of the magazine between zero degrees and about 45 degrees on either side of the longitudinal axis. In such arrangement, to achieve the positions shown in phantom in FIG. 1A, the collar 22 is moved distally and proximally, equal distances on either side of a neutral tactile detent. Movement in one direction would pivot the magazine to one side and movement in the other direction would cause pivotal movement of the magazine in the opposite direction. The directions selected would be arbitrary. However, in this last described embodiment the orientation of the magazine would be the same throughout the 90 degree pivoting range, whereas in the preferred embodiment of FIG. 1, the orientation of the magazine when on one side is opposite the orientation when on the other. Further, in this embodiment the endoscopic section will be somewhat longer to accommodate the additional movement of collar 22.

THE HANDLE SECTION

Figure 2:
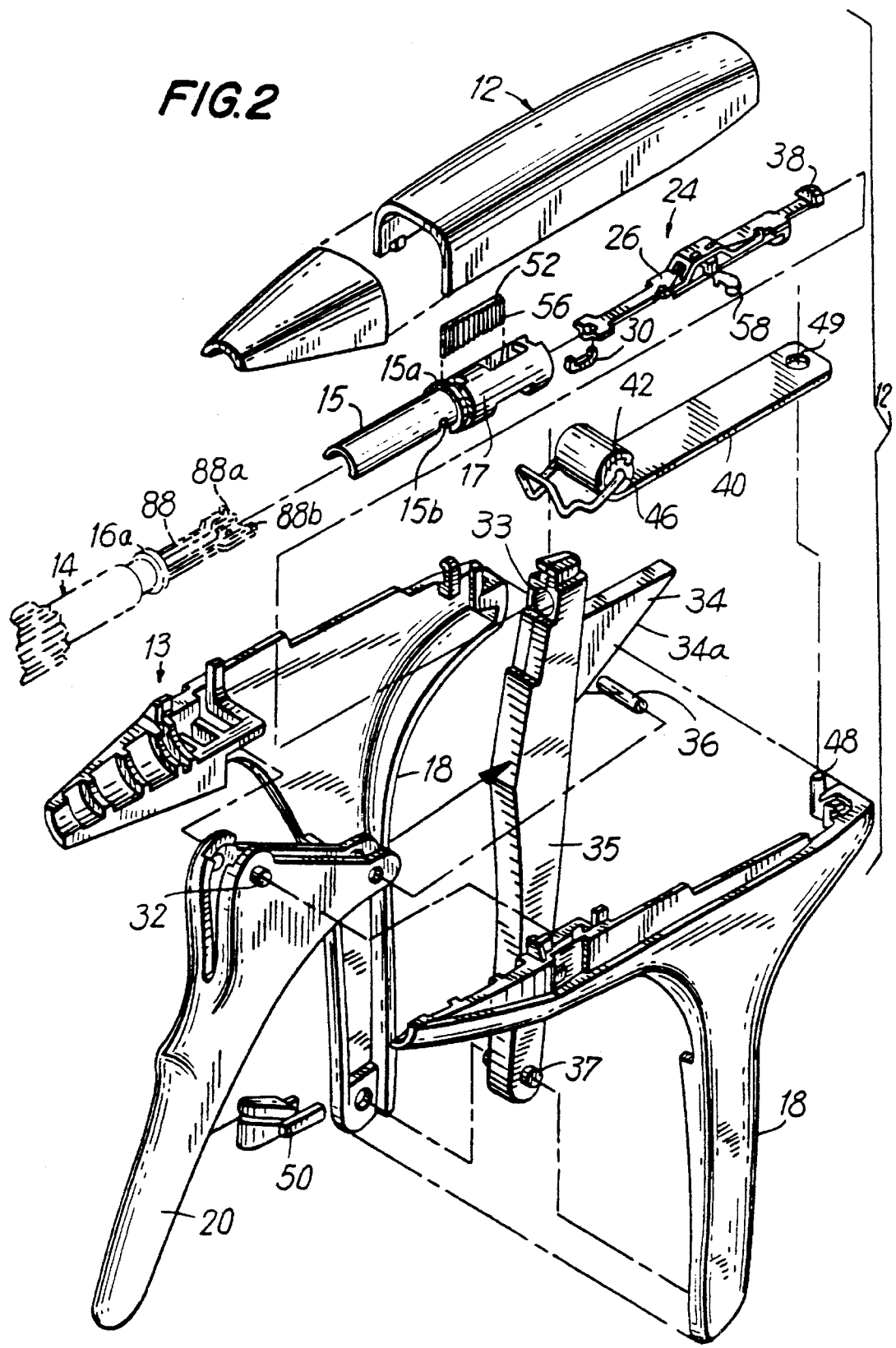
FIG. 2 is an exploded perspective view with parts separated, of the handle of the instrument of the invention and the associated components.
Figure 3:
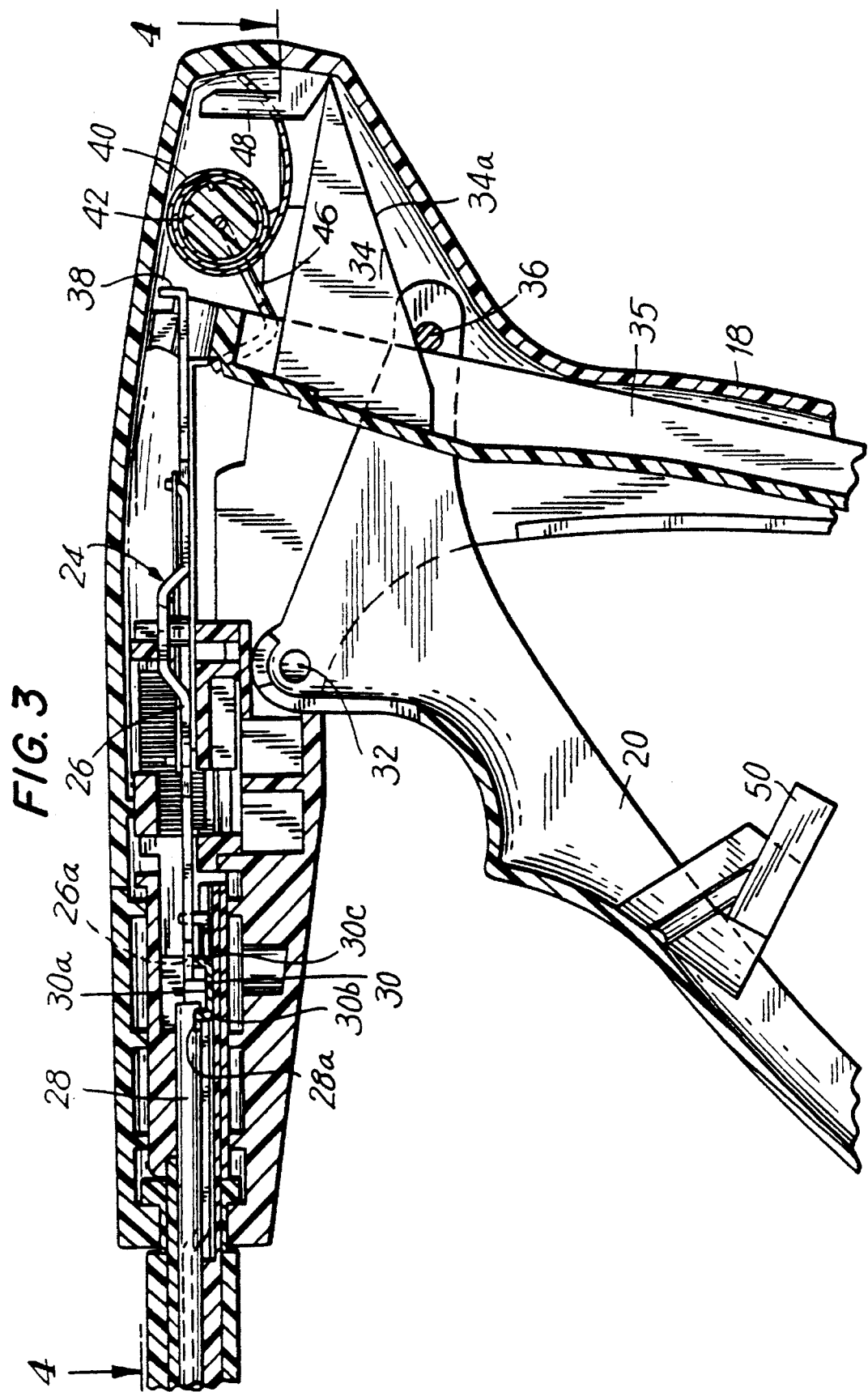
FIG. 3 is a cross-sectional view taken along lines 3—3 of FIG. 1, illustrating the handle mechanism of the instrument in the pre-fired condition.

Referring to FIG. 2, there is shown an exploded perspective view with parts separated, of the handle of the instrument with associated components. The handle is comprised of an outer housing preferably formed of separate sections as shown, of polycarbonate material. The separate parts shown are attached by welding, adhesives, etc. FIG. 3 illustrates a cross-sectional view of the handle mechanism taken along lines 3—3 of FIG. 1. The ultimate purpose of the handle mechanism is to provide controlled distal movement to the pusher assembly 24, a portion of which is shown in FIG. 2. The pusher assembly extends through the endoscopic section 14, a portion of which is shown in phantom in FIG. 2. In the embodiment shown, the endoscopic section shown is intended to be permanently and rotatably attached to the instrument via rim 16a formed at the proximal end of endoscopic section 14 and rim 15a on half round sleeve 15. The instrument shown is contemplated to be entirely disposable. Half round sleeve 15 is integrally formed with barrel 17 which is in turn affixed to handle 12 at the nose piece 13.

It is also contemplated and within the scope of the invention to construct the endoscopic section to be selectively detachable whereby the handle may be sterilized and reused, or the endoscopic section can be sterilized, and the staple storage magazine re-loaded with staples for reuse. Alternatively a replacement staple magazine, and optionally a replacement endoscopic section, may be detachably secured to a disposable handle for multiple use during a single surgical procedure. Thus, any combination of alternatives may be incorporated within the scope of the invention.

Figure 7:
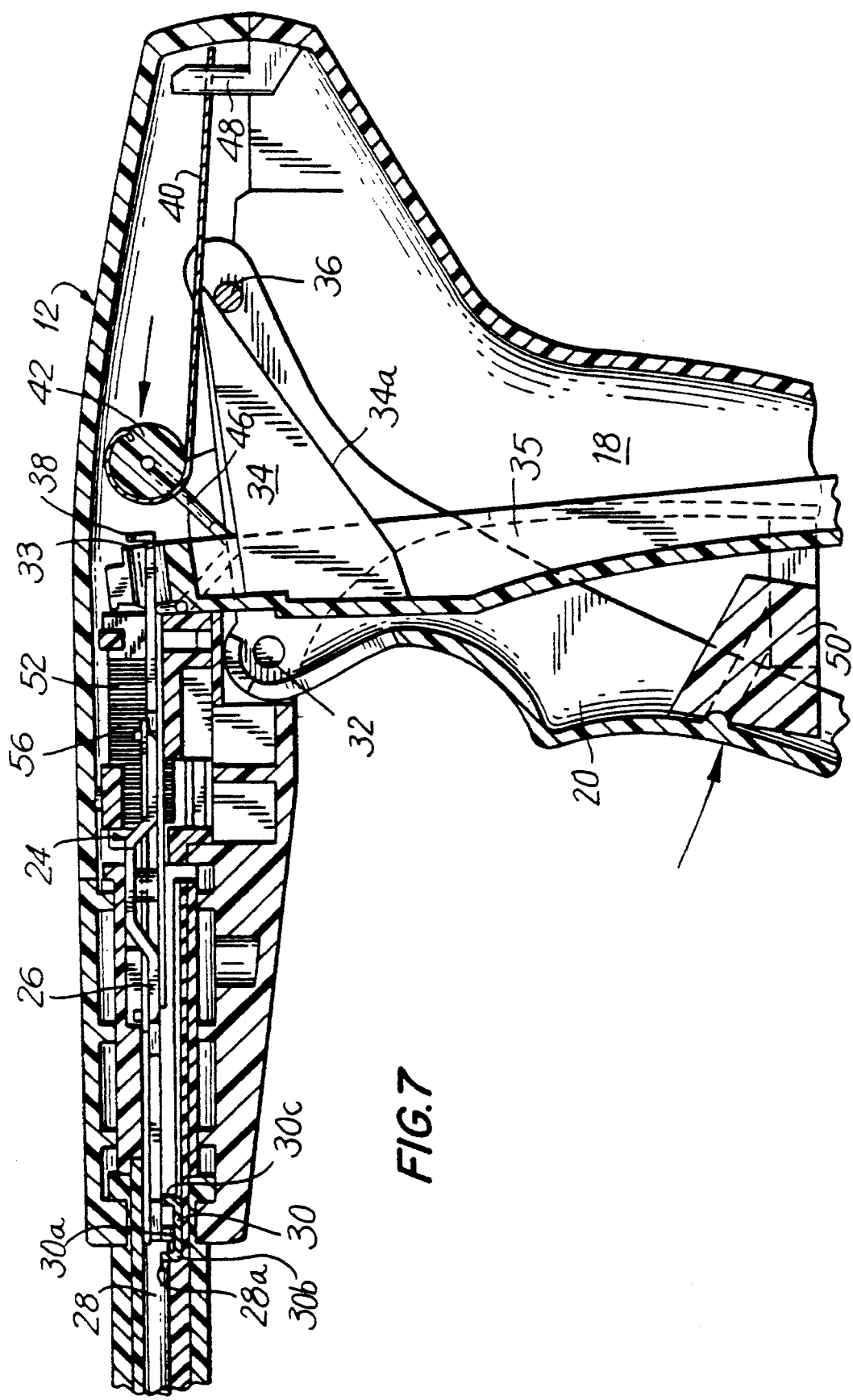
FIG. 7 is a cross-sectional view similar to FIG. 3 with the staple advancing actuating handle in the full proximal pivoted position corresponding to firing of a staple.
Figure 12:
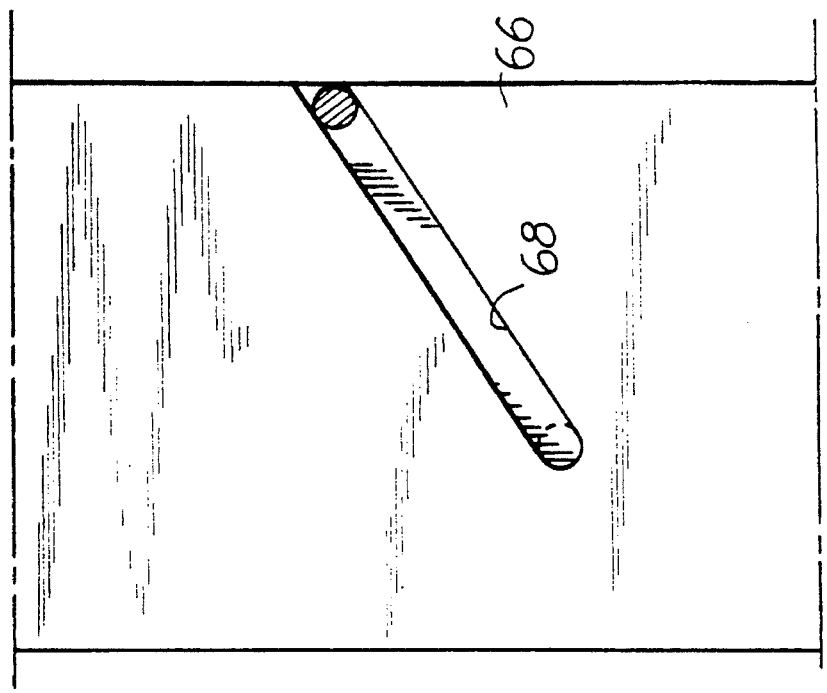
FIG. 12 is a view of the interior surface of the inner sleeve of the manually operable collar of FIGS. 8–11, projected as a flat surface to illustrate the helical groove provided for coaction with a pin to provide pivotal motion for the staple magazine at the distal end.
Figure 14:
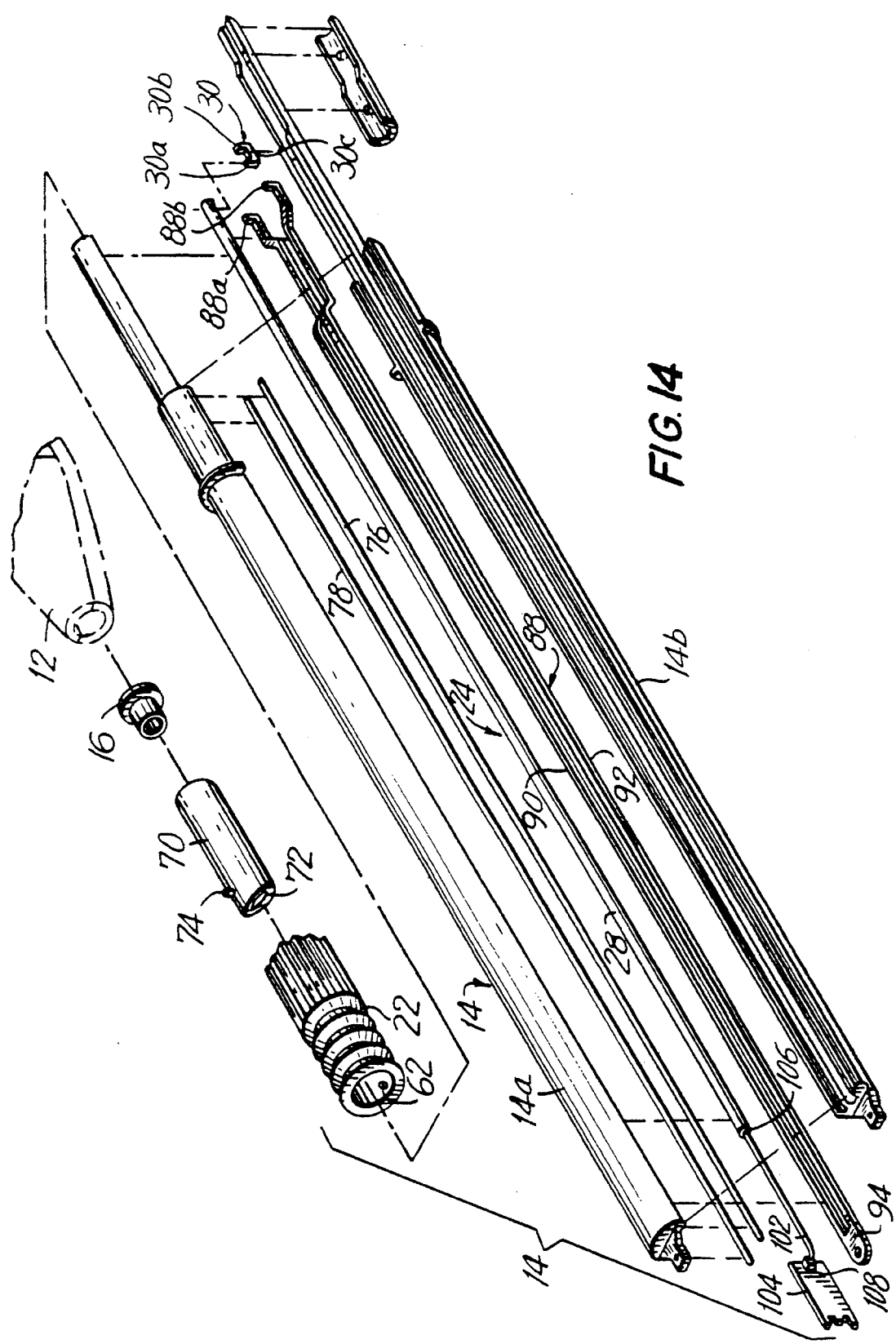
FIG. 14 is an exploded perspective view with parts separated, of the endoscopic section of the instrument of the invention, illustrating the staple advancing system and components thereof.

Referring now to FIG. 2 in conjunction with FIGS. 3, 7 and 14, pusher assembly 24 includes flanged thrust bar 26 connected to firing rod 28 by lost motion connector 30 as shown in FIG. 3. Lost motion connector 30 is a bar having a generally "U-shaped" configuration as shown. The lost motion connector 30 provides a positive connection between flanged thrust bar 26 and firing rod 28, yet provides a small space between the firing rod and the thrust bar 26 as will be described. Since the respective slots 28a and 26a in the firing rod 28 and in the thrust bar 26 are dimensioned slightly larger in width than the thickness of the legs 30b and 30c of the lost motion connector 30 which are received in these slots, a small degree of relative movement (i.e., about one tenth (1/10) of an inch) is provided permitted between the components in the staple firing chain.

This small degree of movement is provided for several reasons as follows: 1) minor pivotal proximal movements of the trigger mechanism will not immediately result in engagement between the pusher assembly and the staple next in line, thus avoiding inadvertent distal movement of the staple during handling by operating room personnel, or positioning by the user; 2) engagement of the pusher assembly with the next staple will not occur until the pawl and ratchet plate of the clutch mechanism (described hereinbelow) takes place, thus preventing inadvertent partial advancement of several staples at a time. This would occur if the operator were allowed to partially activate the trigger mechanism several times over the same part of its cycle. The clutch mechanism prevents such movements. Further, this free movement of the thrust bar 26 also permits the staple advancing and forming components to engage each other smoothly without jamming or intercomponent interference with themselves and with the components of the system for pivoting the staple storage magazine 16 as will be described hereinbelow. Explanation of the pivoting system for the staple storage magazine will illustrate the advantages of the lost motion connector bar in further detail.

Trigger mechanism 20 is pivotally attached at pivot pin 32 for pivotal movement toward and away from handle grip 18, and is adapted to produce upward and downward rotational movement of triangular member 34 when horizontal pin 36, attached to trigger mechanism 20, traverses an upward arc whose center of rotation is located at pivot pin 32. Thus, it can be seen that when handle grip 18 is positioned in the palm of the user's hand and trigger mechanism 20 is squeezed toward handle grip 18, horizontal pin 36 traverses an upward arc while engaging the longer side 34a of triangular member 34 as shown. This movement causes triangular member 34 to rotate upward in a counterclockwise direction while upright member 35 to which it is attached, pivots forwardly about a point of rotation defined by pivot pin 37 located at the lowermost end of a handle grip 18 shown in FIG. 2.

As can be seen in FIGS. 2 and 3, pusher assembly 24 is connected to upright member 35 through aperture 33 such that inward squeezing of trigger mechanism 20 will cause the entire pusher assembly to advance distally against the constant force provided by negator spring 40 as shown. The negator spring 40 is formed of a resilient flat spring material coiled about the rotational bar 42 which is rotationally mounted about cross member 44 which forms part of bracket 46. The free end of negator spring 40 is attached to an anchor pin 48 via aperture 49 as shown, while the spring 40 is normally biased toward the coiled configuration as shown in FIG. 3. It can therefore be appreciated that after squeezing trigger mechanism 20 the full stroke from the position shown in FIG. 3 toward handle grip 18 to the position shown in FIG. 7, release of the trigger mechanism will permit the negator spring 40 to assume control and to return rotational bar 42 to the pre-fired proximal location by the automatic winding action of the negator spring 40 to its original unloaded configuration. This motion in turn causes the entire pusher assembly 24 to return to the proximalmost pre-fired position as shown in FIG. 3. The constant force of negator spring 40 uniquely prevents the natural tendency of the user to rotate the hand as with springs which increase in force when progressing through a full spring cycle.

Referring once again to FIGS. 2 and 3, trigger stop device 50 is attached to trigger mechanism 20 and is configured and dimensioned for engagement with handle grip 18 in a manner to thereby limit the proximal pivotal movement of trigger mechanism 20. Depending upon the particular limits required in the apparatus, trigger stop device 50 can be dimensioned accordingly.

Referring now to FIGS. 4–6, the structure and function of the uni-motion clutch mechanism will be described. This clutch mechanism prevents proximal movement of the pusher assembly in the event the trigger mechanism is released after the squeezing motion of the trigger mechanism and the advancement of the pusher assembly has begun but before the full stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring now to FIG. 4 in conjunction with FIGS. 5 and 6, ratchet plate 52 is fixed to barrel 17 and therefore fixed with respect to the handle housing and possesses a surface defined by a plurality of right angle triangular shaped parallel ridges 56 as shown in FIGS. 4–6. Pawl 58 is rockably mounted for distal and proximal movement with pusher assembly 24 through barrel 17, and is biased toward ratchet plate 52 by resilient wire spring 60 as shown. The location of pawl 58 shown in FIG. 4 corresponds to the pre-fired condition of the apparatus with negator spring 40 in the fully wound position and pawl 58 located proximal of ratchet plate 52. Further, pawl 58 is preferably of stainless steel while ratchet plate 52 is made of brass or other compatible material.

While trigger mechanism 20 is squeezed toward handle grip 18 producing distal motion of the entire pusher assembly 24, pawl 58 engageably slides distally past the ratchet surface 56 of ratchet plate 52 as shown in FIG. 5 such that one corner of the tip 62 of the pawl 58 sequentially engages each right angled ridge of ratchet plate 52 to thereby prevent proximal movement of the pusher assembly in the event the trigger mechanism is released by the operator. The engagement of pawl 58 with ratchet plate 52 provides audible confirmation that the pusher assembly is moving distally since the user will hear a series of progressive audible clicks. This action—which is best shown in FIG. 5—continues with the tip 62 of pawl 58 sliding past the ratchet surface of the ratchet plate 52 until the pawl is positioned distally of the distalmost tooth.

After completion of the staple firing stroke and upon release of the trigger mechanism 20 the pawl 58 moves proximally with the pusher assembly as described under the action of spring 40. The end portion 62 of pawl 58 which is now free, engages the distal end of the ratchet plate 52 causing the pawl to rock to the reverse direction shown in FIG. 6 so as to slide proximally past the ratchet surface of ratchet plate 52 without interference to the proximal movement of the pusher assembly 24. Thus, it can be seen that the clutch mechanism as described will effectively permit squeezing the trigger mechanism 20 toward the handle grip 18 while maintaining all positions midway through the stroke in the event the operator releases the grip, while permitting return motion thereof after the stroke has been completed. The clutch mechanism also allows the operator to advantageously preposition a staple such that the legs of the staple protrude from the distal end of the staple magazine discussed hereinafter, and then to release pressure from the trigger mechanism. The operator may then turn full attention to locating the prepositioned staple in the desired target location, at which point the pivoting of the trigger mechanism may be resumed and the cycle completed. This staple prepositioning greatly facilitates staple placement.

THE STAPLE STORAGE MAGAZINE PIVOTING SYSTEM

Referring to FIGS. 8–14, the system for pivoting the staple storage magazine located at the distal end of the endoscopic section 14 will now be described. FIG. 8 illustrates double knurled finger operable collar 60 which is mounted for rotation with the endoscopic section 14 by inwardly extending pin 62 which is slidably positioned within longitudinal groove 64 in the outer housing half section 14a of endoscopic section 14, as shown in further detail in FIG. 14. Thus collar 60 is readily slidable distally and proximally while pin 62 slides within groove 64. Thus while permitting slidable movement of collar 60, pin 62 prevents independent rotation of collar 60 relative to the endoscopic section 14. Accordingly, when collar 60 is gripped between the user's fingers and rotated, the endoscopic section 14 rotates with the collar.

Figure 11:
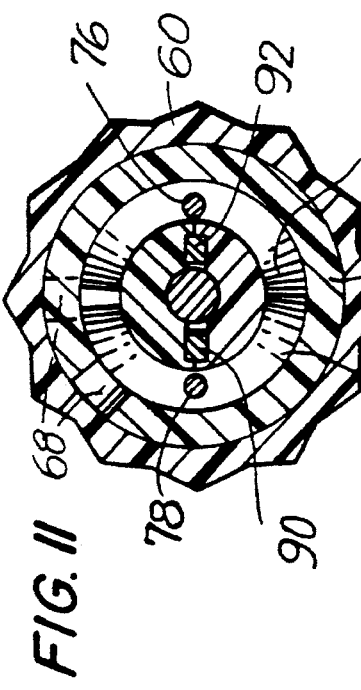
FIG. 11 is a cross-sectional view taken along lines 11—11 of FIG. 9 illustrating further details of the system for providing pivotal motion to the staple magazine at the distal end.

Positioned within finger operable collar 60 is helically grooved inner sleeve 66 fabricated of a suitable plastic material such as nylon, glass filled for strength. Helically grooved inner sleeve 66 is generally cylindrical in shape and includes a helical groove 68 shown in phantom lines in FIG. 8 and illustrated schematically in the projected frontal view of the sleeve shown in FIG. 12. The sleeve 66 is fixedly attached to outer collar 60 for rotation therewith. In the projected view of FIG. 12, the helical groove appears as a diagonal groove having a linear shape. In FIG. 11, finger operable collar 60 is shown in cross-section and the inner helically grooved sleeve 66 is shown whereby helical groove 68 is represented at two locations as viewed in FIG. 11. In FIG. 11, the cross-section of groove 68 at the 10 o'clock position (where lines 11—11 are located in FIG. 9) is just distal of the cross-section of groove 68 shown in phantom at the 12 o'clock position.

Referring now to FIG. 8 in conjunction with FIGS. 9–13, elongated internal cylindrical sleeve 70 is positioned partially within inner helically grooved sleeve 66 and collar 60 when collar 60 is in the distalmost position, as shown in FIG. 8; however, when collar 60 is withdrawn to the proximalmost position as shown in phantom lines in FIG. 8, the major portion of internal cylindrical sleeve 70 is positioned within collar 60 as shown. Internal sleeve 70 is preferably of nylon (preferably glass filled for strength) and defines a distal face 72 which is generally oriented at an acute angle with respect to the longitudinal axis of the instrument as shown clearly in FIGS. 8 and 13. The sleeve 70 contains pin 74 extending radially outwardly from the outer surface as shown. Pin 74 is preferably of steel or it may be formed of nylon integral with sleeve 70. Pin 74 is positioned for slidable movement within the helical groove 68 of inner sleeve 66 of collar 60 such that proximal movement of collar 60 will cause pin 74 to follow the groove 68 causing sleeve 70 to rotate in one direction. Similarly, distal movement of collar 60 to the position shown in phantom lines in FIG. 7 will cause pin 74 to traverse groove 68 in the opposite direction thereby causing sleeve 70 to rotate in the opposite direction.

The significance of the rotational motion of sleeve 70 as it pertains to the pivotal motion of staple storing magazine 16 will be described in further detail hereinbelow. At this stage, however, it is sufficient to state that the obliquely oriented distal face 72 of sleeve 70 engages the proximal ends of a pair of longitudinally extending push rods 76,78 shown in phantom lines in FIG. 13 and more clearly in FIG. 14 such that when collar 60 is moved distally or proximally, inner sleeve 70 also rotates and the rods 76,78 respectively move in equal and opposite directions by the engagement with different portions of oblique distal face 72 with these rods. In essence, one rod is engaged by a surface portion distal of the surface portion on the side of face 72 which engages the other rod. Thus, when the sleeve 70 is rotated in one direction, rod 78 moves in the distal direction while rod 76 withdraws proximally the same distance, and when sleeve 70 is rotated in the opposite direction, rod 76 moves in the distal direction and rod 78 moves proximally the same distance.

Collar 60 contains rotary ridges 60a in the distal half and longitudinal ridges 60b in the proximal half, and is thus conveniently movable longitudinally and rotatably by the user when the appropriate knurled portion is gripped between the user's fingers. However, the operator need not grip the collar 60 at any specific locations. The ridges may be formed integral by molding procedures or alternatively may be in the form of knurled surfaces. The rotary ridges respectively permit collar 60 to be finger movable distally and proximally, while the longitudinal ridges assist in rotation of collar 60 by hand. Rotational motion of the collar causes the endoscopic portion 14 to rotate while proximal movement of the collar in a preferred embodiment causes staple storing magazine 16 to pivot up to about 45 degrees in one direction with respect to the longitudinal axis of the instrument as shown in FIG. 1. Distal movement of the collar 60 to the distalmost position shown in FIG. 8, causes staple storing magazine 16 to withdraw to the original orientation shown in FIG. 1 which is generally in line with the endoscopic section. Thus, by pivoting the staple storing magazine up to 45 degrees and by rotating the endoscopic portion 14, the total range of movement of the staple storing magazine is 45 degrees to either side of the endoscopic section traversing a total of 90 degrees of effective pivotal movement. With respect to movements of collar 60, the direction which produces pivotal motion of staple storage magazine 16 away from the longitudinal axis or toward the axis is clearly a matter of choice and would be determined by the respective configurations of the coacting components.

In the alternative embodiment shown in FIG. 1A, the internal sleeve 70 and forward face 72 are configured such that collar 60 may be positioned midway between proximal and distal positions. The mid-position will correspond to the staple storage magazine being at zero degrees with respect to the longitudinal axis. Collar movement in one direction from neutral will produce up to 45 degrees of pivotal movement of magazine 16 and collar movement in the other direction on the side of neutral will produce pivotal movement of the magazine 16 up to 45 degrees in the other direction. A major distinction in this embodiment is that the actual orientation of the magazine with respect to the longitudinal axis will differ on either side of neutral.

Figure 15:
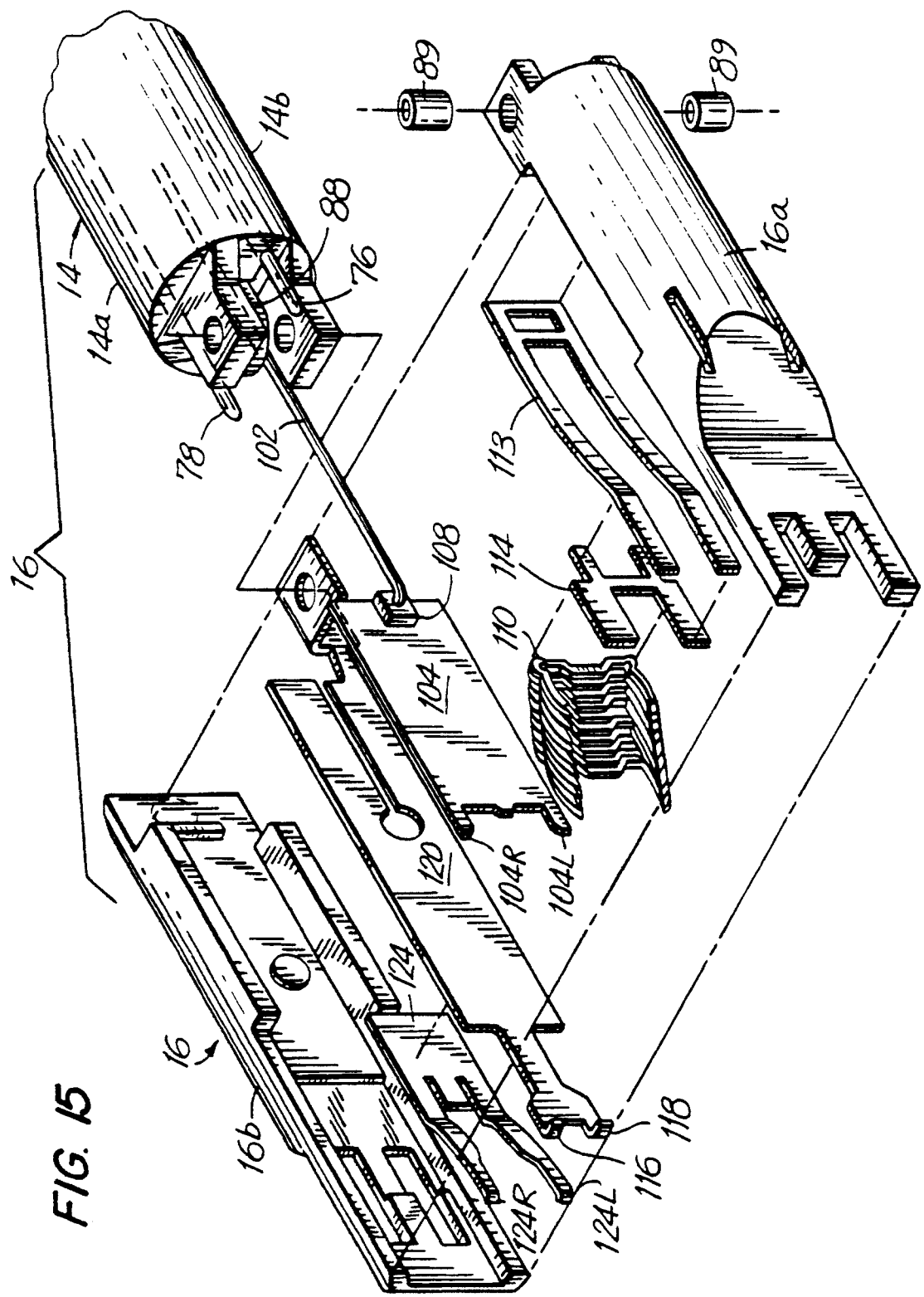
FIG. 15 is an exploded perspective view with parts separated, of the staple storage magazine which is controllably pivotally mounted at the distal end portion of the endoscopic section.

Referring now to FIGS. 15 and 16, the system for providing pivotal motion to the staple storing magazine 16 is illustrated at the distal end of the instrument. In FIG. 16 the staple storage magazine 16 is shown in the position generally in alignment with the endoscopic section and is shown in phantom lines at the pivoted locations corresponding to plus or minus 45 degrees. The staple storage magazine is formed of an outer housing of a suitable plastic material such as polycarbonate and is comprised of upper housing half section 16a and lower housing half section 16b attached by welding, adhesives, etc. The upper housing half section 16a contains an indentation 80 at the proximal end having a "V-shaped" cross section and the lower housing half section 16b contains a similar indentation 82 also having a "V-shaped" cross section as shown. Both indentations 80, 82 are adapted to respectively engageably receive the distal ends of rods 76, 78 (which are rounded) such that when the rods are respectively and alternatively moved in the proximal and distal directions as described hereinabove, one rod may advance distally to cause the upper housing to rotate and the other rod withdraws to permit the pivotal motion of the staple magazine. For example, as shown in FIG. 16, when rod 78 moves distally, engagement of the tip of the rod 78 with indentation 80 in upper housing 16a of staple storing magazine causes the staple magazine to pivot downwardly as shown in phantom.

Similarly, equal and oppositely withdrawing rod 76 will accommodate the downward movement of the staple storing magazine 16. In a similar fashion when the collar 60 is moved in the opposite distal direction the movement of each rod is respectively reversed causing rod 76 to move distally and to engage the lower housing 16b of staple storing magazine 16 and rod 78 withdraws to accommodate the pivotal 0 movement of staple storing magazine back to the original (or neutral) position in general alignment with the endoscopic section as shown in FIG. 16. The lost motion connector 30 clearly provides a minor degree of space (i.e. about 1/10 inch) between the components, which space provides the advantages mentioned previously.

Alternatively one rod may be provided and connected to the staple storage magazine and adapted to pivot the magazine by causing such rod to move proximally and distally thereby actually pivoting the magazine about the pivot point.

The endoscopic section 14 is shown clearly in FIG. 14 and is mounted for rotation relative to the handle section 18. As noted above, the endoscopic section may be permanently attached to handle 12 as shown in a disposable instrument; alternatively as noted above, it may be removably attached to a re-usable handle, or a variety of other combinations or configurations.

THE ENDOSCOPIC SECTION

For purposes of the present description, the endoscopic section is described as the elongated section shown in FIG. 14 extending from the handle to the location of attachment of the staple storage magazine. However, it is clear that reference to the endoscopic section may contemplate the section shown, with or without the staple storage section included.

Referring again to FIG. 14 the endoscopic section is shown in exploded view with parts separated for convenience of illustration and includes upper housing half section 14a and lower housing half section 14B. The housing half sections are preferably of a polycarbonate material such as LEXAN brand material mentioned previously, and are attached by welding, adhesives, etc. Positioned within the upper and lower housing half sections is pusher assembly 24 as described in more detail below, and anvil extension 88, formed of stainless steel and having a pair of elongated legs 90,92 which are joined at 94 at the distal end and which contain upwardly extending feet 88b, 88b at the proximal end. As shown in FIG. 15, anvil extension 88 is attached at the distal end 94 to the staple storing magazine 16 by pivot pins 89 where the staple storing magazine is pivotally attached. The proximal connection points of anvil extension are best illustrated in FIG. 2 wherein upwardly bent feet 88a, 88b are positioned within slots 15b in half round collar 15 which is fixedly attached to handle housing 12 by barrel 17 and nose piece 13 and related support members provided therein.

Anvil extension 88 is fabricated of stainless steel and its purpose is to stabilize the dimension of the endoscopic section 14 to prevent the forces acting on the components from stretching or compressing the upper and lower housing half sections 14a, 14b of the endoscopic section which are constructed of a polycarbonate material such as LEXAN brand material. Thus, the steel anvil extension provides dimensional stability to the endoscopic section while the endoscopic section is supporting the components being subjected to forces for supporting, advancing and forming the surgical staples as will be described.

THE STAPLE FIRING SYSTEM

Referring further to FIG. 14, the staple pusher assembly 24 is formed of firing rod 28 connected to flexible elongated firing wire 102 which is in turn connected to pusher plate assembly 104 as shown. The connection between firing rod 28 and firing wire 102 is a crimped or swaged connection at 106, whereas the connection between firing wire 102 and pusher 105 is accomplished by an interference fit between the firing wire 102 and collar 108 which is attached to pusher plate 104. In an embodiment described hereinbelow, swaging of the collar 108 to firing rod 28 is utilized. Firing rod 28 and pusher plate 104 are preferably made of stainless steel whereas firing wire 102 is made to be resiliently flexible to accommodate the pivotal movement of the staple storing magazine 16 since firing wire 102 is located within the instrument at the location of staple magazine 16. In particular, firing wire 102 is preferably made of a super elastic metal. One preferred example of such super elastic metal is TINEL brand metal available from Raychem Corporation, Menlo Park, Calif. Another example is NITINOL brand metal. This material has a reduced tendency to fatigue after a substantial number of cycles of deflection caused by pivoting the staple storage magazine. Other resilient materials are also contemplated for firing wire 102.

THE STAPLE STORAGE MAGAZINE

Referring now to FIGS. 15 through 18, there is illustrated further details of the staple storing magazine 16. As noted previously, the staple storing magazine 16 is comprised of upper housing half 16a and lower housing half 16b suitably attached by welding, adhesives, etc. The magazine is adapted to contain a plurality of surgical staples 110 which are particularly shaped to penetrate and to attach surgical mesh to body tissue. For particular details of the shape of the staples constructed according to the invention, reference is made to FIG. 28.

Referring once again to FIGS. 15–18, a particular feature of the present invention resides in the system of storage of the staples 110 which are positioned in adjacent stacked relation whereby the stack of staples forms an angle with the longitudinal axis of the instrument of approximately 45 degrees as shown in FIG. 18. One purpose of stacking the staples as shown is to provide greater visibility to the user by the fact that the outer surface of the upper housing half section adjacent the stack of staples forms a similar angle and provides visibility to the user at the distal end of the staple storage magazine. Angular stacking of the staples as shown greatly facilitates storage of a plurality of staples in a structure configured and dimensioned for use in endoscopic applications, e.g. for use through a trocar guide tube of diameter of about 12 mm for example. The stack of staples 110 as shown in FIG. 18 is positioned and retained in such position by a resilient spring member 113 having dual resilient legs and whose side profile is curved as shown in FIG. 18.

The distal end of each leg engages the uppermost staple follower 114 in the form of a nylon insert having a general "H-shaped" configuration and dimensioned sufficient to cover the staples as best shown in FIG. 15. The nylon follower is intended to transmit the downward force of the staple retainer spring 113 so as to distribute the force on the stack of staples in a manner to facilitate a constant and uni-directional downward force on the lowermost staple which is positioned for advancement and deformation. It also functions to advance the stack of staples downwardly when the lowermost staple is fired. Steel anvil plate 120 is shown in FIG. 15 and includes upwardly extending feet 116 and 118 which form anvils at the distal end as shown in FIG. 15, for forming the staple therearound.

Thus, as seen in FIG. 18, the lowermost staple is identified by numeral 110L and is in a position for engagement by pusher plate 104 when the pusher assembly is advanced distally. The pusher plate 104 is shown clearly in FIGS. 15 and 18 and contains distally advancing lands 104R and 104L shown clearly in FIGS. 15 and 19 at the distal end to facilitate transmission of advancing force to the two rounded or arcuate bridge portions of the staple. This relative complementary configuration of the pusher plate 104 and the staple 110 facilitates efficient and uniform distribution of force to the staple when it is deformed about the anvil members as will be described.

THE STAPLE CLOSING SYSTEM

Referring now to FIGS. 17–24 there is illustrated the sequential views of the staple advancing and closing system between the pre-fired and fired condition of the staple. In particular, the staple and pusher mechanism are shown in FIG. 17 in the pre-fired condition while the staple shown in FIG. 24 is embedded within the body tissue in a manner to retain the surgical mesh to the body tissue.

In FIG. 17, the staple pusher assembly 24 is positioned proximal of the lowermost staple 110L and pusher plate 104 is correspondingly positioned proximal of the lowermost staple 110L. In FIGS. 18 and 19 the pusher plate 104 has been partially advanced distally and the lowermost staple 110L has been advanced distally of the stack of staples 110 in a manner such that the pusher plate 104 has now replaced lowermost staple 110L thereby preserving the integrity and position of the stack of staples 110. The preservation of the stack of staples 110 is provided by the fact that the thickness of the staple pusher plate 104 is either identical to or slightly less than the thickness of the staples to assume that the plate 104 will engage only one staple at a time.

Referring further to FIGS. 20 and 21 the pusher plate 104 has now advanced distally sufficient to cause the staple to penetrate the surgical mesh 112 and the body tissue 115. As shown in FIGS. 20 and 21, it can be seen that anvil members 116 and 118 are positioned for engagement by the straight sections of bridge portions 110BR and 110BL of the back rib of the staple 110L such that engagement of the staple by pusher plate 104 with the arcuate end corner portions of the staple as shown will cause the staple to deform in a predetermined manner as will be described.

In FIGS. 22–24 the staple 110L is now shown in the deformed condition about the anvil members 116 and 118 and the straight portions 110S of the back rib of the staple 110 are still in engagement with the anvils 116,118. In FIG. 22, the staple has penetrated into the body tissue 115 and has been deformed and in FIG. 24 the staple deformation is completed in a manner to substantially retain the surgical mesh 112 in attached position with respect to the body tissue as shown in FIG. 22. The inwardly projecting central portion or bight, 110C, of staple 110 is shown gripping the mesh and tissue in cooperation with the staple legs as shown in FIG. 24. However, in FIG. 22 release of the staples from the anvil members 116,118 has not yet been completed.

Release of the staple from the anvil members 116,118 is readily accomplished by ejector spring 124 which is a "U-shaped" resilient spring having upwardly biased legs 124R and 124L each positioned respectively as shown in FIG. 15. When the pusher plate 104 is in the position shown in FIG. 20, the legs 124R and 124L of staple ejector spring are retained in a downward position by lands 104R and 104L of the pusher plate 104. However, when the pusher plate 104 is moved to the distalmost position shown in FIG. 23, the absence of the pusher plate permits staple ejector legs 124R and 124L to resiliently deflect upwardly to their natural configuration thereby creating a vertical separation between the anvil members 116,118 and the deformed staple, thus releasing the deformed staple from the anvil members as shown in FIG. 23. Continued proximal movement of the pusher plate 104 causes withdrawal of the pusher plate to a position entirely proximal of the stack of staples 110 as shown in FIG. 26, causing the stack of staples to move downwardly due to the downward force of resilient staple retainer spring 113 to advance the lowermost staple to the firing position.

Once the staple 110 is applied to the mesh 112 and tissue 115 as shown in FIGS. 22 and 24, the distal end of staple storing magazine 16 is withdrawn as shown in FIG. 24 and preparation is made for application of the next staple. FIG. 25 is a cross-sectional view taken along lines 25—25 of FIG. 24 with the staple storing magazine withdrawn from the surgical mesh and body tissue. Thereafter, the apparatus may be repositioned to apply another staple, or even an array of staples as shown in FIGS. 27 and 29.

Referring once again to FIG. 27, there is illustrated one form of surgical mesh repair of an opening in the body utilizing the apparatus and staple according to the invention. In the application shown in FIG. 27, a surgical mesh is attached to the body tissue over the opening as illustrated schematically at 115c in FIG. 27, and staples 110 have been applied in a circular array as shown to reinforce the repair. Beneath the mesh, the opening 115c may have previously been repaired as well. In FIG. 29 an alternative array of staples to apply mesh material to body tissue is shown. In this embodiment the mesh material 112 is essentially formed as a circular patch and staples 110 are oriented in a radial direction and are attached around the periphery of the patch such that one leg of the staple pierces the mesh and the other leg pierces body tissue 114. Essentially the staple bridges the periphery of the mesh material as shown. Clearly, alternative forms and arrangements are available to attach mesh or other surgery related objects or prostheses to body tissue as may come to the mind of persons skilled in the art.

It should be further noted that the repair of body tissue utilizing surgical mesh as shown in FIGS. 27 and 29 are exemplary, and that other applications of mesh and staples may be utilized in a manner to either reinforce a surgical repair or to encourage tissue growth. Such mesh materials are typically disclosed in U.S. Pat. Nos. 4,838,884, 4,665, 221, 4,452,245, and 4,347,847. It is noted that the staple constructed according to the invention as shown in FIG. 28 is particularly adapted for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple of the present invention may be applied to attach other objects to body tissue as may come to the mind of those skilled in the art.

THE STAPLE

Referring now once again to FIG. 28, there is illustrated the inventive staple 110 constructed according to the invention. The staple 110 is particularly shaped as shown, and is preferably formed of a length of wire of titanium. Stainless steel or equivalent material is also contemplated and the staple preferably has a rectangular cross-section as shown. Other cross-sections may be used. Typically, the wire will be about 0.38 mm in width (dimension W) and 0.51 mm in thickness (dimension T). The initial width of the staple before closure (dimension A) is about 4.4 mm and the thickness dimension between the back rib and legs after closure (i.e. dimension B in FIG. 24) is about 3 mm. Another example is a wire having a width of about 0.51 mm (dimension W) and a thickness of about 0.38 mm (dimension T). The width before closure (dimension A) is about 8.64 mm and the thickness between the back rib and legs after closure is about 2.5 mm (dimension B in FIG. 24). The staple 110 has a central bight portion 110c and a wire leg member 110R and 110L extending generally perpendicular to the central portion as shown. Each leg member 110R, 110L is connected to the central portion 110c by a bridge portion 110BR, 110BL having an arcuate corner portion as shown. Each leg member has a sharp tip for penetrating mesh and body tissue. Right leg member 110R further possesses a tapered surface 110TR at the tip which is opposite the position of the tapered surface 110TL at the tip of the other leg member 110L as shown in FIG. 28.

When the staple shown in FIG. 28 is advanced toward dual spaced anvils 116,118 as shown in FIG. 21 for example, and staple pusher plate 104 as shown, engages the arcuate portions of the bridge portions 110BR and 110BL, the legs of the staples are made to fold inwardly toward each other as shown for example in FIG. 22, with one leg crossing over the other. The cross-over configuration is automatically assumed by the legs because of the presence of tapered surfaces 110TR and 110TL which act as camming surfaces tending to bias each leg away from the other thereby tending to cross the legs in the manner shown. This structure also prevents interference of the legs when folded toward each other.

Thus, it can be seen that the particular shape of the staple as shown, promotes a unique folding pattern for the legs which achieves the configuration shown in the bent staples of FIGS. 22 and 24. Note in particular that inwardly bent central portion 110c promotes positive attachment of the mesh to the tissue by providing a gripping system between inwardly projecting bight portion 110c and leg members 110R and 110L with mesh and tissue gripped therebetween. This staple shape combines with the arrangement of the anvils and the particularly configured pusher plate 104 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pierces folds and grips in substantially a single movement.

In practice, the laparoscopic procedures to repair tissue in hernia repair using surgical mesh is similar in some respects to the surgical procedures to gall bladders, appendix, lungs, etc. In particular, the endoscopic tubular section of the apparatus is inserted into the cannula which is positioned within the opening in the body. Provision is made between the cannula and the endoscopic section to seal the connection therebetween and provision may also be provided to seal the actual endoscopic apparatus from leakage of fluids or insufflating gaseous media. An exemplary cannula assembly including seal means is disclosed for example in commonly assigned U.S. Pat. No. 4,943,280, issued Jul. 24, 1990, the disclosure of which is incorporated herein by reference.

THE KIT

The present invention is readily adaptable to be provided to surgeons in the form of a kit in which all necessary equipment and accessories are provided in sterile form ready for use in surgery. For example, an apparatus constructed according to the invention can be readily packaged with a supply of staples (i.e. up to 12 or more staples) and sufficient mesh material for completing the hernial repair. The mesh material is typically about 1 mm in thickness. The components may be provided separately as a matched kit, or in a blister type or other package, suitable and ready for use by the surgeon and the surgeon's assistants. The apparatus and staples can be provided in any size matched to meet the apparatus and mesh material in accordance with the particular needs of a contemplated hernial surgical procedure. In addition, the kit can include a matching trocar assembly with appropriate valve assembly to prevent loss of the insufflating gas from the peritoneum between the trocar and the outside surface of the endoscopic section. Since the outer housing of the endoscopic section is substantially closed at the point of attachment of the staple magazine, release of insufflating gases through the staple magazine and the endoscopic section housing is either non existent or minimal. Such trocar assembly is available from United States Surgical Corporation, Norwalk, Conn., under the trademark SURGIPORT brand trocar assembly.

A typical endoscopic section may be a 12 mm diameter with a staple magazine capable of holding up to 10 staples of appropriate size. The length of the endoscopic section is typically 14 to 15 inches. An endoscopic section in the embodiment shown will be about 14 inches. However, if pivotal movement of the staple storage magazine is to be provided between plus 45 degrees and minus 45 degrees solely by distal and proximal movement of collar 22, the endoscopic section will be structured to greater in length, i.e. about 15 inches. The trocar assembly will be of matching size, i.e. 12 mm, to accommodate the endoscopic section and to prevent release of gases thereby. The mesh material provided with the kit will be of mesh size comparable for use with the size of the staples provided in the kit.

Thus by structuring the apparatus to provide such sealing, the endoscopic application of staples to attach objects such as surgical mesh to body tissue can be readily accomplished. Accordingly, the present invention is not only directed to the apparatus for applying such staples to body tissue, but also to a kit in which the apparatus is uniquely combined with a supply of staples, surgical mesh, cannula assembly etc. whereby the surgeon may readily perform the necessary procedures.

AN ALTERNATIVE EMBODIMENT

In the following description of an alternative embodiment of the invention, like components will be identified by numerals similar to the numerals for like components in the previous embodiments except that they will be preceded by the numeral "2". Accordingly, for example, the entire apparatus of the previous embodiment was identified in the description as numeral "10". In FIG. 30, for example, the apparatus is identified by numeral "210".

Figure 33:
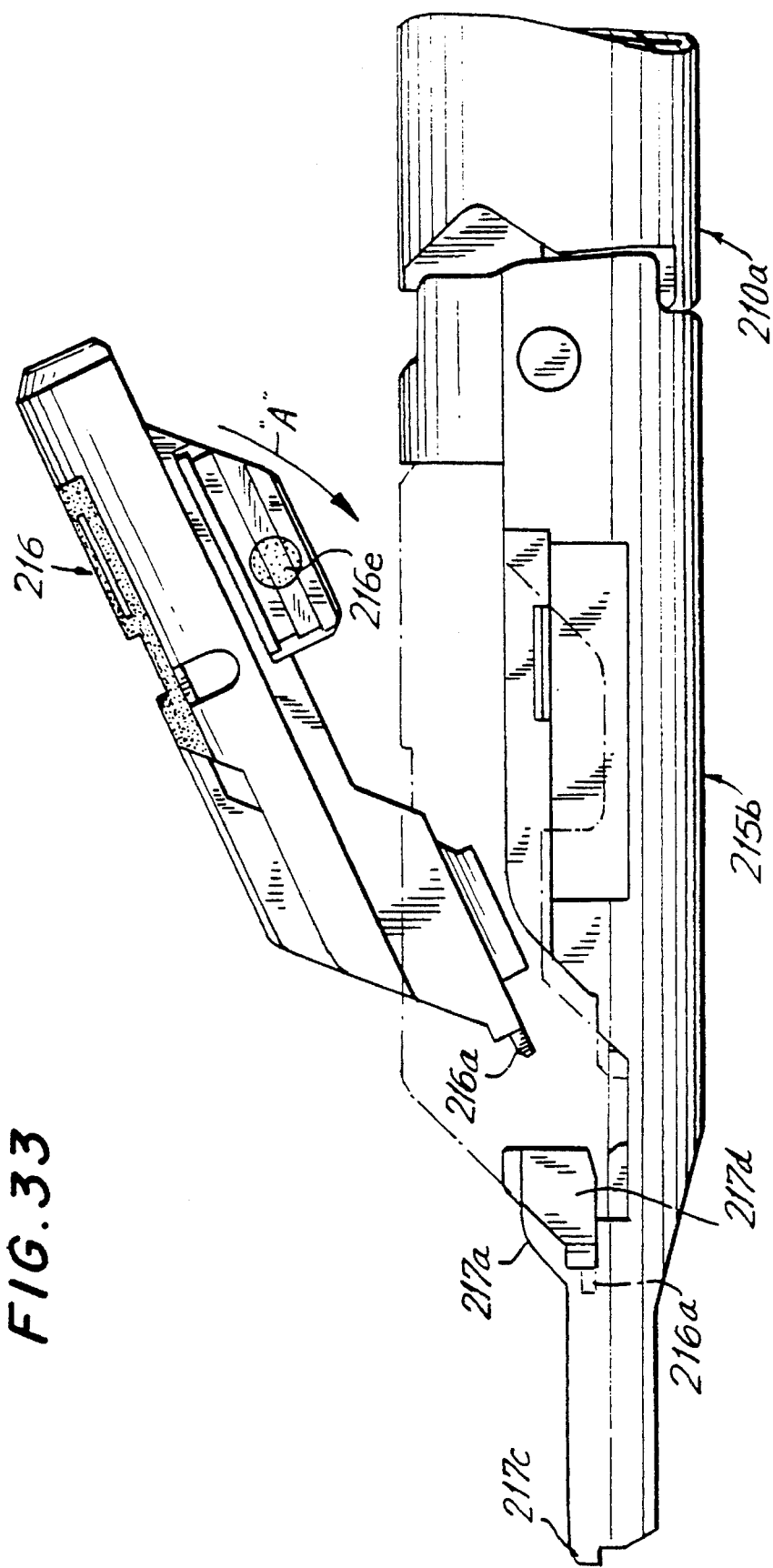
FIG. 33 is a side elevational view of the distal portion of the endoscopic section illustrating the staple storage cartridge support member and the staple storage cartridge in position for insertion onto the support member.
Figure 37:
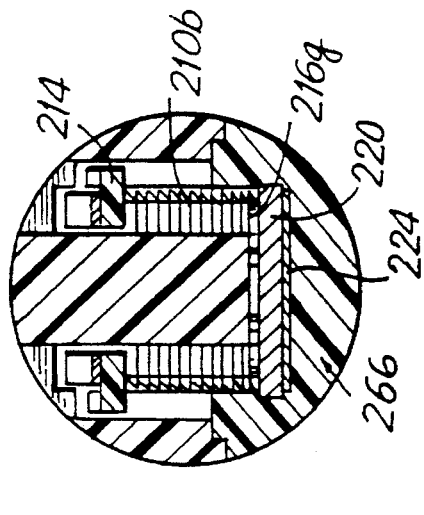
FIG. 37 is a cross-sectional view taken along lines 37—37 of FIG. 35 illustrating the staples stacked within the cartridge.

Referring now to FIG. 30, there is illustrated a perspective view of an alternative embodiment of the apparatus constructed according to the invention in which the staples are stored in a cartridge which is self-contained and which is readily insertable at the distal portion of the endoscopic section of the apparatus as shown in FIG. 33. The apparatus 210 includes handle portion 212 and endoscopic section 210a having at the distal end portion a staple storage cartridge support means 266 on which is supported staple storage cartridge 216. Generally, it may be stated that the staple cartridge support member 266 is pivotally mounted to the distal portion of the endoscopic section and such pivotal motion will result in similar pivotal motion of the staple storage cartridge 216 since the cartridge is directly supported by the pivotal support member. The pivotal motion of the staple storage cartridge support member and related mechanism is identical to the mechanism described previously in connection with the first embodiment.

Referring now to FIG. 31 the components which form the handle 212 are shown and are in many respects identical to the components and function of the handle shown in FIG. 2. The handle components shown in FIG. 31, however include an additional feature which provides a manual tactile feel to assist the user in knowing when the staple is at a particular visible position shown in FIG. 39. One way this can be achieved is shown in FIG. 31 whereby arcuately shaped notch 233 is incorporated into the triangular member 234 and is configured and dimensioned similar to the pin 236. When trigger 220 is manually squeezed by the user toward upright member 235 causing horizontal pin 236 to traverse an upward arc as described in connection with the previous embodiment the pin 236 engages the longer side 234a of triangular member 234. Thus, each time the trigger 220 is squeezed a sufficient distance, the pin 236 will enter arcuately shaped notch 233 so as to provide the user with an actual indication by feel of the location of the pin with respect to the longer side 234a of triangular member 234. At this point along the path of pin 236 the staple 210b, next in line, will be at the same partially advanced distal location which is shown in FIG. 39.

Thus, when the user senses or feels the detent of the entry of pin 236 into notch 233 an actual perceptible tactile indicator of the position of the staple next in line is thus provided. This partially advanced position of the staple facilitates visual examination of the staple to assist the user in selecting the proper position or location and/or orientation which would be appropriate for the particular staple application which is in progress. At all times, however, while trigger 220 is being squeezed, the uni-motion clutch mechanism 200 will prevent retracement of the trigger until the full stroke has been completed, as described previously. It should be noted that other means, including visible and audible, can be utilized to achieve the advantageous provision of indicating to the user when the staple is in its partially advanced position.

Referring now to FIGS. 32 and 32A, the unique replaceable staple cartridge system constructed according to the present invention is disclosed. In contrast to the embodiment described hereinabove the staple storage magazine and pivoting system has been replaced by the combination of a replaceable staple storage cartridge 216 shown with parts separated in FIG. 32A and a pivotal staple cartridge support system 215b shown with parts separated in FIG. 32. In summary, the pivotal staple cartridge support system is permanently attached for pivotal movement via pins 289 with respect to the endoscopic section 210a and the cartridge 216 is readily insertable with respect to the support system as shown in FIG. 33.

Referring once again to FIG. 32 the staple cartridge support system includes support member 266 having proximal upper face member 215 permanently attached thereto by ultrasonic welding, gluing etc. The entire assembly is attached for pivotal movement to endoscopic section 210a via pins 289. As described in the previous embodiment the pivotal movement of the staple cartridge support member 266 and related components is capable of extending up to about 45° with respect to the central axis of the endoscopic section 210a. However, as noted previously this cartridge support system may be arranged to pivot from about +45° to about −45° by dimensioning the pivoting system appropriately.

The pivotal movement of the staple cartridge support system shown in FIG. 32 is identical in all respects to the pivotal movement of the staple storage magazine described in connection with the previous embodiment and shown particularly in FIG. 15. However, in the staple cartridge support system in FIG. 32 the structure has been modified as shown to accommodate the removable and replaceable staple cartridge 216. For example, at the distal end portion of the staple cartridge support system there is shown cartridge support plate 217 which includes a lip 217a at the proximal end for reception of the distal tips 216a of the cartridge housing to retain the cartridge 216 in position on the support member 266. In addition cartridge support plate 217 includes distally extending leg members 217b which in turn include tip portions 217c which extend distally of the tip of cartridge support member 266 as shown more clearly in FIG. 33. The tip members 217c extend not only distally but also inwardly as shown clearly in FIGS. 32 and 34 so as to provide an increased staple contact surface and backing support for each staple as it is advanced distally and as it is deformed. This feature prevents the staple from curling rearwardly as it is being deformed in the event such tendency may be present. Thus, this feature provides resistance to backward roll for each staple.

Referring once again to FIG. 32a and FIG. 32b the cartridge 216 is shown and is assembled to contain a plurality of staples which are preloaded and a spring 213 having distally extending legs 213a adapted to bias staples 210b in a direction toward the anvil 220 via staple follower 214 constructed of a suitable material such as nylon. The staples are contained in cartridge 216 by "L" shaped holders 216g on the lower face of the cartridge 216 as shown in FIG. 32B. In the present embodiment, the staple follower 214 is similar to staple follower 114 of the previous embodiment but contains a proximally extending extension 214a terminating in head 214b which extends into the space 213b defined by the legs 213a of spring 213.

Figure 36:
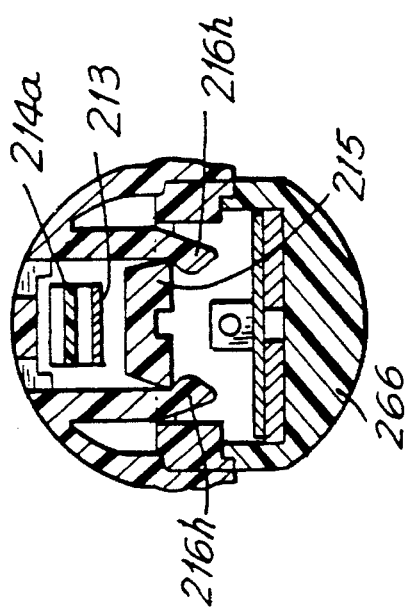
FIG. 36 is a cross-sectional view taken along lines 36—36 of FIG. 35 illustrating the initial position of the staple indicator when the cartridge is loaded with a full complement of staples.

The cartridge 216 is inserted into position as shown in FIG. 33 and is retained by positioning distal tips 216a into respective spaces 217e formed on each side between face member 215 and cartridge support member 266. Central partition 217d becomes positioned within the space 216k between cartridge distal legs 216L to stabilize the cartridge in position. Downwardly extending cartridge legs 216h shown more clearly in FIGS. 34, 35 and 36 are configured as shown, to resiliently snap into elongated apertures 215a in face member 215 as shown in FIG. 36 to retain the cartridge in position when it is rotated thereinto in the direction of arrow A as shown in FIG. 33. Thus, it is preferable to fabricate the housing of cartridge 216 of a resilient plastic material.

Figure 38:
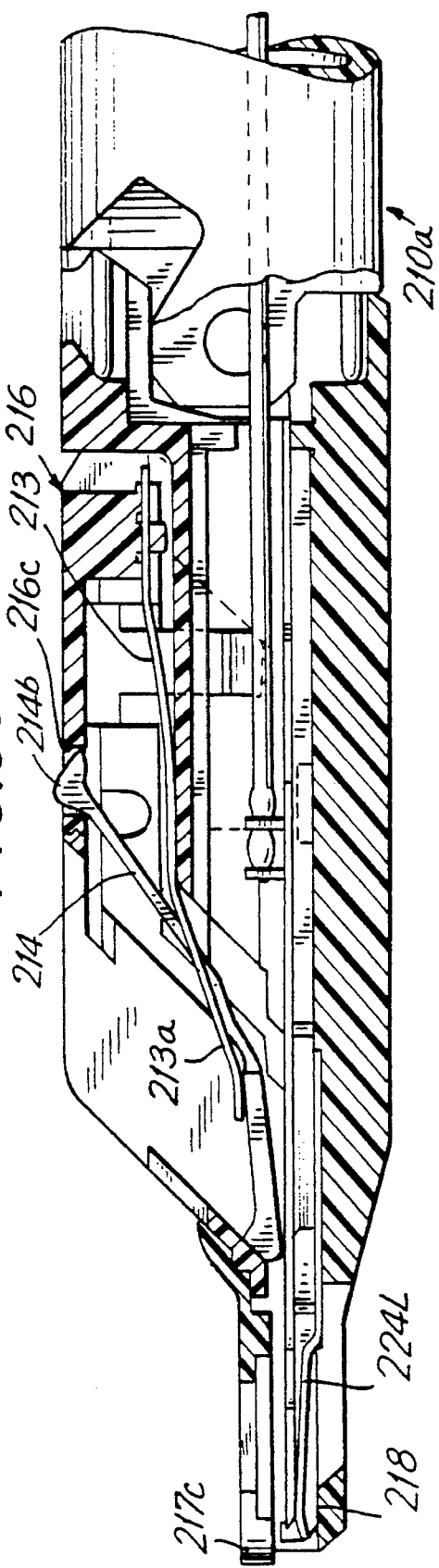
FIG. 38 is a cross-sectional view of the staple storage cartridge and related support member after the last staple has been fired.
Figure 44:
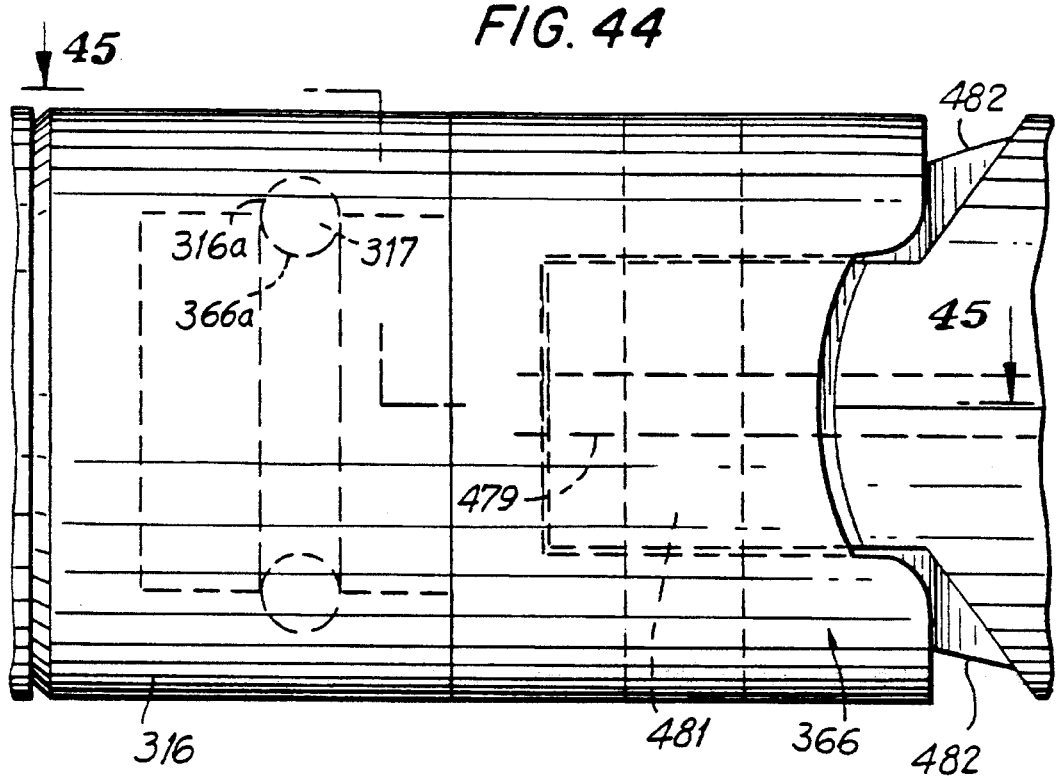
FIG. 44 is a view taken along lines 44—44 of FIG. 42, illustrating in phantom lines the pivoting system for the staple storage magazine section and related attachment system.
Figure 45:
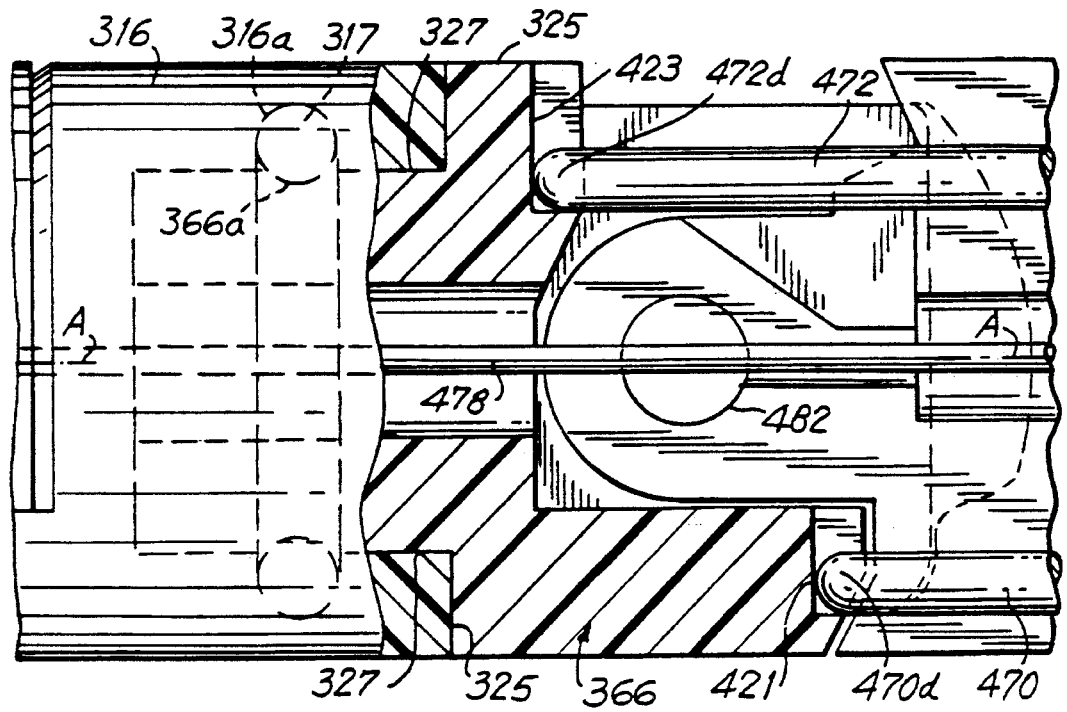
FIG. 45 is a partial cross-sectional view taken along lines 45—45 of FIG. 44, illustrating the system for pivoting the staple storage magazine section at the distal end portion of the endoscopic section.

The operation of the staple follower 214 is clearly illustrated in FIGS. 35 through 38. In FIG. 35, the staple cartridge 216 is shown with a full complement of staples 210b and the proximal portion 214a of staple follower 214 is shown extending upwardly through the legs 213a of spring 213. A window 216c is provided in the upper housing 216b of cartridge 216 to facilitate visibility of the staple follower when all staples have been spent and the proximal head 214b of staple follower 214 moves upwardly into the window 216b as shown in FIG. 38, by the action of spring 213. Thus, the user is provided with an immediate visible indicator when all staples have been spent.

In addition, it is desirable to fabricate staple follower 214 of a bright colored plastic material such as nylon. For example, follower 214 could be fabricated of a bright yellow material at least at the head 214b such that a visible indication will be provided by head 214b after the last staple has been spent. In assembled condition, the head 214b and extension 214a will be positioned in space 213b between legs 213a of spring 213 as shown in FIGS. 35 and 38. In addition, it is desirable to color the area 216d of upper housing 216b of the cartridge 216 in a color similar to the color of the extension 214a of follower 214. For example, follower 214 may be colored black in its entirety with the exception of head 214b which would be colored bright yellow. Other color combinations may be used.

The area 216d of the upper housing 216b (shown by the stippled portions in FIGS. 32A and 34) can also be colored black. Thus, when a full complement of staples 210b is provided as in FIG. 35, the black portion of extension 214a of follower 214 will appear through window 216c and this black color will complement the black colored area 216d shown by stippling in FIG. 34. Follower 214 is fabricated of a resilient material such as nylon and is configured to be upwardly biased against the inner ceiling 216j as the staples are individually dispensed. When the last staple has been dispensed and closed as shown in FIG. 38, the yellow colored head 214b of follow 213 will snap upwardly under its own resilience to thereby appear through window 216c and the user will therefore be provided with an immediate visible indication that the last staple has been spent. Thereafter, the cartridge may be simply removed by lifting it away from the pivotal support member 266 in the direction opposite the direction shown by the arrow A shown in FIG. 33. The cartridge may be replaced by a fully loaded cartridge and the surgical operation may proceed.

Another feature of the cartridge of the present invention is the provision of colored circular dots 216e and 216f. One of each such circular dot is shown on upper cartridge housing 216b by circles surrounded by stippled areas in FIGS. 32A and 33. By placing the user's thumb and first middle finger on the two dots 216e on each side of the upper housing 216b, and the index finger on the forward dot 216f, the cartridge may be simply lifted from the pivotal support member 266 causing cartridge legs 216h to release their snap grip on face member 215. Thereafter, a full cartridge may be replaced in the same, but reverse fashion by positioning tips 216a into space 217e and snapping legs 216h into position with apertures 215a. The circular dots 216e and 216f can be provided in any suitable color which is readily observable to the user. For example, these circular dots may be provided in the color black, which would be readily visible in contrast to the yellow indicator of head 214b of staple follower 214.

Figure 13:
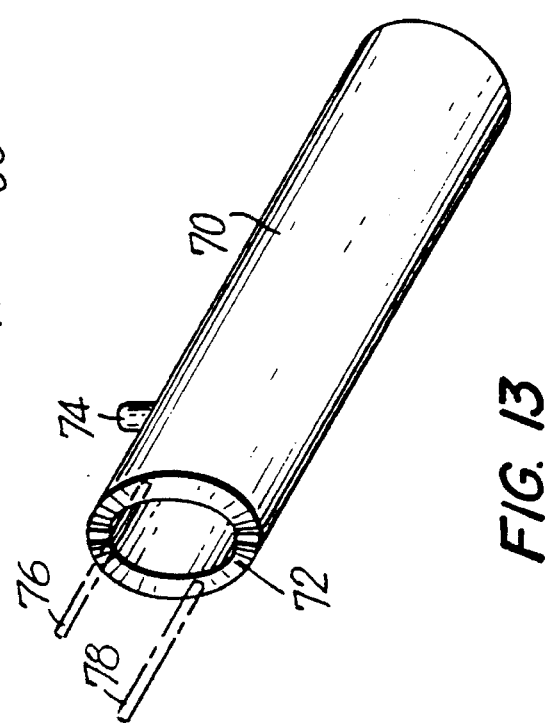
FIG. 13 is a perspective view of an internal sleeve and pin which coacts with the inner sleeve shown in FIGS. 11 and 12 which forms part of the system for pivoting the staple magazine at the distal end.

Referring now to FIG. 40, there is illustrated a circular sleeve 270 similar to the circular sleeve 70 shown in FIG. 13 in connection with the previous embodiment. The circular sleeve 270 is identical in all respects to the cylindrical sleeve 270 of the previous embodiment and is configured as a camming surface adapted to engage push rods 276, 278 to pivot the cartridge support member 266 and the staple cartridge 216 in the same manner as described in connection with the previous embodiment.

In FIG. 40 grooves 270a and 270b are illustrated to provide a positive stop which corresponds to the engagement of push rod 276, 278 with grooves 270a and 270b when the staple storage cartridge support system 266 is in the pivotal position, i.e. approximately 45° with respect to the endoscopic section. The positive stop which is provided by the engagement of the push rods 276, 278 with the grooves 270a and 270b is identical to the operation of sleeve 70 described in connection with the previous embodiment. However, optionally additional grooves 270c and 270d may be provided in sleeve 270 corresponding to pivotal locations of the cartridge support member 266 which are less than the full pivotal movement of the support system, i.e. 25°. These optional grooves will facilitate providing a perceptible tactile indication to the user of the location of the cartridge and related support system in terms of pivotal angle with respect to the endoscopic section. Optionally any number of such grooves may be provided dependent upon the particular needs of the user and the particular surgical procedures required. Thus, the instrument may be provided with any number of combinations of the above-described features.

FIG. 41 is a cross-sectional view taken along lines 41—41 of FIG. 30, illustrating schematically a gaseous seal means in the form of silicone grease 250 to prevent the insufflating gaseous media from escaping from the patient's body cavity through the instrument. Such gaseous seal means may alternatively be in the form of a separate seal block positioned within the endoscopic section, or it may alternatively be in the form of a gaseous sealing block located either at a proximal portion of the endoscopic section or in another portion of the endoscopic section or alternatively in the handle section.

The embodiment described above may be incorporated into kit form as in the previously described embodiment. Also, combinations of features of the present embodiment may be combined with features described in connection with the previous embodiment as may become apparent to persons skilled in the art.

OTHER ALTERNATIVE EMBODIMENTS

In the description of the alternative embodiments which follows, reference is made to FIGS. 42–63 in which, wherever possible, like components are identified by numerals similar to the numerals for like components of the previous embodiments except that they begin with the numeral "3". Accordingly, for example, whereas the entire apparatus for the previous embodiments were respectively identified by numerals "10" and "210", the present embodiment illustrated in FIG. 42 is identified by numeral "310". In addition, for convenience of illustration, certain components will be identified by three digit numerals beginning with the numeral "4" and where possible, by three digit numerals beginning with the numeral "5".

Furthermore, the features described in connection with the present embodiment are contemplated to be complementary to the features and improvements described previously. Accordingly, those features described in connection with the previous embodiments which are incorporated herein need not be repeated. For example, one magazine for storing staples is preferably a removable and replaceable cartridge as shown in FIG. 33 of the previous embodiment and the description thereof is not repeated herein. However, it is also contemplated as another mode of storing and applying staples to incorporate a permanently attached magazine as shown for example in FIGS. 1 and 15. That system need not be repeated herein since reference is made to the description hereinabove.

Referring now to FIG. 42, there is illustrated a perspective view of an alternative embodiment of the apparatus constructed according to the invention. In general, the apparatus of the present embodiment is similar in most respects to the apparatus of the previous embodiments, but incorporates the following additional features:

1. Pivotal movement of the staple storage magazine section to 32.5° and 65° respectively via a double knurled collar similar to collar 60 shown in FIGS. 8–14;

2. Dual detent mechanisms to positively establish the positions of the staple storage magazine section in either of the 0°, 32.5° or the 65° positions; and 3. Independent rotational capability with control from a proximal location, of the staple storage magazine section to rotate about its own central axis in all angular orientations.

The combination of the above-listed features provides extremely precise positioning of the staples at numerous angular orientations to facilitate application thereof at the precise location and orientation which may be predetermined by the surgeon. These features, combined with the features described in connection with the previous embodiments, individually or in combination, provide an apparatus which represents a significant improvement over the highly effective embodiments described previously.

Referring now to FIG. 42, there is illustrated a perspective view of apparatus 310 constructed according to the present embodiment. The apparatus 310 includes frame portion 312 and endoscopic section 314 having at the distal end portion a staple storage section 315 which includes staple cartridge support member 366 on which is supported staple storage cartridge 316. Generally, the frame portion 312 supports the actuating components as described hereinabove in connection with the previous embodiments. Preferably, the frame portion is configured as a handle as shown, grippable by hand. Generally, it may be stated that the staple cartridge support member 366 is pivotally mounted to the distal portion of the endoscopic section and such resultant pivotal movement will result in similar pivotal movement of the staple storage cartridge 316 since the cartridge is directly supported thereon. The pivotal movement of the staple storage cartridge support member and related mechanism is somewhat similar to the system described in connection with the previous embodiments with the additional features described hereinbelow.

The mechanism for pivoting the staple storage cartridge between positions of 0°, 32.5° and 65° with respect to the central longitudinal axis of the endoscopic section is illustrated generally in FIGS. 43–55. In particular, the operation is described to pivot the cartridge via dual knurled collar 322. The appropriate dimensions of the links, the rods and related components have been selected to effect pivotal movements of the staple storage magazine section to about 32.5° and about 65°. However, the relevant dimensions and mechanical advantages may be selected to provide other alternative angular orientations for the staple storage section.

Collar 322 includes dual gripping knurled surfaces similar to the collar described in connection with the previous embodiments. The distal knurled surface 322a facilitates distal and proximal movement of the collar and the proximal knurled surface 322b facilitates rotational movement of the collar about the central axis of the endoscopic section.

Figure 46:
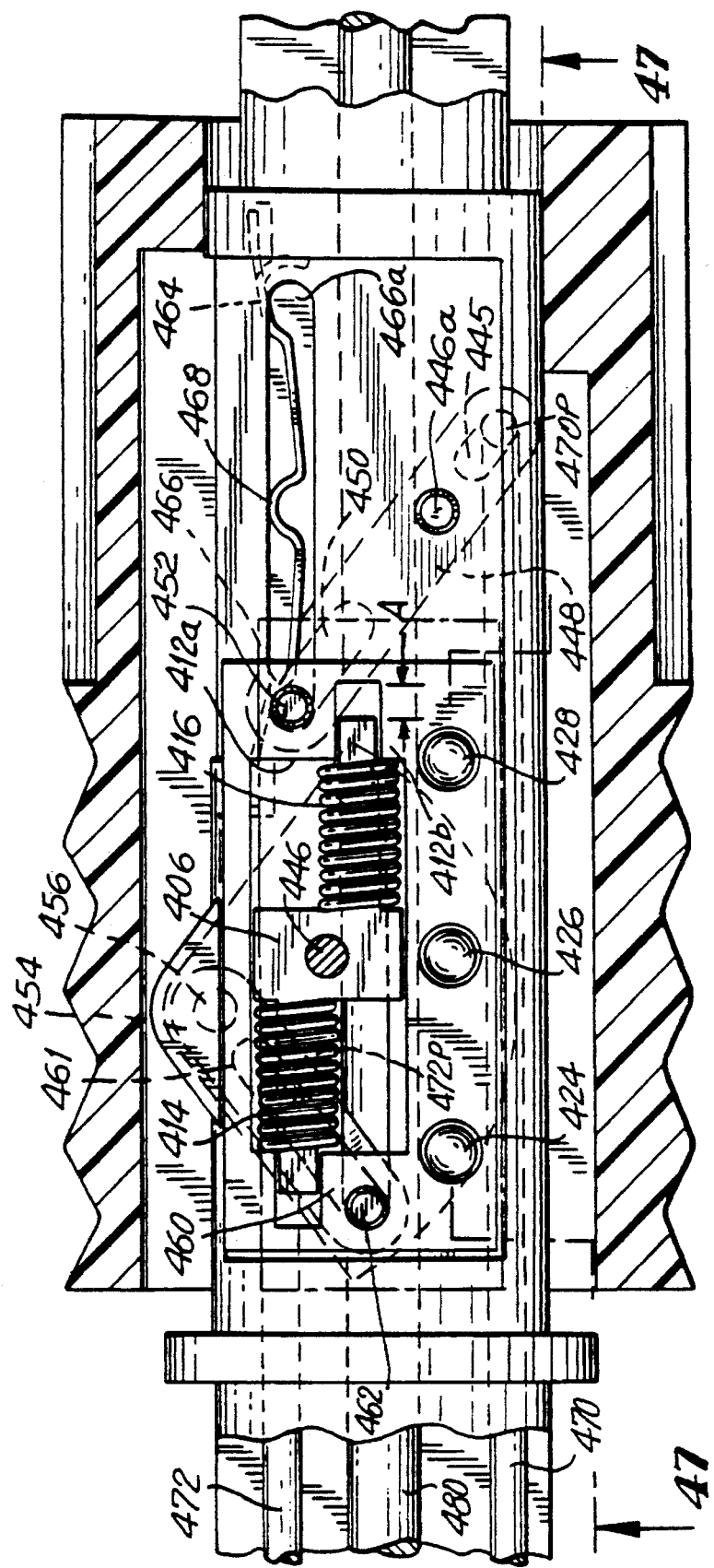
FIG. 46 is a cross-sectional view taken along lines 46—46 of FIG. 42, illustrating the slidable collar and related mechanism for articulating the staple storage magazine section, wherein the magazine section is at the 0° position with respect to the longitudinal axis of the endoscopic section.

Referring in particular to FIG. 43, collar 322 is structured and dimensioned to contain a series of plates including an upper plate 402, a lower plate 404 and a central centering plate 406 having distally extending leg 408 and proximally extending leg 410. Lower plate 404 includes a cut-out 412 which is dimensioned and configured to receive intermediate centering plate 406 as shown in FIG. 46 with legs 408 and 410 respectively surrounded by coil springs 414 and 416. When the plates are assembled and positioned within opening 322c in collar 322 as shown in FIG. 46 centering springs 414 and 416 serve to maintain the centered position of intermediate centering plate 406 within the cut-out 412 of lower plate 404.

Figure 47:
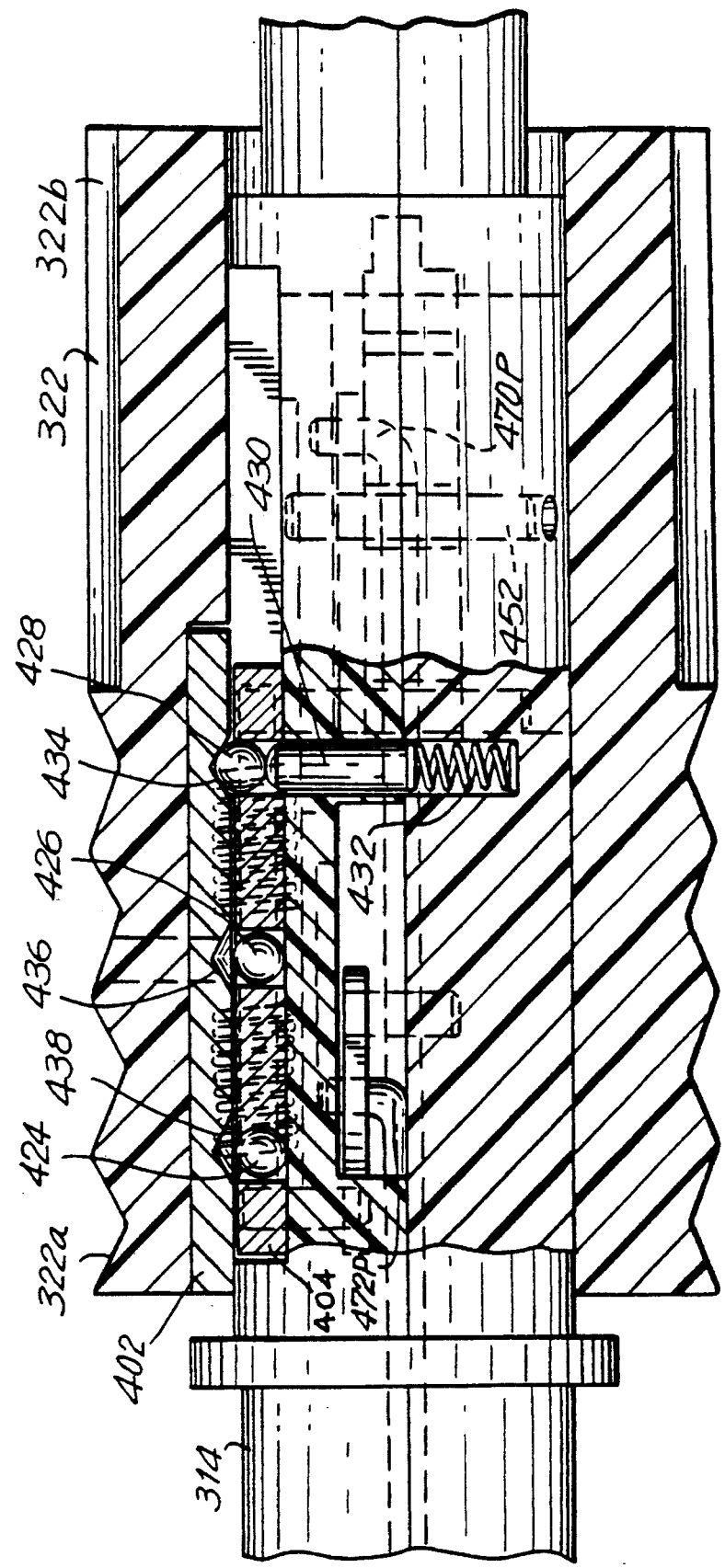
FIG. 47 is a cross-sectional view taken along lines 47—47 of FIG. 46, illustrating the first selective detent mechanism for articulating the staple storage magazine section between 0°, 32.5° and 65°, respectively.

Referring once again to FIG. 43 in conjunction with FIG. 47, lower plate 404 contains cylindrical apertures 418, 420, 422 in which are positioned locator balls 424, 426 and 428. Depending upon the position of the lower plate 404 with respect to the lower housing 314b, pin 430 is biased upwardly by spring 432 to position the ball within the respective conical aperture 434, 436, 438 to locate and fix the position of upper plate 402.

Referring now once again to FIG. 43, pin 440 extends through aperture 442 in collar 322 and through aperture 444 in upper plate 402 as well as through aperture 446 in central plate 406 to key these components together for common distal and proximal movement. In FIG. 43, proximal link 444a is pivotal about pin 446 which extends through aperture 448 in link 444, aperture 467 in upper housing 464 and aperture 315 in lower housing. The link 444 contains slot 450 for slidable reception of pin 452. Pin 452 is slidable distally and proximally within slot 466a in lower housing 464a and also extends through aperture 404d in lower plate 404. Similarly, distal link 454 is pivotal about pin 456 which extends through aperture 458 and contains slot 460 for slidable reception of pin 462. Pin 462 is slidable proximally and distally in slot 468a in upper housing 464a and which also extends through aperture 404c in lower plate 404.

Detent spring 463 contains three arcuate relief sections including distal arcuate detent relief 466, proximal detent relief 464 and intermediate U-shaped detent relief 468 for respective engaged resilient reception of proximal slidable pin 452 as shown in FIGS. 43, 46, 47 and. 49. Links 444 and 454 respectively receive the bent "L-shaped" end 470p and 472p of drive rods 470 and 472 respectively, each of which are respectively arranged at their distal ends 470d and 472d to engage wall portions 421, 423 of the cartridge support member 366 to effect pivotal movement of the cartridge section as rod 472 is moved proximally and rod 470 is moved distally to effect pivotal movement of cartridge section 315.

The operation of the system to effect pivotal movement of the staple cartridge section will now be described. When collar 322 is in the distalmost position, the staple cartridge 316 is at 0° relative to the longitudinal axis of the endoscopic section, i.e. in line with the section 314 as shown in solid lines in FIG. 42. In this position, pin 452 is engageably nestled within distal spring detent 466 as shown in FIG. 46 while proximal link 444 and distal link 454 are positioned as shown. The engaged nestled position of pin 452 in spring detent 466 provides a first detent to retain cartridge push rods 470 and 472 from movement thereby securing the 0° angular position of the staple cartridge section. In addition as shown in FIG. 47, locator ball 428 is positioned within conically shaped indentation 434 in upper plate 402 to provide a second detent mechanism to restrain movement of push rods 470 and 472 by upper plate 402 against proximal and distal movements. Thus, the 0° position of cartridge 316 is established and fixed by a dual detent system.

Referring now to FIG. 46 in conjunction with FIGS. 43–49, the mechanical movements required to produce pivotal movement of the staple cartridge section 315 and cartridge 316 will now be described. When collar 322 is moved proximally by hand, upper plate 402 and central centering plate 406 also move proximally therewith through common connector pin 440. This movement causes coil spring 416 to engage walls 412a and 412b of lower plate 404 until the spring is sufficiently compressed and the proximal wall of proximal leg 410 moves the distance "A" shown in FIG. 46. At this point, leg 410 engages wall 404a of lower plate 404 such that continued proximal movement of the collar 322 causes corresponding movement of lower plate 404. Prior to such engagement limited movement of upper plate has taken place as shown by dimension "A" in FIGS. 46 and 53 to begin camming ball 428 out of conical indentation 434 as shown in FIG. 53.

Figure 48:
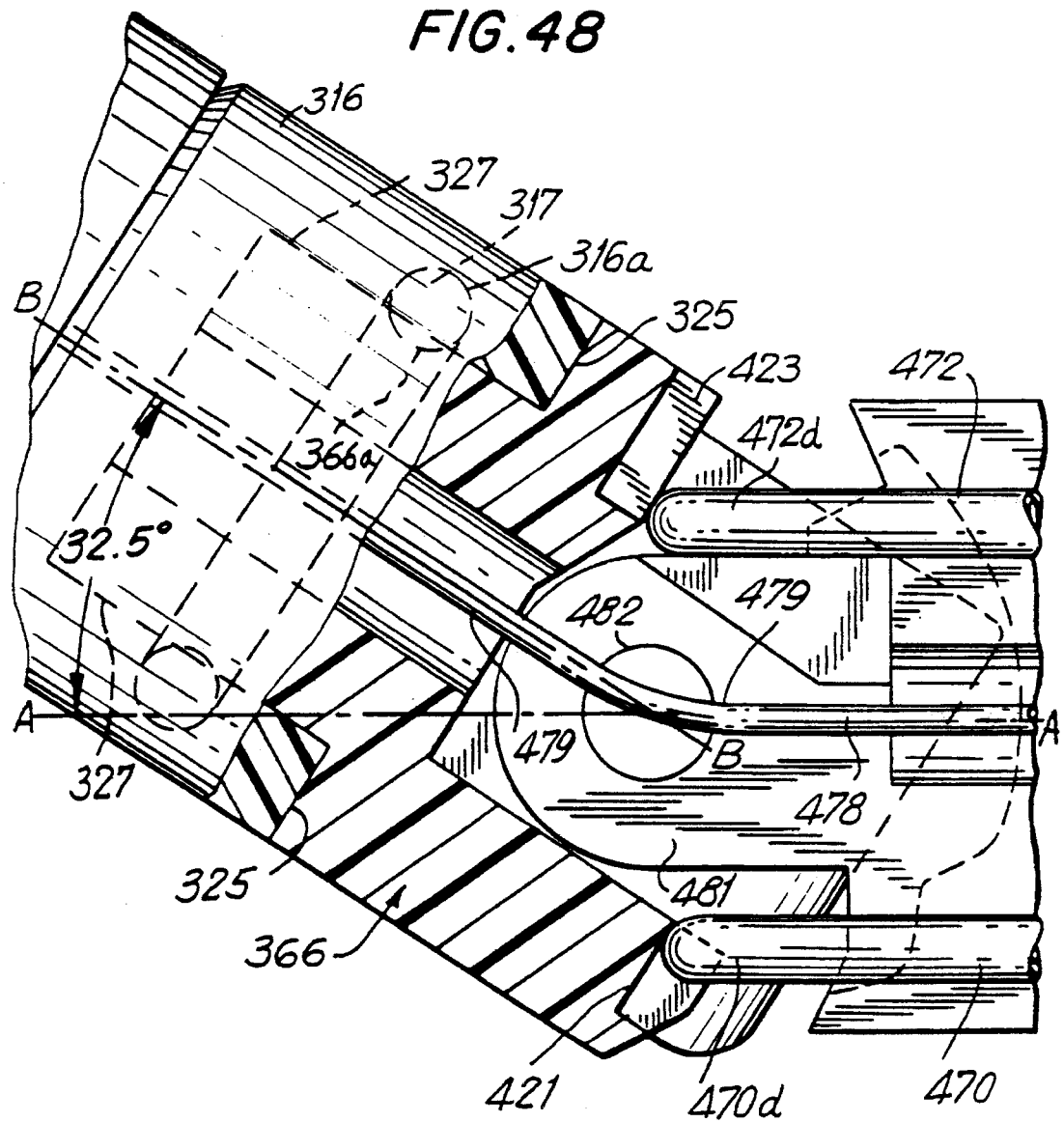
FIG. 48 is a partial cross-sectional view from the side, illustrating the relative component positions at the distal end portion of the endoscopic section with the staple storage magazine section articulated to 32.5° from the longitudinal axis of the endoscopic section.
Figure 49:
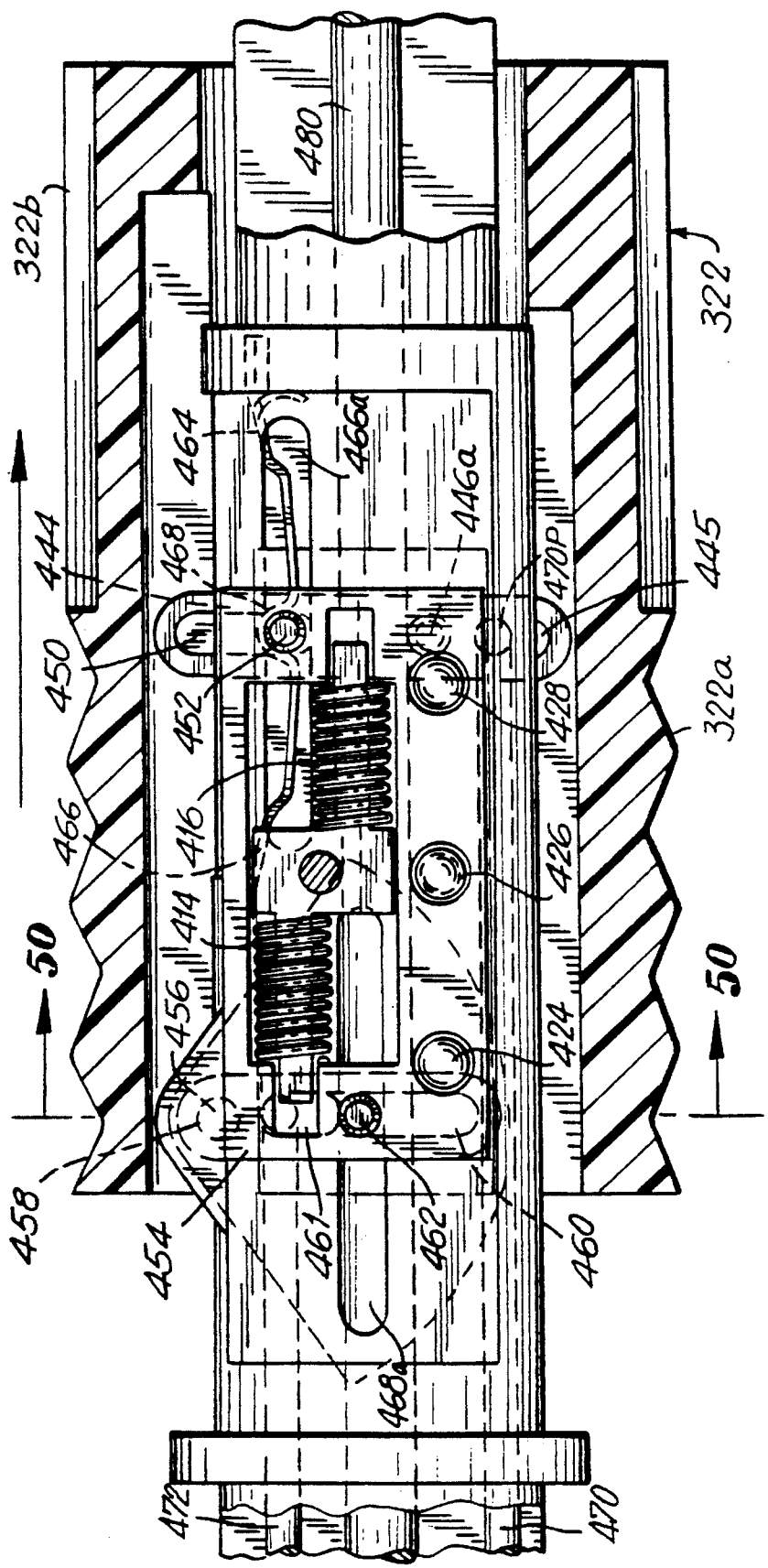
FIG. 49 is a cross-sectional view similar to FIG. 46 illustrating the slidable collar and related mechanism when the staple storage magazine section is in the 32.5° position relative to the longitudinal axis of the endoscopic section.
Figure 50:
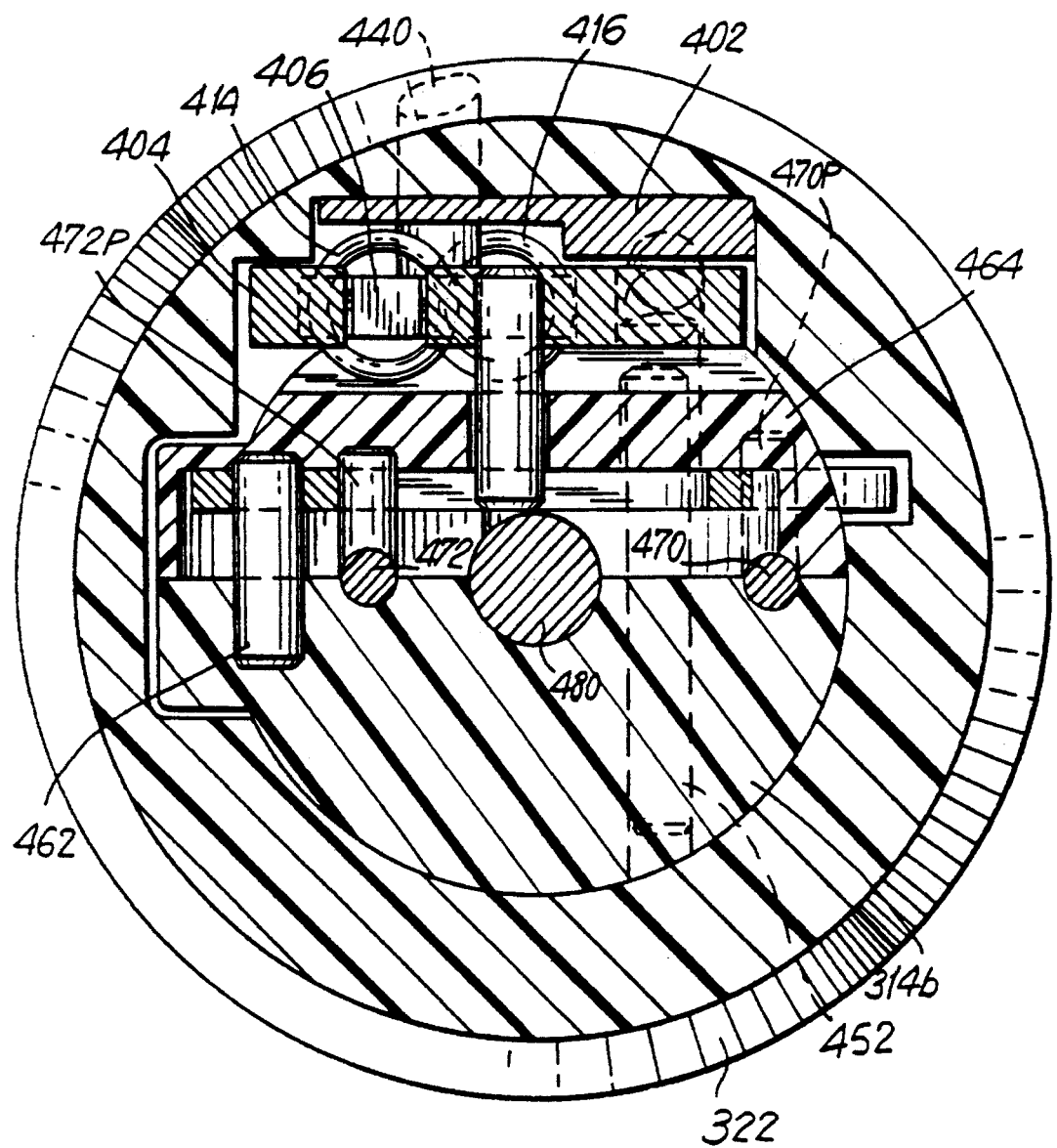
FIG. 50 is a cross-sectional view taken along lines 50—50 of FIG. 49.

The effect of such movement of ball 428 is to depress ball 428 and pin 430 against spring 432 causing upper plate 402, intermediate plate 406 and lower plate 404 to move proximally together until pin 430 engages central ball 426. This movement in turn results in proximal movement of pin 452 to the central detent 468 of spring 463 as shown in FIG. 49 such that the positions of the components are as shown in FIG. 49. In this FIG., the distal link 454 has moved counterclockwise and the proximal link 444 has moved clockwise (as viewed from above in FIG. 43). The rotational movement of proximal link 444 is due to the constraint on pin 452 to slide in slot 466 in upper housing 464a whereas pin 462 associated with proximal link 444 is constrained to move longitudinally within slot 468a in upper housing 464. Thus, the respective rotational movement of links 444 and 454 as described, in turn, result in proximal movement of the bent proximal end 472p of push rod 472 which is slidably positioned in the upper portion 461 of slot 460 in link 454 and the distal movement of bent proximal end 470p of push rod 470 which is slidably positioned in lower slot 445 of proximal link 444. The result of the pivotal rotation of the links 444 and 454 thus causes the distal ends 470d and 472d of push rods 470 and 472 to move proximally and distally, respectively, causing the cartridge 316 to pivot to the 32.5° position shown in FIG. 48. At the same time lower plate 404 has moved proximally to the position shown in FIG. 49 while central ball 426 is now positioned in engagement with conical indentation 436 via pin 430 and resilient spring 432 as shown in FIG. 54.

During the movement of the components as described to effect pivotal movement of cartridge 316, push rod 470 is slidably nestled within elongated slot 415 in the upper and lower housings 464a and 314b and push rod 472 is slidably nestled within elongated slot 417 in the upper and lower housings 464a and 314b. The lower half portions of these slots 415, 417 are seen clearly in FIG. 43 in the lower housing 314b. The respective working end portions of push rods 470, 472 engage suitably configured wall portions 421, 423 of the cartridge support member 366 as shown in FIGS. 48 and 51 to effect the desired cartridge movement.

After the pivotal movement of cartridge 316 has been completed and the cartridge position established, collar 322 may be released and this action will relieve the pressure of coil spring 416 and permit the central centering plate 406 to assume the neutral central position within aperture 412 of lower plate 404 under the natural resilient action of spring 416.

Figure 51:
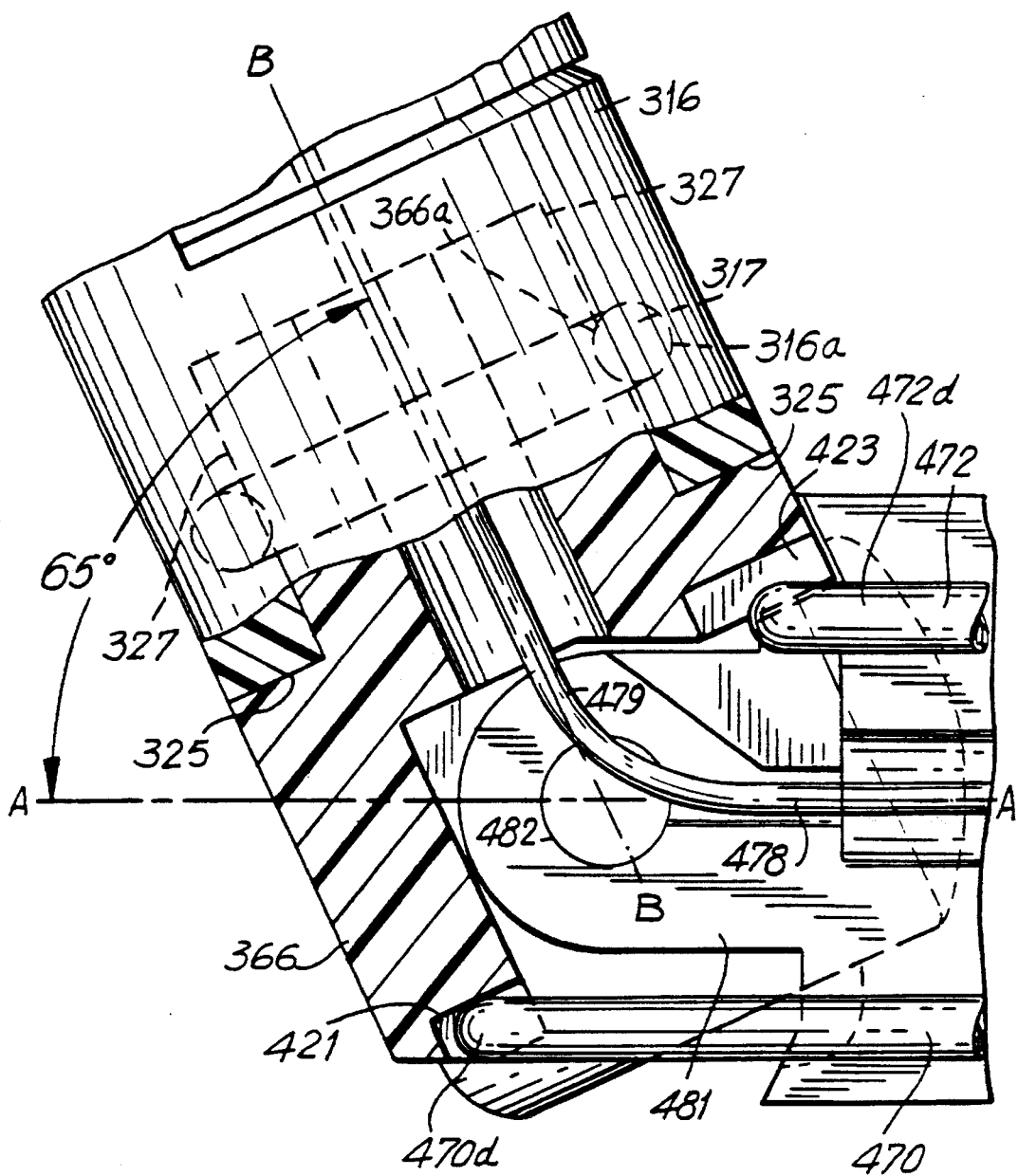
FIG. 51 is a partial cross-sectional view similar to FIG. 48 illustrating the relative component positions when the staple storage magazine section is articulated to 65° from the longitudinal axis of the endoscopic section.
Figure 52:
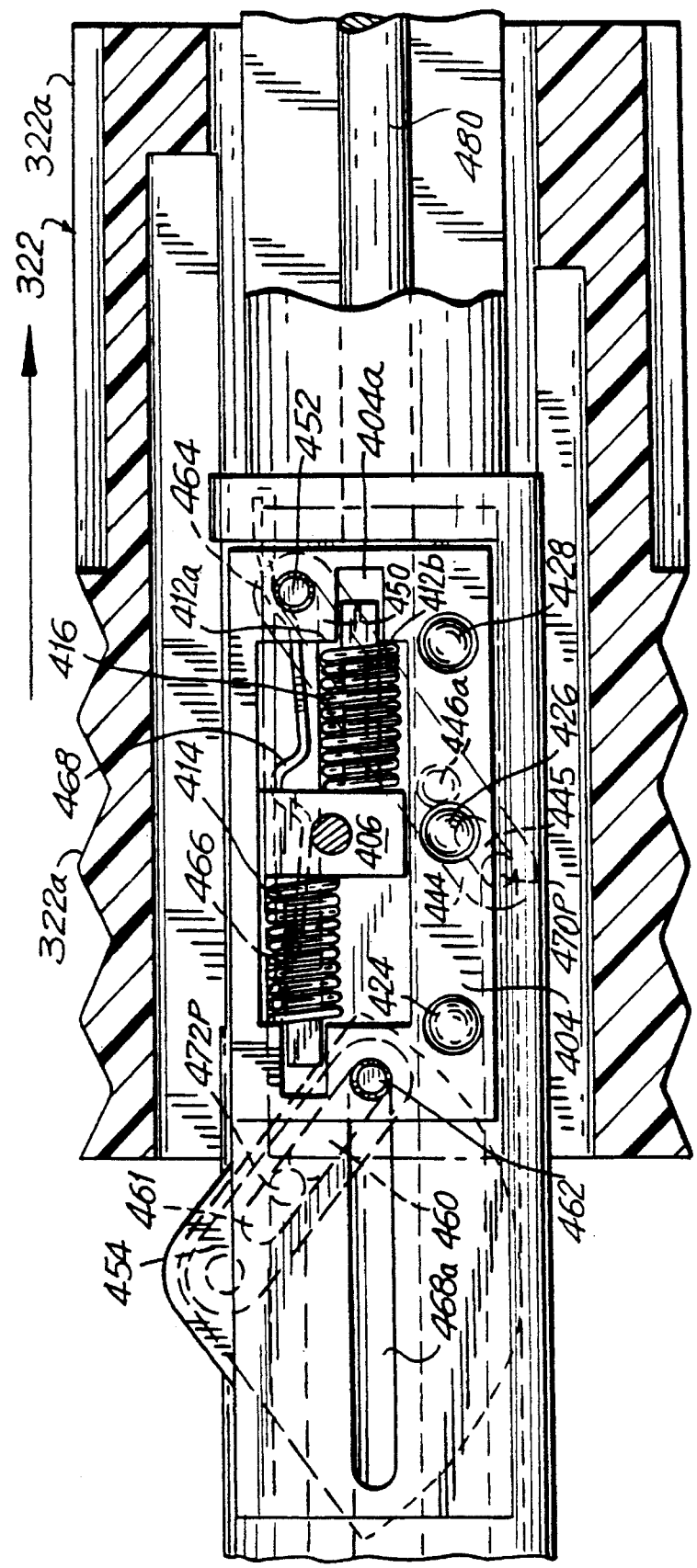
FIG. 52 is a partial cross-sectional view similar to FIG. 49 illustrating the slidable collar and related mechanism when the staple storage magazine section is articulated to 65° as shown in FIG. 51.

Referring now to the drawings and in particular to FIGS. 51, 52, and 55, the movement of the components to effect pivotal movement of the staple cartridge from the 32.5° position to the 65° position shown in FIG. 1 will now be described. This movement is produced by continued manual proximal movement of collar 322 to effect corresponding continued proximal movement of centering plate 406 and lower plate 404 in the same manner as described to effect 32.5° of movement of cartridge 316.

Until collar spring 416 once again engages shoulders 412a and 412b in the same manner described previously, continued proximal movement of collar 322 causes collar spring 416 to become compressed as described above, until the proximal tip of leg 410 of centering plate 406 engages the proximal wall portion 404a of lower plate 404 thus keying continued proximal movement of collar 322 with lower plate 404 via intermediate centering plate 406.

During the initial movement described, the camming action between central conical aperture 436 in upper plate 402 begins depressing central ball 426 against spring 432 to begin releasing the locking engagement therebetween as shown in FIG. 53, for example, such that at approximately the point when the central centering plate becomes keyed to the lower plate the ball 426 has been withdrawn from conical indentation 436 thus permitting movement of the plates 402, 406, and 404 thus keyed toward the position shown in FIG. 55. In FIG. 55, pin 432 is now positioned beneath distal ball 424 permitting the ball to be received into distal aperture 438 of upper plate 402 as shown. With this movement of the upper plate 402 and lower plate 404 in the proximal direction the pin 462 which is slidably received within the lower portion of slot 461 of link 454, and which extends through aperture 404c, causes continued clockwise rotation of distal link 454 about pivot pin 456 to the position shown in FIG. 46 causing continued proximal movement of upper push rod 472 within slot 417. Correspondingly, proximal link 444 is constrained to rotate further counterclockwise as shown in FIG. 52 causing continued distal movement of lower push rod 470 within slot 415. This movement results in further pivotal movement of the staple cartridge section to the 65° position shown in FIG. 51 in a manner similar to that described previously.

In the position of the components shown in FIGS. 51 and 52, the staple cartridge section is locked in the 65° position by the bias of spring 432 against pin 430 which locks ball 424 within distal conical aperture 438 in upper plate 402. Further locking action is obtained by the resilient force of proximal detent relief 464 of spring 463 against pin 452 slidably positioned in slot 445 of proximal link 444. When the position of the staple cartridge 316 has been achieved as shown in FIG. 51, release of collar 322 will permit central centering plate 406 to return to its central position within aperture 412 of lower plate 404, thereby relieving the stress on coil spring 416.

Once the cartridge is pivoted to either of the 32.5° or 65° angular orientations, reversal of the motion of cartridge 316 to return it toward the 0° position is simply obtained by reversal of the movements described hereinabove. In particular, collar 322 is manually returned toward its original distal position causing the movement of the components as previously described to be reversed. Ultimately when the collar is moved to the distalmost position, all internal components return to the relative positions shown in FIGS. 46 and 47 and the cartridge returns to the 0° angular position. In addition, whereas movement of the central centering plate 406 to pivot staple cartridge 316 causes compression of proximal spring 416, such opposite movements will cause similar compression of distal spring 414 as part of the reverse motions to return the cartridge to the 0° position.

Referring now to FIGS. 48, 51, and 56–61, the system for rotating the cartridge 316 about an axis extending longitudinally thereof is illustrated. According to this feature, the cartridge 316 and the cartridge support member 366 are capable of rotation about their own central axis B—B as shown in FIGS. 57 and 61. In these views, it is clear that the central axis B—B of cartridge 316 is oriented at an angle of about 32.5°, and about 65°, respectively, with respect to the central axis A—A of the endoscopic section 314.

Referring initially to FIGS. 48 and 51, the cartridge section 315 is formed of cartridge support member 366 and cartridge 316 supported thereon by internal annular snap ring 317 shown in dotted lines in those FIGS. The snap ring 317 is a resilient spring which is positioned within an annular groove 366a formed in cartridge support member 366 and which is also received by annular groove 316a formed in cartridge 316. Thus, the entire cartridge 316 is capable of rotation about its own central axis B—B independent of the endoscopic section 314 and the longitudinal axis A—A of that section. In particular, rotation of the cartridge occurs at the annular interface 325 between cartridge support member 366 and cartridge 316 as well as about the circumferential interface 327 shown clearly in FIGS. 48 and 51. The super elastic firing wire 478 extends through aperture 479 in the central boss 481 of cartridge support member 366. In all other respects, the actual cartridge which contains endoscopic staples is removable and replaceable as described in connection with the previous embodiment and in connection with FIGS. 32–39.

As seen particularly in FIG. 43, staple advancement plate 474 is attached by upwardly bent U-shaped portion 476 which contains apertures in the distal and proximal walls thereof for reception of the elongated super elastic metal firing wire 478. The wall portions defining these apertures are swaged for permanent attachment to the super elastic firing wire 478 and this firing wire is in turn attached to staple advancement tube 480 by insertion into the central opening at the distal end and swaging the metal tubular portion inwardly for attachment to the super elastic firing wire. As described in connection with the previous embodiment, the super elastic firing wire is preferably TINEL brand metal available from Raychem Corporation, Menlo Park, California. As noted hereinabove, another example of such super elastic firing wire is NITINOL brand metal. The purpose of the super elastic firing wire 478 is identical to that of the previous embodiments, namely, i.e., to be resiliently deformed about the pivoted cartridge axis 482 as shown in FIGS. 48 when it is articulated to about 32.5° and 51 when it is articulated to about 65°. When the cartridge is oriented at either of the angles mentioned previously and caused to return to its original straight condition no hysteresis is evident therein when the cartridge is returned to the 0° position. At the same time super elastic wire 478 is also effective in transmitting rotational forces from tube 480 to staple advancing plate 474 in order to rotate cartridge 316 about its own central axis B—B as shown in FIGS. 48–51. The application of such rotational forces to staple advancing tube 480 will be described further hereinbelow.

The rotation of the cartridge is effected by the fact that the staple advancing plate 474 is snugly nestled within the cartridge structure in a manner similar to the nestling of staple advancing plate 104 shown in FIG. 15 in cartridge 116 in the first previous embodiment and staple advancing plate 204 shown in FIG. 32 in cartridge 216 in the alternative embodiment. Essentially the staple advancing plate is nestled between the housing sections of the cartridge and permitted to slide proximally and distally. This nestling arrangement causes the entire cartridge to rotate about its own axis B—B when the staple advancing tube 480 is rotated to cause staple advancing plate 474 to rotate. The rotational forces are effectively transmitted about the pivot 482 of the cartridge support member 466 independent of the angle which the cartridge 416 may have assumed. The structure for transmitting the rotational forces to staple advancing tube 480 from a proximal location to effect rotation of the cartridge 316 will now be described.

Referring to FIGS. 56–59 manually operable star wheel 484 shown in FIGS. 42 and 56 is mounted for rotation within handle 312 and includes a distal surface defining a plurality of ratchet teeth 486 extending annularly therearound for mating with identically shaped ratchet teeth 488 at the proximal surface of tube 490 which is biased in the proximal direction by coil spring 492. The star wheel 484 is connected to the proximal portion of staple advancing tube 480 which is configured to have a rectangular cross section as shown in FIGS. 56a and 59. Accordingly, star wheel 484 has a similarly shaped opening 484a with corresponding flat support sides 484b and 484c such that rotation of the star wheel 484 will cause corresponding rotation of staple advancing tube 480. Thus, rotation of cartridge 316 about its own axis B—B as shown in FIGS. 57 and 61 is effected by rotating star wheel 484 with sufficient force to overcome the restraining force of the ratchet teeth 486 and 488. This rotational motion of star wheel 484 in turn causes staple advancing tube to rotate ultimately causing cartridge 316 to rotate therewith as previously described. As shown in FIGS. 56 and 59, the proximal end of staple advancing tube 480 contains attachment head 480a which is attached to the distal tab 326a of flanged thrust bar 326 which contains reception slot 326b. This arrangement permits staple advancing tube 480 to rotate independent of the thrust bar 326 while the thrust bar is normally restrained from rotation. Thus, the system for rotating the cartridge per se which is located at the distal end of the endoscopic section is thereby completed with the rotation forces being applied from a proximal location, i.e. at the handle 312.

Referring once against to FIG. 56, the system for advancing staples by pivotally squeezing trigger 220 together with the advantageous ratcheting system describe din the previous embodiment is shown. This system is identical to the clutch mechanism as described previously and accordingly further details herein are unnecessary. However, further specific details of this system are illustrated more clearly in FIG. 59 which is a perspective view of the clutch mechanism with parts separated for convenience of illustration. Rotation of cartridge 316 about its own axis B—B is shown in FIG. 58 is thus possible.

Referring to FIG. 60 there is illustrated a cross section of an alternative system for effecting rotation of the cartridge 316 from a proximal location, i.e. at the handle 312. In particular, star wheel 584 is shown which contains a proximally extending tubular section 586 integral therewith. The inner portion of the tubular section 586 houses ratchet plate 352 which forms part of the elements of the same clutch mechanism as described hereinabove. The inner portion of cylindrical member 586 is adapted to receive pawl 358 in the same manner as was described previously. Furthermore, the operation between trigger 518 and the staple advancing system is identical in all respects to the system described previously. This embodiment permits positioning of the cartridge rotating star wheel further proximally than the previous embodiment shown in FIGS. 56–59.

Referring to FIGS. 60A and 63, the structure for effecting rotation of the staple advancing system via star wheel 584 is illustrated. In this embodiment, the star wheel 584 is positioned in a more proximal position than in the first embodiment to facilitate accessibility to the user. Star wheel 584 contains distal ratchet teeth 486 which mate with proximally positioned ratchet teeth 588 of tube 590 which is biased proximally by spring 592 similar to spring 492 in FIG. 59. Additionally, the clutch ratchet mechanism for the handle is positioned within the rotation mechanism. More specifically, in this embodiment, pawl 558 is pinned for rotation to the proximal section 559 attached to staple advancing tube 480. Pawl 558 is attached by pin 560 such that when pawl 558 is in engagement with ratchet plate 552, rotation of star wheel 584 will also cause rotation of proximal section 559 as well as staple advancing tube 480. As shown in FIGS. 60A and 63, pin 560 extends from slot 586a in cylindrical member 586, through pawl 558 and spring 561 on pins 559b and 559c, into slot 480a in staple advancing member 480 and through aperture 559a in proximal staple advancing tube 559. Thus, when pawl 480 is in engagement with ratchet plate 552 within cylindrical member 586, rotation of the star wheel 584 will cause rotation of the staple advancing system. Proximal tubular member 559 which is engageably received within slot 534a of triangular member 534 will rotate within the slot as star wheel 584 is rotated. As described hereinabove, rotation of the staple advancing system will thereby cause corresponding rotation of the staple cartridge 316 which includes the exemplary angles illustrated in FIGS. 58 and 62. Other suitable fastening techniques may be utilized. In the embodiments of FIGS. 56–62, rotation to any angle up to 360° and beyond is possible independent of the pivotal angle of the staple cartridge by simply rotating the star wheel.

ADDITIONAL ALTERNATIVE EMBODIMENTS

In the description of the alternative embodiments which follows, reference is made to FIGS. 64–81 in which, wherever possible, like components are identified by numerals similar to the numerals for like components of the previous embodiments except that they begin with the numeral "6". Accordingly, for example, whereas the entire apparatus for the previous embodiments were respectively identified by numerals "10", "210", and "310", the present embodiment illustrated in FIG. 64 is identified by numeral "610". In addition, for convenience of illustration, certain components will be identified by three digit numerals beginning with the numeral "7" and where possible, by three digit numerals beginning with the numeral "8" and "9".

Furthermore, the features described in connection with the present embodiment are contemplated to be complementary to the features and improvements described previously. Accordingly, those features described in connection with the previous embodiments which are incorporated herein need not be repeated. For example, one magazine for storing staples is preferably a removable and replaceable cartridge as shown in FIG. 33 of the previous embodiment and the description thereof is not repeated herein. However, it is also contemplated as another mode of storing and applying staples to incorporate a permanently attached magazine as shown for example in FIGS. 1 and 15. That system need not be repeated herein since reference is made to the description hereinabove.

Referring now to FIG. 64, there is illustrated a perspective view of an alternative embodiment of the apparatus constructed according to the invention. In general, the apparatus of the present embodiment is similar in most respects to the apparatus of the previous embodiments. The apparatus incorporates the following features:

1. Pivotal movement of the staple storage magazine section to 20°, 45°, and 65° respectively via a double knurled collar similar to collar 322 shown in FIGS. 42–55;
2. Dual detent mechanisms for the staple storage magazine section in either of the 0°, 20°, 45°, or the 65° positions; and
3. Various staple applying and closing features, including an improved anvil, staple pusher, and spring channel as well as a pair of distally extending members at the distalmost end of the instrument intended to stabilize the orientation of the instrument during application of staples to body tissue.

Referring again to FIG. 64, there is illustrated a perspective view of apparatus 610 constructed according to the present embodiment. The apparatus 610 includes frame portion 612, an endoscopic section 614 having a distal end portion and a generally longitudinal axis, and a staple cartridge section 615 which includes staple cartridge support member 666 on which is supported removable staple storage cartridge 616. Generally, the frame portion 612 supports the actuating components as described hereinabove in connection with the previous embodiments. Preferably, the frame portion is configured as a handle as shown, grippable by hand. Generally, it may be stated that the staple cartridge support member 666 is pivotally attached to the distal portion of the endoscopic section 614, so cartridge support member 666 may be pivoted up to about 65° with respect to the aforesaid longitudinal axis. Such resultant pivotal movement will result in similar pivotal movement of the staple storage cartridge 616 since the cartridge is directly supported thereon. The pivotal movement of the staple cartridge support member 666 and related mechanism is somewhat similar to the system described in connection with the previous embodiments with the additional features described hereinbelow.

The mechanism for pivoting the staple storage cartridge 616 between positions of about 0°, about 20°, about 40°, and about 65° with respect to the central longitudinal axis of the endoscopic section 614, such as shown in phantom lines in FIG. 65, is illustrated generally in FIGS. 67–77. In particular, the operation is described to pivot the cartridge via dual knurled collar 622. The appropriate dimensions of the links, the rods and related components have been selected to effect pivotal movements of the staple storage magazine section to about 20°, about 45° and about 65°. However, the relevant dimensions and mechanical advantages may be selected to provide other alternative angular orientations for the staple storage section.

Referring in particular to FIGS. 67–68, push rods 770, 772 extend from sliding collar 622 through seal member 715 and through endoscopic section 614 to a position substantially adjacent a proximal portion of circular flange 614d at the distal end shown in FIG. 67. Firing rod 780 extends from the staple advancement tube 659 shown in FIG. 66 through guide tube 780b to the proximal end of firing wire 602 and attached thereto as shown in FIG. 67.

Collar 622 includes dual gripping knurled surfaces similar to the collar described in connection with the previous embodiments. The distal knurled surface 622a facilitates distal and proximal movement of the collar 622 and the proximal knurled surface 622b facilitates rotational movement of the collar about the central axis of the endoscopic section, so that collar 622 is thus conveniently movable longitudinally and rotatably by the user when the collar 622 is gripped between the user's fingers. Collar 622 is fixedly connected to endoscopic section 614 via pin 740, and related components as will be described such that rotation of collar 622 causes corresponding rotation of endoscopic section 614. However, the operator need not grip the collar 622 at any specific locations.

Referring in particular to FIG. 67, collar 622 is structured and dimensioned to contain a series of plates 5 similar to the system of plates employed by the embodiments described previously, except that the present series of plates has been modified to provide four (4) position articulation to the staple cartridge section 615. The present articulation system includes an upper plate 702, a first lower plate 704a, a second lower plate 704b, and a central centering plate 706 having distally extending leg 708 and proximally extending leg 710. Both lower plates 704a, 704b include a respective cut-out 712 which is dimensioned and configured to receive intermediate centering plate 706 as shown in FIG. 68 with legs 708 and 710 respectively surrounded by coil springs 714 and 716. When the plates are assembled and positioned within opening 622c in collar 622 as shown in FIG. 68 centering springs 714 and 716 serve to maintain the centered position of intermediate centering plate 706 within the cut-outs 712 of the lower plate 704a, 704b.

Referring once again to FIG. 67 in conjunction with FIG. 68–69, both lower plates 704a, 704b contain at least four cylindrical apertures 718, 720, 722, and 723 in which are positioned locator balls 724, 726, 728, and 729. Depending upon the position of the lower plates 704a, 704b with respect to the lower housing 614b, pin 730 is biased upwardly by spring 732 to position one of the locator balls 724, 726, 728, 729 within the respective conical aperture 734, 736, 738, 739 to locate and fix the position of upper plate 702, as illustrated for an exemplary ball 729 in aperture 739 in FIG. 69.

Referring now once again to FIG. 67, pin 740 extends through an aperture in collar 622 and through aperture 744a in upper plate 702 as well as through aperture 746 in central plate 706 to key these components together for common distal and proximal movement. In FIG. 67, proximal link 744 is pivotal about pin 746a which extends through an aperture in link 744, an aperture in upper housing 614a and an aperture in lower housing 614b. The link 744 contains slot 750 for slidable reception of pin 752. Pin 752 is slidable distally and proximally within slot 766a in upper housing 614a and also extends through a first aperture in lower plates 704a, 704b. Similarly, distal link 754 is pivotal about pin 756 which extends through an aperture and contains slot 760 for slidable reception of pin 762. Pin 762 is slidable proximally and distally in slot 768a in upper housing 614a and which also extends through a second aperture in lower plates 704a, 704b.

Referring again to FIG. 68, detent spring 763 contains at least four arcuate relief sections including distal arcuate detent relief 766, proximal detent relief 764 and intermediate U-shaped detent reliefs 768, 769 for respective engaged resilient reception of proximal slidable pin 752 as shown in FIGS. 67–68. As shown in phantom lines in FIG. 68, links 744 and 754 respectively receive the bent "L-shaped" end 770p and 772p of drive rods 770 and 772 respectively, each of which are respectively arranged at their distal ends 770d and 772d to engage at least one proximal wall portion of the flange 614d attached to the cartridge support member 666 to effect pivotal movement of the cartridge section as rod 772 is moved proximally and rod 770 is moved distally to effect pivotal movement of staple cartridge section 615.

The distal ends 770d, 772d of drive rods 770, 772, respectively, may abut the flange 614d to pivot the flange 614d by the above described reciprocating longitudinal motion of the drive rods 770, 772. The distal ends 770d, 772d may be mounted into flange 614d by alternative techniques whereby they move proximally and distally in opposite directions to actuate the pivoting of the flange 614d about the pivot pin 782. Moreover, one rod may be provided as discussed in connection with the previous embodiments.

The operation of the system to effect pivotal movement of the staple cartridge section 615 will now be described. When collar 622 is in the distalmost position, the staple storage cartridge 616 is at 0° relative to the longitudinal axis of the endoscopic section 614; i.e. in line with the endoscopic section 614 as shown in solid lines in FIG. 64–65. In this position, pin 752 is engageably nestled within distal spring detent 766. The engaged nestled position of rod 752 in spring detent 766 provides a first detent to retain cartridge push rods 770 and 772 from movement thereby securing the 0° angular position of the staple storage cartridge 616. In addition as shown in FIG. 69, locator ball 729 is positioned within conically shaped indentation 739 in upper plate 702 to provide a second detent mechanism to restrain movement of push rods 770 and 772 by upper plate 702 against proximal and distal movements. Thus, the 0° position of staple storage cartridge 616 is established and fixed by a dual detent system.

Referring again to FIG. 68–69, the mechanical movements required to produce pivotal movement of the staple cartridge section 615 and staple storage cartridge 616 will now be described. When collar 622 is manually moved proximally by the user, upper plate 702 and central centering plate 706 also move proximally therewith through common connector pin 740. This movement causes coil spring 716 to engage the proximal walls of aperture 712 of lower plates 704a, 704b until the coil spring 716 is sufficiently compressed and the proximal wall of proximal leg 710 moves the distance "A" shown in FIG. 68. At this point, leg 710 engages the proximal walls of aperture 712 of both lower plates 704a, 704b such that continued proximal movement of the collar 622 causes corresponding movement of lower plates 704a, 704b. Prior to such engagement limited movement of upper plate 702 has taken place to begin camming ball 729 out of conical indentation 739 in a manner essentially identical to the camming illustrated in FIG. 53 for the previous embodiment.

The effect of such movement of ball 729 is to depress ball 729 and pin 730 against spring 732 causing upper plate 702, intermediate plate 706 and lower plates 704a, 704b to move proximally together until proximal movement of pin 752 to the next proximal detent 768 of spring 763 is achieved so that pin 730 engages intermediate ball 728. The positions of the components are as illustrated in FIG. 68, i.e. the distal link 754 has moved counterclockwise and the proximal link 748 has moved clockwise. The rotational movement of proximal link 748 is due to the constraint on pin 752 to slide in slot 766a in upper housing 614a whereas pin 762 associated with proximal link 754 is constrained to move longitudinally within a slot 768a in upper housing 614a.

Thus, the respective rotational movement of links 748 and 754 as described, in turn, result in proximal movement of the bent proximal end 772p of push rod 772 which is slidably positioned in the upper portion 761 of slot 760 in link 754 and the distal movement of bent proximal end 770p of push rod 770 which is slidably positioned in lower slot 745 of proximal link 744. The result of the pivotal rotation of the links 748 and 754 thus causes the distal ends 770d and 772d of push rods 770 and 772 to move proximally and distally, respectively, causing the flange 614d connected to the staple cartridge support member 666 to pivot about pin 782 to the 20° position shown in FIG. 65. At the same time lower plates 704a, 704b have moved proximally while intermediate ball 728 is now positioned in engagement with conical indentation 738 via pin 730.

After the pivotal movement of staple storage cartridge 616 has been completed and the cartridge position established, collar 622 may be released and this action will relieve the pressure of coil spring 716 and permit the central centering plate 706 to assume the neutral central position within aperture 712 of lower plates 704a, 704b under the natural resilient action of spring 716.

Referring once again to the drawings and in particular to FIGS. 51, 52, and 55 of the previous embodiment, the movement of the components of the present alternative embodiment to effect pivotal movement of the staple cartridge from the 20° position to the 45° position and to the 65° position shown in FIG. 65 is as described for the movement of similar components of the previous embodiment described above. This movement is produced by continued manual proximal movement of collar 622 to effect corresponding continued proximal movement of centering plate 706 and lower plates 704a, 704b in the same manner as described to effect 45° of movement and 65° of movement of cartridge 616.

Until collar spring 716 once again engages proximal walls of aperture 712 in the same manner described previously, continued proximal movement of collar 622 causes collar spring 716 to become compressed as described above, until the proximal tip of leg 710 of centering plate 706 engages the proximal wall portions of lower plates 704a, 704b thus keying continued proximal movement of collar 622 with lower plates 704a, 704b via intermediate centering plate 706.

During the initial movement described, the camming action between conical aperture 736, 734 in upper plate 702 begins depressing intermediate balls 726, 724 against spring 732 to begin releasing the locking engagement therebetween in an identical manner as shown in FIG. 53 in the previous embodiment, for example, such that at approximately the point when the central centering plate becomes keyed to the lower plates 704a, 704b, the balls 726, 724 have been withdrawn from conical indentation 736, 734, respectively, thus permitting movement of the plates 702, 706, 704a, and 704b thus keyed to cause continued clockwise rotation of distal link 754 about pivot pin 754 and to cause continued proximal movement of upper push rod 772. Correspondingly, proximal link 744 is constrained to rotate further counterclockwise causing continued distal movement of lower push rod 770. This movement results in further pivotal movement of the staple cartridge section 616 to the 45° position and the 65° position, respectively, shown in FIG. 65 in a manner similar to that described previously.

Upon positioning the components to pivot the staple cartridge section 615, the staple cartridge section 615 is moved to the 0°, 20°, 45°, and 65° positions by the bias of spring 732 against pin 730 which locks the upper plate 702 by detent action of balls 729, 728, 726, 724 respectively within conical apertures 739, 738, 736, and 734 in upper plate 702 to provide a tactile signal to the user of the position of the staple cartridge section 616. Further detent action is obtained by the resilient force of the respective detent reliefs 769, 768, 766, 764 of spring 763 against pin 752 slidably positioned in slot 745 of proximal link 744. When any of the positions of the staple storage cartridge 616 has been achieved as shown in FIG. 65, release of collar 622 will permit central centering plate 706 to return to its central position within aperture 712 of lower plates 704a, 704b, thereby relieving the stress on coil spring 716.

Once the staple storage cartridge 616 is pivoted to either of the 20°, 45°, or 65° angular orientations, reversal of the motion of staple storage cartridge 616 to return it toward the 0° position is simply obtained by reversal of the movements described hereinabove. In particular, collar 622 is manually returned toward its original distal position causing the movement of the components as previously described to be reversed. Ultimately when the collar 622 is moved to the distalmost position, all internal components return to the relative positions shown in FIGS. 68–69 and the cartridge returns to the 0° angular position as illustrated in FIGS. 64–65. In addition, whereas movement of the central centering plate 706 to pivot staple storage cartridge 616 causes compression of proximal spring 716, such opposite movements will cause similar compression of distal spring 714 as part of the reverse motions to return the staple storage cartridge 616 to the 0° position.

Referring now to FIGS. 67 and 70, the system for rotating the staple storage cartridge 616 about an axis extending longitudinally thereof is illustrated. According to this feature, the staple storage cartridge 616 and the staple cartridge support member 666 are capable of rotation about their own central axis. The staple cartridge section 615 is formed of staple cartridge support member 666 and staple storage cartridge 616 supported thereon by internal annular flange 614d shown in dotted lines in those FIGS. The flange 614d is a cylindrical section positioned at the distal end of the endoscopic section 614. An annular groove 666a formed in flange 614d is received by pins 789l, 789r mounted in apertures 666c (not shown) and 666d at the proximal end of the entire staple cartridge support member 666 of staple cartridge section 615. Thus, the staple cartridge section 615 is capable of rotation about its own central axis independent of the endoscopic section 614 and the longitudinal axis of that section while pins 789l and 789r slide against groove 666a and retain staple cartridge support member 666 on flange 614d. In particular, rotation of the staple storage cartridge 616 occurs at the annular interface between staple cartridge support member 666 and flange 614d.

The super elastic firing wire 602 extends through aperture 779 in the proximal end of staple cartridge support member 666 and causes rotation of the staple cartridge section 615 about its own axis. It will be appreciated that when staple cartridge 24 is articulated to one of the selected angles relative to the longitudinal axis and rotated about its own axis, resilient flexing of the firing wire 602 will take place in alternating bending modes at the bend of the firing wire 602. In all other respects, the actual staple storage cartridge 616 which contains endoscopic staples is removable and replaceable as described in connection with the previous embodiment and in connection with FIGS. 32–39.

As seen particularly in FIG. 73, pusher plate or staple advancement plate 604 is attached by upwardly bent U-shaped portion 776 which contains apertures in the distal and proximal walls thereof for reception of the distal tip 778 of the elongated super elastic metal firing wire 602. The wall portions defining these apertures are swaged for permanent attachment to the super elastic firing wire 602 and this firing wire 602 is in turn attached to firing rod 780 by insertion into the central opening at the distal end and swaging the metal tubular portion inwardly for attachment to the super elastic firing wire. As described in connection with the previous embodiment, the super elastic firing wire 602 is preferably TINEL brand metal available from Raychem Corporation, Menlo Park, Calif. As noted hereinabove, another example of such super elastic firing wire 602 is NITINOL brand metal. Other suitable materials may also be used.

The super elastic firing wire 602 is identical to that of the previous embodiments, namely, i.e., to be resiliently deformed about the pivoted cartridge axis when it is articulated to about 20°, about 45°, or about 65°. When the staple cartridge section 615 is oriented at any of the angles mentioned previously and caused to return to its original straight condition, no hysteresis is evident therein when the cartridge is returned to the 0° position. At the same time super elastic wire 602 is also effective in transmitting rotational forces from tube 780a to staple advancing plate 604 in order to rotate cartridge 616 about its own central axis. The application of such rotational forces to staple advancing tube 780a will be described further hereinbelow.

The rotation of the staple cartridge section 615 about its own axis is effected by the fact that the staple advancement plate 604 is snugly nestled within the cartridge structure in a manner similar to the nestling of staple advancing plate 104 shown in FIG. 15 in staple storage cartridge 116 in the first previous embodiment and staple advancing plate 204 shown in FIG. 32 in staple storage cartridge 216 in the previous alternative embodiment. Essentially the staple advancing plate 604 is nestled between the housing sections of the cartridge and permitted to slide proximally and distally. This nestling arrangement causes the entire cartridge to rotate about its own axis when the firing rod 780 is rotated to cause staple advancing plate 604 to rotate. The rotational forces are effectively transmitted about the pivot 782 of the staple cartridge support member 666 independent of the angle which the staple cartridge section 615 may have assumed.

Referring generally to FIG. 64, the handle 612 of instrument 610 includes manual grip 618 and pivotal trigger 620 which is pivoted toward and away from manual grip 618. Trigger 620 is pivoted toward manual grip 618 during the staple advancing and firing sequence which are described in further detail below. Trigger 620 pivots away from manual grip 618 to return the instrument to the pre-fired condition in position for firing the staple next in line.

Referring again to FIG. 64, a first proximalmost manually operative star wheel 684 is rotatable and adapted to rotate the entire staple cartridge support member 666 a full 360 degrees as described hereinbelow, while proximal movement of a collar 622 including a second manually operative star wheel 634 produces pivotal motion of the staple cartridge support member 666 to one of the positions shown in phantom lines in FIG. 65. Rotation of collar 622 about the longitudinal axis of the endoscopic section 614 causes corresponding rotation of the endoscopic section 614. Further, first star wheel 684 is conveniently positioned within handle frame 618 which includes relief 618a to permit access to the star wheel by a user's fingers.

To achieve other cartridge orientations while in a pivotal position, the collar 622 may be simply rotated 180 degrees in either direction (or alternatively a full 360°) to cause corresponding rotation of the endoscopic section 614. Thus when staple cartridge 24 is articulated to one of the selected angles and collar 622 is rotated about the longitudinal axis, the staple cartridge 24 undergoes a sweeping action traversing a hypothetical conical section. Thus, it can be seen that the combination of full rotation of the tubular section 614 and the pivotal movement of the staple cartridge support member 666 facilitates a wide range of articulation of the distal end of the staple cartridge support member 666, thus facilitating application of staples over a wide range of locations (±180 degrees) and in any of a plurality of orientations. In the embodiment of the invention shown in the accompanying FIGS. incorporated herein, when the collar 622 is moved to its proximalmost position, the staple cartridge support member 666 is in one of the positions shown in phantom lines in FIG. 65; e.g. at an angle of approximately 65° with respect to the longitudinal axis of the instrument 610. When the collar 622 is advanced to the distalmost position, the staple cartridge support member 666 assumes the position shown in FIG. 64, i.e. in alignment with the longitudinal axis of the instrument 610.

Thus, in the preferred embodiment of FIG. 64, it can be seen that a full 130 degrees of pivotal movement of the staple cartridge support member 666 may be achieved simply by longitudinal movement of collar 622 in combination with full rotation of the staple cartridge support member 666 by first star wheel 684. The longitudinal movement of collar 622 causes pivotal movement of the staple cartridge support member 666 to about 65 degrees in one direction and rotation of the staple cartridge support member 666 provides effective completion of the articulation of the staple cartridge support member 666. Both of these movements in combination facilitate a wide range of maneuverability of the distal end of the staple cartridge support member 666, thus facilitating application of staples over a wide range of locations (±180 degrees) and in any of a plurality of orientations. The instrument can also be configured and the relevant components dimensioned to articulate, i.e. pivot, staple cartridge support member 616 to positions other than a 65 degree angle with respect to the longitudinal axis of the instrument which extends through handle portion 612 and centrally of the endoscopic section 614.

THE HANDLE SECTION

Referring to FIG. 66, there is shown a perspective view, with parts separated for illustration purposes, of the handle 612 of the instrument with associated components. The handle 612 is comprised of an outer housing preferably formed of separate sections as shown of polycarbonate material. The separate parts shown are attached by welding, adhesives, etc. The ultimate purpose of the handle mechanism is to provide controlled distal movement to the proximal staple advancing tube 659 of the pusher assembly, a portion of which is shown in FIG. 66. Trigger 620 is pivotally mounted to housing 618 by pivot pin 632. Pin 637 is attached to the proximal end of trigger 620 and slidably engages a proximal camming surface 636a of a triangular shaped portion of pivoting member 634 which pivots at a lower end of the handle 612 about pin 662.

As illustrated in FIG. 67, firing rod 780 is connected to proximal staple advancing tube 659 and extends through the tubular section 614, a portion of which is shown in phantom lines in FIG. 66. The proximal staple advancing tube 659 is rotatably engageably received within the upper aperture 639 of pivoting member 634 and rotates within the upper aperture 639 as first star wheel 684 is rotated. In the embodiment shown, the first star wheel 684 is intended to be permanently and rotatably attached to the instrument 610 via sleeve 714a having rim 715a slidably positioned within appropriately configured relief compartments in the handle 618 shown generally as 618b. The firing rod 780 shown in FIG. 67 extends through the sleeve 714a and spring 692 and extends through tube 690. Tube 690 is proximally biased against first star wheel 684 by spring 692. Tube 690 includes proximal tabs or rachet teeth for engaging corresponding distal tabs or rachet teeth of first star wheel 684 for rotation. The first star wheel 684 protrudes through apertures 685 on either side of handle 612. Rotation of the first star wheel 684 thus causes the corresponding rotation of the firing rod 780 ultimately to rotate and the staple cartridge section 615 about its own axis (i.e. an axis extending centrally therethrough as will be described in detail hereinbelow. As noted previously, rotation of collar 622 causes rotation of endoscopic section 614.

A clutch ratchet mechanism for the handle 612 is positioned within the rotation mechanism. More specifically, in this embodiment, pawl 658 is attached by pin 660 for rotation to the proximal staple advancing tube 659 attached to firing rod 780 shown in FIG. 67 extending through first star wheel 684 and tube 690. Thus, when pawl 658 is in engagement with ratchet plate 652 positioned within the tubular section of the first star wheel 684, rotation of first star wheel 684 also causes rotation of proximal staple advancing tube 659 as well as firing rod 780. Pin 660 extends from a distally located aperture on the tubular section of the first star wheel 684, through spring 661 and pawl 658 on pins extending from the distal end of the proximal staple advancing tube 659, as shown in FIG. 66. Pin 660 then extends into aperture 780a in firing rod 780, as shown in FIG. 67, and through an aperture in the proximal staple advancing tube 659. Thus, when pawl 658 is in engagement with ratchet plate 652 positioned within the cylindrical section of the first star wheel 684, rotation of the first star wheel 684 causes rotation of the staple advancing system.

As described hereinabove, rotation of the staple advancing system thereby causes corresponding rotation of the staple cartridge support member 666 and cartridge 24 about their own axis. In the embodiments of FIGS. 64–65, sweeping rotation to any angle up to 360° and beyond is possible independent of the pivotal angle of the staple cartridge support member 666 by simply rotating the first star wheel 684, whereas rotation of collar 622 rotates only the endoscopic section 614. If endoscopic section 614 is rotated by collar 622 and first proximalmost star wheel 684 remains fixed, the staple cartridge section 615 will not rotate, but will remain fixed with pusher plate 604 while flange 614*d* rotates.

The instrument shown is contemplated to be entirely disposable. It is also contemplated and within the scope of the invention to construct the tubular section 614 to be selectively detachable whereby the handle 612 may be sterilized and reused, or the tubular section 614 can be sterilized, and the staple cartridge support member 666 reloaded with staples for re-use. Alternatively a replacement staple cartridge 616, and optionally a replacement tubular section 614, may be detachably secured to a disposable handle 612 for multiple use during a single surgical procedure. Thus, any combination of alternatives may be incorporated within the scope of the invention.

Referring again to FIG. 66, trigger 620 is pivotally attached by a pivot pin 632 for pivotal movement toward and away from the handle grip 618, and is adapted to produce rotational movement of pivoting member 634. Thus, it can be seen that when handle grip 618 is positioned in the palm of the user's hand and trigger 620 is squeezed toward the handle grip 618, pivoting member 634 rotates in a counter-clockwise direction while the upper portion of the pivoting member 634 pivots forwardly about a point of rotation defined by a pivot pin located at the lowermost end of the handle grip 618 shown in FIG. 66.

As can be seen in FIG. 66, the pusher assembly is connected to the upper portion of the pivoting member 634 through an aperture 639 such that inward squeezing of trigger 620 causes the entire pusher assembly to advance distally against the constant force provided by negator spring 640 as shown. The negator spring 640 is formed of a resilient flat spring material coiled about a rotational bar 642 which is rotationally mounted about a cross member of bracket 646. The free end of negator spring 640 is attached to an anchor pin 648 attached to handle grip 618 via an aperture as shown, while the negator spring 640 is normally biased toward the coiled configuration as shown in FIG. 66. It can therefore be appreciated that, after squeezing trigger 620 in a full stroke from the position shown in FIG. 66 toward handle grip 618, a release of the trigger 620 permits the negator spring 640 to assume control and to return rotational bar 642 to the pre-fired proximal location by the automatic winding action of the negator spring 640 to its original unloaded configuration. This motion in turn causes the entire pusher assembly to return to the proximalmost pre-fired position as shown in FIG. 64. The constant force of negator spring 640 uniquely prevents the natural tendency of the user to rotate his/her hand as springs increase in force when progressing through a full spring cycle.

Referring to FIGS. 64 and 65, trigger stop device 650 is attached to trigger 620 and is configured and dimensioned for engagement with handle grip 618 in a manner to thereby limit the proximal pivotal movement of trigger 620. Depending upon the particular limits required in the apparatus, trigger stop device 650 can be dimensioned accordingly.

The structure and function of the uni-motion clutch mechanism is the same as described in the previous embodiments. This clutch mechanism prevents proximal movement of the pusher assembly in the event the trigger mechanism is released after the squeezing motion of the trigger mechanism and the advancement of the pusher assembly has begun but before the full stroke is completed. The clutch mechanism is self-releasing when the pusher assembly reaches the distalmost position, thus permitting the entire pusher assembly to return to the pre-fired, or proximalmost condition, and the trigger mechanism to also return to the pre-fired position.

Referring once again to FIG. 66, ratchet plate 652 is fixed to the interior surface of the first star wheel 684 and therefore fixed with respect to the handle housing. The rachet plate 652 possesses a surface defined by a plurality I of right angle triangular shaped parallel ridges. Pawl 658 is rockably mounted for distal and proximal movement with proximal staple advancing tube 659 through the interior of first star wheel 684, and is biased toward ratchet plate 652 by resilient wire spring 661 as shown. The pawl 658 is preferably of stainless steel while ratchet plate 652 is made of brass or other compatible material.

While trigger mechanism 620 is squeezed toward handle grip 618 producing distal motion of the entire pusher assembly, pawl 658 engageably slides distally past the ratchet surface of ratchet plate 652 such that one corner of the tip of the pawl 658 sequentially engages each right angled ridge of ratchet plate 652 to thereby prevent proximal movement of the pusher assembly in the event the trigger mechanism is released by the operator. The engagement of pawl 658 with ratchet plate 652 provides audible confirmation that the pusher assembly is moving distally since the user hears a series of progressive audible clicks. This action continues with the tip of pawl 658 sliding past the ratchet surface of the ratchet plate 652 until the pawl 658 is positioned distally of the distalmost tooth.

After completion of the staple firing stroke and upon release of the trigger mechanism 620, the pawl 658 moves proximally with the pusher assembly as described under the action of spring 661. An end portion of pawl 658, which is now free, engages the distal end of the ratchet plate 652 causing the pawl 658 to rock to the reverse direction so as to slide proximally past the ratchet surface of ratchet plate 652 without interference to the proximal movement of the pusher assembly. Thus, it can be seen that the clutch mechanism as described effectively permits squeezing the trigger mechanism 620 toward the handle grip 618 while maintaining all positions midway through the stroke in the event the operator releases the grip, and also permitting return motion thereof after the stroke has been completed. The clutch mechanism also allows the operator to advantageously preposition a staple such that the legs of the staple protrude from the distal end of the staple cartridge section discussed hereinafter, and then to release pressure from the trigger mechanism. The operator may then turn full attention to locating the prepositioned staple in the desired target location, at which point the pivoting of the trigger mechanism may be resumed and the cycle completed. This staple prepositioning greatly facilitates staple placement.

THE TUBULAR SECTION

For purposes of the present description, the tubular section 614 and related components contained therein is described as the elongated section shown in FIG. 67 extending from the handle 612 to flange 614*d* pivotally attached thereto at the distal end and having the staple cartridge section 615 extending distally from the flange 614d. However, it is clear that reference to the tubular section 614 may contemplate the section shown, with or without the staple storage cartridge 616 or staple cartridge support member 666 included.

Referring now to FIG. 67 in conjunction with FIGS. 64–66, a pusher assembly is positioned within and extending through the tubular section 614 and includes proximal staple advancing tube 659 connected to firing rod 780 extending through the tubular section 614 to the distal end. In FIG. 67, the tubular section 614 is shown in a perspective view with parts separated for convenience of illustration and includes first housing half section 614a and second housing half section 614b. The housing half sections 614a, 614b are preferably of a polycarbonate material such as LEXAN brand material mentioned previously, and are attached by welding, adhesives, etc. Positioned within the housing half sections 614a, 614b is the pusher assembly as described in more detail below.

Collar 622 is rigidly connected to the elongated endoscopic section 614 via pin 740 and plates 602, 604a, 604b, and 606 as described above. Accordingly, manual rotation of collar 622 causes corresponding rotation of elongated endoscopic section 614.

THE STAPLE FIRING SYSTEM

Referring now to FIGS. 70 and 73 in conjunction with FIG. 67, the pusher assembly includes firing rod 780 connected to flexible elongated firing wire 602 extending through aperture 779 and which is in turn connected to pusher plate 604 as shown. The connection between firing rod 780 and firing wire 602 is a crimped or swaged connection, whereas the connection between firing wire 602 and pusher plate 604 is accomplished by an interference fit between the firing wire tip 678 and bent portion 676 which is attached to pusher plate 604 as illustrated in FIG. 73. In an embodiment described hereinbelow, swaging of the bent portion 676 to firing rod 780 is utilized. Firing rod 780 and pusher plate 780 are preferably made of stainless steel whereas firing wire 602 is made to be resiliently flexible to accommodate the pivotal movement of the staple cartridge support member 666 and collar 614a since firing wire 602 is located at the distal end of the instrument 610.

As seen particularly in FIG. 73, pusher plate 604 is attached by upwardly bent U-shaped fastener 676 which contains apertures in the distal and proximal walls thereof for reception of the distal tip 678 of the elongated super elastic metal firing wire 602. The wall portions defining these apertures are swaged for permanent attachment to the super elastic firing wire 602 which is in turn attached to firing rod 780 by insertion into a central opening at the distal end and swaging the metal tubular portion inwardly for attachment to the super elastic firing wire 602. As noted previously, the super elastic firing wire 602 such as TINEL brand, NITINOL brand, as well as other suitable materials may be used.

THE STAPLE CARTRIDGE SUPPORT SECTION

Referring now to FIGS. 70–74, the staple cartridge support section 618 is illustrated at the distal end of the instrument 610. In FIG. 73 the staple cartridge support member 666 is shown in the position generally in alignment with the tubular section 614. As illustrated in FIG. 73 in conjunction with FIG. 70, the staple cartridge section 615 is formed of an outer housing of a suitable plastic material such as polycarbonate and is comprised of upper housing half section 865, a lower housing half section 866, and a cartridge support plate 817 attached by ultrasonic welding, adhesives, etc. The assembled staple cartridge section 615 is attached to and integral with staple cartridge support member 666. The flange 614d includes at least one indentation 781 at the proximal end adapted to respectively engageably receive the rounded distal ends 770d, 772d of drive rods 770, 772 respectively, such that when the drive rods 770, 772 are respectively and alternatively moved in the proximal and distal directions as described hereinabove, one rod may advance distally to cause the staple cartridge support member 666 to rotate and the other rod withdraws to permit the pivotal motion of the lower housing 866 of the staple cartridge support member 666.

The staple cartridge support member 666 is adapted to removably support a readily detachable staple storage cartridge 616 containing a plurality of surgical staples 809 which are fed individually to the staple cartridge section 615 and which are particularly shaped to penetrate and to attach surgical mesh to body tissue. For particular details of the shape of the staples 809 constructed according to the invention, reference should be made to FIGS. 75–79.

In FIG. 70, lower housing half 866 includes stabilizing tabs 822l, 822r projecting distally from the distal end. During positioning of the staple cartridge section 615 against body tissue or a mesh preparatory for staple insertion thereof, the stabilizing tabs 822l, 822r brace the staple cartridge section 615 against firm or taut tissue, bone, or prosthetics underlying the body tissue/mesh targeted for staple insertion due to the application of concentrated pressure thereto by these tabs. For example, during hernia repair, the stapling of a mesh to the Ligament of Cooper requires stable positioning of the distal end of the apparatus despite the curved surface of the underlying pelvic bone. The stabilizing tabs 822l, 822r press against the mesh and underlying body tissue and/or bone forming temporary indentations to prevent the distal end from sliding as the lowermost staple 810 is advanced, inserted, and formed into the targeted body tissue/mesh. Tabs 822l, 822r also function as spacers so the staple is formed without contacting the Cooper's Ligament.

The present invention utilizes a system of storage of the staples 809 similar to the system disclosed in copending commonly assigned parent application Ser. No. 07/950,425, filed Sep. 23, 1992, the contents of which are incorporated by reference herein. The staples 809 are positioned in adjacent stacked relation to form an angle with the longitudinal axis of the instrument of approximately 45 degrees as shown in FIG. 70. One purpose of stacking the staples as shown is to provide greater visibility to the user by the fact that the outer surface of the staple storage cartridge 616 adjacent the stack of staples 809 forms a similar angle and provides visibility to the user at the distal end of the instrument 610. Angular stacking of the staples 809 as shown facilitates storage of a plurality of staples in a structure configured and dimensioned for use in stapling applications, e.g. for use through a trocar guide tube of diameter of about 62 mm for example. The stack of staples 809 as shown in FIG. 70 is positioned and retained in such position by a resilient spring member 813 having dual resilient legs and whose side profile is curved as shown in FIG. 73. In an alternative preferred embodiment, the staples are stacked substantially vertically rather than at an angle. This also facilitates visibility and storage.

The distal end of each leg engages the uppermost staple follower 814 in the form of a nylon insert having a general "H-shaped" configuration and dimensioned sufficient to cover the staples as best shown in FIG. 70. The nylon follower 814 is intended to transmit the downward force of the staple retainer spring 813 so as to distribute the force on the stack of staples 809 in a manner to facilitate a constant and uni-directional downward force on the lowermost staple which is positioned for advancement and deformation. It also functions to advance the stack of staples downwardly when the lowermost staple is fired. Anvil 820 is shown in FIG. 70 and includes upwardly extending legs 816, 818 which act as individual anvils at the distal end as shown in FIG. 70 for forming the staple therearound.

Thus, as seen in FIG. 70, the lowermost staple 810 is in a position for engagement by pusher plate 604 when the pusher assembly is advanced distally. The distal end of pusher plate 604 is shown clearly in FIGS. 75–77 and includes distally advancing lands 604r, 604l at the distal end to facilitate transmission of advancing force to the two rounded or arcuate bridge portions of the staple 810. This relative complementary configuration of the pusher plate 604 and the lowermost staple 810 facilitates efficient and uniform distribution of force to the staple when it is deformed about the anvil members as described below.

As illustrated in greater detail in FIGS. 75–77, the distal end of pusher plate 604 includes projections 604a, 604b forming a gap 604c therebetween. Projections 604a, 604b press against central bight portion 810c of staple 810 to counter the tendency of the central bight portion 810c to bend as the staple 810 is bent as shown in FIGS. 75–77. Thus, the central bight portion 810c is maintained in a substantially straight shape throughout forming of the staple 810.

The central gap 604c of pusher plate 604 serves to allow the central resilient member 824c of spring channel member 824 to spring upward in a position proximal to the central bight portion 810c, as described further below. Additionally, since the pusher plate 604 and staple 810 slide over the surface of anvil 820 to form the staple 810, as shown in FIGS. 75–77, the gap 604c of pusher plate 604 serves as a relief, allowing smooth distal and proximal motion of pusher plate 604 and staple 810 over anvil 820 without detracting from the structure of the pusher plate 604.

As shown in FIG. 70, a spring channel member 824 is positioned between the anvil 820 and the lower housing half 866. A proximally directed tab 819 extends from the distal end of anvil 820 having an aperture formed thereabove for receiving the central resilient member 824c of the spring channel member 824. The spring channel member 824 is positioned in a cavity 882 molded into lower housing half 866 at the distal end, and the tab 819 of anvil 820 extends into a locating aperture 881 at the distal end of the lower housing half 866 for locating and positioning the anvil 820 substantially adjacent the lower housing half 866.

As illustrated in FIG. 71, the anvil 820 has upwardly extending legs 816, 818 and tab 819 extending downwardly from the distal end of the anvil 820. Proximal projections 876 (only one shown in FIG. 71, the second being rearwardly thereof) extend downwardly for locating and positioning the anvil 820 adjacent the lower housing half 866 by extending into apertures 852l, 852r at the proximal end of lower housing half 866 shown in FIG. 70. In conjunction with aperture 853 of anvil 820 for positioning projection 290 of the lower housing half 866, the projections 876 and tab 819 of anvil 820 cooperate with corresponding apertures 852l, 852r and aperture 881 to properly position anvil 820 between upper housing half 865 and lower housing half 866.

Referring to FIG. 71, anvil 820 also comprises projections 872, 874 extending downward from the anvil 820 to engage corresponding apertures 892, 894 of the spring channel member 824 as shown in FIG. 72. The anvil 820, including projections 872, 874, and the spring channel member 824 are made of stainless steel, so the apertures 892, 894 may also serve to position the anvil 820 substantially adjacent the spring channel member 824 for attachment thereof, such as by spot welding.

It will be appreciated that the staples 810 have a minute thickness and are pushed through a narrow channel of the distal end of the apparatus by pusher plate 604. The manufacturing of the spring channel member 824 from stainless steel with substantial precision provides a uniform channel for staple passage. The channel and pusher plate 604 allow for smooth operation of the instrument for inserting the staple 810 into tissue.

As illustrated in a top view in FIG. 72, the spring channel member 824 includes a proximal portion 891 having apertures 892, 894 as described above. The spring channel member 824 also comprises side portions 886, 888 connected by transverse member 896 at the distal end of spring channel member 824. Each of the side portions 886, 888 forms an elongated slot for smooth passage therethrough of a surgical staple advanced distally over the flat upper surface of the anvil 820 by pusher plate 604 towards anvil legs 816, 818.

Referring once again to FIGS. 70 and 73, during assembly, the spring channel member 824 and anvil 820 are positioned between cartridge support plate 817, upper housing half 865, and lower housing half 866. During the aforesaid positioning and attachment of the plastic components 865, 866, 817 by ultrasonic welding, adhesives, etc., the metallic spring channel member 824 and anvil 820 retain their shape so that the side portions 886, 888 of spring channel member 824 maintain a predetermined slot for smooth staple passage therethrough.

The spring channel member 824 includes central resilient member 824c and lateral resilient members 824l, 824r forming a "W" configuration at the distal end of the spring channel member 824. Anvil legs 816, 818 extend upward between central resilient member 824c and lateral resilient members 824r, 824l, respectively, so a surgical staple 810 as shown in FIG. 73, for example, is biased upward by upwardly biased resilient members 824l, 824r as the staple 810 is advanced distally towards anvil legs 816, 818. Therefore, after the pusher plate 604 is withdrawn proximally, resilient members 824l, 824r raise the formed staple 810 as shown in FIG. 77 off anvil legs 816, 818 to disengage the formed staple 810 from the apparatus 610.

As the staple 810 is advanced distally by the pusher plate 604 against anvil legs 816, 818, the central resilient member 824c slidably engages the underside of staple 810 until the central bight portion 810C clears the central resilient member 824c. The central resilient member 824c then rises to a position proximal to the central bight portion 810C, and a central gap 604C in pusher plate 604 is adapted to receive the risen central resilient member 824c of the spring channel member 824.

In the event of a release in pressure from the trigger 620 causing pusher plate 604 to move proximally away from a distally advanced staple such as the staple 810 shown in FIG. 75, the risen central resilient member 824c prevents the advanced staple 810 from moving proximally, such that an advanced or partially advanced staple remains within the channel formed by the spring channel member 824 and between the anvil legs 816, 818 and the central resilient member 824*c* until advancement and forming of the advanced staple by pusher plate 604 is resumed and completed.

As illustrated in FIG. 73, the staple cartridge section 615 and associated staple cartridge support member 666 are pivotally mounted at the distal end of tubular member 614 with the staple storage cartridge 616 removably mounted thereon. The structure of the staple cartridge section 615 and staple storage cartridge 616 are described above and shown in FIG. 70 and are similar to staple cartridge sections and staple storage cartridges described in further detail in commonly assigned U.S. patent application No. 07/950,425, filed on Sep. 23, 1992.

In particular, the staple storage cartridge 616 has a housing 616*a* with a window 616*c* for receiving the proximal end 814*c* of follower 814 to indicate that the last surgical staple has been fired. The proximal end 814*b* of follower 814 in window 816*c* is shown in phantom lines at proximal end 814*c* in FIG. 73.

As shown in FIG. 74, the distal end of the apparatus 610 along lines 74–74 of FIG. 73 has cartridge support plate 817 with legs 817*l*, 817*r* positioned above the lower housing half 866 with spring channel member 824 therebetween. Side portions 886, 888 form the channel for passage of a staple therethrough, and resilient members 824*r*, 824*l*, 824*c* are positioned as described above. Anvil legs 816, 818 and projections 604*l*, 604*r* of pusher plate 604 are positioned to engage a staple in the channel of spring channel member 824, and stabilizer tabs 822*l*, 822*r* are positioned to stabilize the instrument 610 in use.

THE STAPLE CLOSING SYSTEM

Referring now to FIGS. 75–77 there is illustrated the sequential views of the staple advancing and closing system between the pre-fired and fired condition of the staple. In particular, the staple and pusher mechanism are shown in FIG. 75 in the pre-fired condition, the staple 810 is shown in an intermediate formation condition in FIG. 76, and the staple 810 shown in FIG. 77 is in the final formed condition in which the staple 810 is embedded within the body tissue in a manner to retain the surgical mesh to the body tissue.

In FIG. 75, the staple pusher assembly is positioned proximal of the lowermost staple 810 and pusher plate 604 is correspondingly positioned proximal of the lowermost staple 810. In FIGS. 76–77, the pusher plate 604 has been partially advanced and fully advanced, respectively, in the distal direction. The lowermost staple 810 has been advanced distally of the stack of staples 809 in a manner such that the pusher plate 604 has now replaced lowermost staple 810 thereby preserving the integrity and position of the stack of staples 809. The preservation of the stack of staples 809 is provided by the fact that the thickness of the staple pusher plate 604 is either identical to or slightly less than the thickness of the staples for the pusher plate 604 to engage only one staple at a time.

Referring further to FIGS. 76–77 the pusher plate 604 has now advanced distally sufficient to cause the staple to penetrate the body tissue and/or a surgical mesh between the staple 810 and the body tissue. As shown in FIGS. 75–77, it can be seen that anvil legs 816, 818 have arcuate convex proximal surfaces 816*a*, 818*b*, respectively, on their proximal sides as shown in FIGS. 75–77, and are positioned for engagement by the correspondingly located arcuate concave distal surfaces of bridge portions 810*br* and 810*bl* of the back rib of the staple 810 such that engagement of the staple by the distally extending legs 604*r* and 604*l* of pusher plate 604, with the arcuate end corner portions of the staple as shown, causes the staple to deform in a predetermined manner as described below. In the preferred embodiment, the proximal portion of each of the anvil legs 816, 818 is rounded to insure that the bridge portions 810*br*, 810*bl* are formed by curving therearound to bend the staple leg members 810*l*, 810*r* inward as shown in FIG. 77.

In FIG. 77 the staple 810 is now shown in the deformed condition about the anvil legs 816, 818 and the straight portions of the back rib of the staple 810 are still in engagement with the anvils legs 816, 818. In FIG. 77, the staple 809 has penetrated into the body tissue and has been deformed and the staple deformation is completed in a manner to substantially retain a surgical mesh in an attached position with respect to the body tissue. The inwardly, projecting central portion or bight 810*c* of staple 810 is shown in cooperation with the staple legs as shown in FIG. 77. However, in FIG. 77 release of the staple 810 from the anvil members 816, 818 has not yet been completed.

Release of the staple from the anvil members 816, 818 is readily accomplished by the resilient members 824*l*, 824*r* acting as ejector springs of spring channel member 824. When the pusher plate 604 is in the position shown in FIGS. 76–77, the resilient members 824*l*, 824*r* of spring channel member 824 are retained in a downward position by lands 604*l*, 604*r* of the pusher plate 604. However, when the pusher plate 604 is moved in a proximal position such as shown in FIG. 75, the absence of the pusher plate 604 permits resilient members 824*l*, 824*r* to resiliently deflect upwardly to their natural configuration thereby creating a vertical separation between the anvil legs 816, 818 and the deformed staple, thus releasing the deformed staple from the anvil members. Continued proximal movement of the pusher plate 604 causes withdrawal of the pusher plate to a position entirely proximal of the stack of staples 809 as shown in FIG. 73, causing the stack of staples 809 to move downwardly due to the downward force of resilient staple retainer spring 813 to advance the lowermost staple to the firing position.

Once the staple 810 is applied to the mesh and body tissue, the distal end of staple cartridge 816 is withdrawn from the staple target area and preparation is made for application of the next staple. Thereafter, the apparatus may be repositioned to apply another staple, or even an array of staples.

It should be noted that the repair of body tissue utilizing a surgical mesh is exemplary, and that other applications of mesh and staples may be utilized in a manner to either reinforce a surgical repair or to encourage tissue growth. Such mesh materials are typically disclosed in U.S. Pat. Nos. 4,838,884, 4,665,221, 4,452,245, and 4,347,847. It is noted that the staple 810 constructed according to the invention is particularly adapted for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple of the present invention may be applied to attach other objects to body tissue as may come to the mind of those skilled in the art.

THE STAPLE

Referring now to FIGS. 75–79 in conjunction with FIG. 28 of the previous embodiment, there is illustrated the inventive staple 810 constructed according to the present alternative embodiment of the invention. The staple 810 is particularly shaped as shown, and is preferably formed of a length of wire of titanium. Stainless steel or equivalent material is also contemplated. FIG. 78 illustrates a perspective view of the staple 810. The staple 810 preferably has a rectangular cross-section as shown in FIG. 79. Typically, the wire is about 0.51 mm in width (dimension W in FIGS. 75 and 79–80) and 0.38 mm in thickness (dimension T in FIGS. 79–80). The initial width of the staple before closure (dimension A in FIGS. 75 and 79) is about 8.64 mm and the thickness dimension between the back rib and legs after closure (dimension B in FIG. 77) is about 2.5 mm. The staple 810 has a central bight portion 810c and wire leg members 810l, 810r extending generally perpendicular to the central portion as shown. Each leg member 810r, 810l is connected to the central portion 810c by a bridge portion 810bl, 810br having an arcuate corner portion and an arcuate portion curving opposite from the direction of curvature of the arcuate corners as shown in FIGS. 75–78. Each leg member has a sharp tip for penetrating mesh and body tissue. Right leg member 810r further possesses a tapered surface 810tr at the tip which is opposite the position of the tapered surface 810tl at the tip of the other leg member 810l.

When the lowermost staple 810 shown in FIG. 73 is advanced toward dual spaced anvils 816, 818 as shown in FIGS. 75–77 for example, staple pusher plate 604 as shown engages the arcuate portions of the bridge portions 810br and 810bl, and the legs of the staples are made to fold inwardly toward each other as shown for example in FIG. 77, with one leg crossing over the other. The cross-over configuration is automatically assumed by the legs because of the presence of tapered surfaces 810tr and 810tl which act as camming surfaces tending to bias each leg away from the other thereby tending to cross the legs in the manner shown. This structure also prevents interference of the legs when folded toward each other.

Thus, it can be seen that the particular shape of the staple as shown, promotes a folding pattern for the legs which achieves the configuration shown in the bent staple 810 of FIG. 77. Note in particular that inwardly bent central portion 810c promotes, for example, positive attachment of the mesh to the tissue by providing a gripping system between inwardly projecting bight portion 810c and leg members 810l, 810r with mesh and tissue gripped therebetween. This staple shape combines with the arrangement of the anvils and the particularly configured pusher plate 604 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pierces folds and grips in substantially a single movement.

FURTHER ALTERNATIVE EMBODIMENTS

As noted above, in a preferred alternative embodiment, first star wheel 684 is eliminated and the relief 618a in handle 612 is also eliminated. Collar 622 is arranged to provide several functions, as first noted. The first function is to articulate the staple cartridge 616 and cartridge support member 615 from 0° to a predetermined angle, (e.g. 65° in the preferred embodiment disclosed herein) by longitudinal proximal movement thereof. The second function is to return the staple cartridge 616 to 0° by distal movement thereof. The third function is to rotate the entire endoscopic section 614 and the staple cartridge 616 by direct connection therebetween as described hereinabove so that the cartridge may be made to sweep a conical path when it is articulated to 65°, for example, and the endoscopic section 614 is rotated up to a full 360°.

In another further alternative embodiment, as shown in FIGS. 80–81, the apparatus 910 may be a non-articulating surgical stapler including handle 912, grip 918, trigger 920, trigger stop device 950, and non-articulating elongated endoscopic section 914 having a longitudinal axis and a distal end 914d adapted to receive detachable staple cartridge 916. The non-articulating elongated endoscopic section 914 is attached to and rotated about the longitudinal axis by first star wheel 984. The alternative non-articulating surgical stapler 910 may incorporate the various features of the articulating stapler 610 and staple 810 as described above for FIGS. 64–79, such as stabilizing tabs 9221 and a spring channel member as in the previous embodiment.

What is claimed is:

1. Apparatus for endoscopic application of surgical staples which comprises:

a) a frame;

b) a generally elongated endoscopic portion extending distally from the frame and having a generally longitudinal axis and a distal end portion having a base portion;

c) means mounted upon said base portion for storing at least one surgical staple; and d) a movable staple pusher positioned at least partially within said endoscopic portion for advancing such at least one surgical staple, said staple pusher having at least two outer spaced projections extending distally for engaging and advancing a backspan of such at least one staple for application to body tissue, said staple pusher having a staple pusher surface for engaging the backspan, and at least two spaced inner projections respectively extending distally with respect to the staple pusher surface and positioned between said outer spaced projections for applying force to a central bight portion of the staple to prevent distortion of such at least one staple when the staple is formed about an anvil member.

2. Apparatus according to claim 1 wherein said distal end portion is movable between at least a first position extending in substantially the same direction as said longitudinal axis and at least a second position at an angle to said longitudinal axis.

3. Apparatus according to claim 1 wherein said staple pusher comprises a gap formed between said at least two spaced inner projections for providing relief to said staple pusher to slide smoothly over such anvil member.

4. Apparatus according to claim 1 further comprising an anvil member having at least two upstanding legs for closing such at least one surgical staple while applying same to body tissue.

5. Apparatus according to claim 4 wherein said upstanding legs each comprise a rounded proximal surface portion for forming such at least one surgical staple therearound to close such at least one surgical staple.

6. Apparatus according to claim 5 further comprising a spring channel member defining a channel which permits surgical staples to pass therethrough.

7. Apparatus according to claim 6 wherein said spring channel member comprises resilient means for moving a closed surgical staple upwardly with respect to such anvil member to release the staple therefrom after formation of the staple.

8. Apparatus according to claim 7 wherein said spring channel member comprises a projection for preventing surgical staples from moving in a proximal direction during application thereof to body tissue.

9. Apparatus according to claim 8 wherein said distal end portion comprises at least two distally extending tabs for engaging body tissue for stabilizing said distal end portion relative to the body tissue during application of such at least one surgical staple.

10. Apparatus for endoscopic application of surgical staples which comprises:

a) a frame;

b) a generally elongated endoscopic portion extending distally from the frame having a generally longitudinal axis and a distal end portion having a base portion, said distal end portion being movable between at least a first position extending in substantially the same direction as said longitudinal axis and a plurality of second positions at respective angles to said longitudinal axis;

c) means supported upon said base portion of said elongated endoscopic portion for storing at least one surgical staple; and d) at least two tabs extending distally from the distal end of said distal end portion and fixed with respect to said longitudinal axis for engaging body tissue for stabilizing said distal end portion relative to the body tissue during application of a staple.

11. Apparatus according to claim 10 further comprising a staple pusher having a staple pusher surface for engaging the backspan of such at least one staple and a gap formed between at least two inner projections respectively extending distally from said staple pusher surface for providing relief to said staple pusher to slide smoothly over an anvil member.

12. Apparatus according to claim 11 wherein such anvil member comprises at least two upstanding legs for closing the at least one surgical staple while applying same to body tissue.

13. Apparatus according to claim 12 wherein said upstanding legs each comprise a rounded surface portion for forming such at least one surgical staple therearound to close such at least one surgical staple.

14. Apparatus according to claim 10 further comprising a spring channel member positioned at the distal end of the endoscopic portion and defining a channel which permits surgical staples to pass therethrough.

15. Apparatus according to claim 14 wherein said spring channel member comprises resilient means for moving a closed surgical staple upwardly with respect to such anvil member to release the staple therefrom after formation of the staple.

16. Apparatus according to claim 15 wherein said spring channel member comprises a projection for preventing surgical staples from moving in a proximal direction during application thereof to body tissue.

17. Apparatus for endoscopic application of surgical staples which comprises:

a) a frame;

b) a generally elongated endoscopic tubular section extending distally from the frame and having a generally longitudinal axis and a distal end section;

c) a cartridge cooperating with the endoscopic tubular section for storing at least one surgical staple;

d) an anvil member having at least two upstanding legs each defining a rounded proximal surface for forming such at least one surgical staple therearound to close such at least one surgical staple while applying same to body tissue; and e) a staple pusher positioned at least partially within the endoscopic tubular section for movement to advance such at least one surgical staple, the staple pusher having at least two outer spaced projections extending distally for engaging and advancing a backspan of such at least one staple for application to body tissue and at least two spaced inner projections extending distally and positioned between the outer spaced projections for applying pressure to a central bight of the staple to prevent distortion of such at least one staple when the staple is formed about the anvil member.

18. Apparatus for endoscopic application of surgical staples which comprises:

a) a frame;

b) a generally elongated endoscopic tubular section extending distally from the frame and having a generally longitudinal axis and a distal end section, the distal end section being movable between at least a first position extending in substantially the same direction as the longitudinal axis and at least a second position at an angle to the longitudinal axis;

c) a cartridge cooperating with the endoscopic tubular section for storing at least one surgical staple;

d) an anvil member having at least two upstanding legs each defining a rounded proximal surface for forming such at least one surgical staple therearound to close such at least one surgical staple while applying same to body tissue;

e) a staple pusher having a gap formed between at least two inner projections for providing relief to the staple pusher to slide smoothly over the anvil member; and f) at least two tabs extending distally from the distal end of the distal end section for engaging body tissue for stabilizing the distal end section relative to the body tissue during application of a staple.

19. Apparatus for endoscopic application of surgical staples which comprises:

a) a frame;

b) a generally elongated endoscopic tubular section extending distally from the frame and having a generally longitudinal axis and a distal end section having a base;

c) a cartridge mounted upon the base;

d) a plurality of surgical staples stored in the cartridge;

e) an anvil member having at least two upstanding legs, the anvil member closing each surgical staple during application to body tissue; and f) a staple pusher movably positioned at least partially within the endoscopic tubular section, the staple pusher having at least two outer spaced projections extending distally, at least two staple pusher surfaces, and at least two spaced inner projections respectively extending distally from the staple pusher surfaces and positioned between the outer spaced projections, wherein the staple pusher surfaces engage the backspan of the staple and the inner projections apply pressure to a central bight of the staple to prevent distortion of the staple when the staple is formed about the anvil member.

* * * * *